United States Patent
Steinmeyer et al.

(10) Patent No.: US 7,071,344 B1
(45) Date of Patent: Jul. 4, 2006

(54) VITAMIN D DERIVATIVES WITH CYCLOPROPYL RINGS IN THE LATERAL CHAINS, A METHOD AND INTERMEDIATE PRODUCTS FOR THE PRODUCTION THEREOF AND THE UTILIZATION THEREOF FOR PRODUCING MEDICAMENTS

(75) Inventors: Andreas Steinmeyer, Berlin (DE); Gunter Neef, Berlin (DE); Gerald Kirsch, Berlin (DE); Katica Schwarz, Berlin (DE); Herbert Wiesinger, Berlin (DE); Martin Haberey, Berlin (DE); Marianne Fahnrich, Berlin (DE); Gernot Langer, Berlin (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 09/509,934

(22) PCT Filed: Sep. 29, 1998

(86) PCT No.: PCT/EP98/06159

§ 371 (c)(1),
(2), (4) Date: May 3, 2000

(87) PCT Pub. No.: WO99/16745

PCT Pub. Date: Apr. 8, 1999

(30) Foreign Application Priority Data

Oct. 1, 1997 (DE) ............................. 197 44 127

(51) Int. Cl.
*C07J 41/00* (2006.01)
*A61K 31/59* (2006.01)
(52) U.S. Cl. ..................................... 552/653; 514/167
(58) Field of Classification Search ............... 552/653, 552/652; 514/167
See application file for complete search history.

(56) References Cited

U.S. PATENT DOCUMENTS

| 5,190,935 | A | | 3/1993 | Binderup et al. |
| 5,583,125 | A | | 12/1996 | Steinmeyer et al. |
| 5,585,368 | A | * | 12/1996 | Steinmeyer et al. ........ 514/167 |
| 5,663,157 | A | | 9/1997 | Steinmeyer et al. |
| 5,700,791 | A | * | 12/1997 | Steinmeyer et al. ........ 514/167 |
| 6,372,731 | B1 | | 4/2002 | Kirsch et al. |
| 6,376,480 | B1 | | 4/2002 | Kirsch et al. |

FOREIGN PATENT DOCUMENTS

| DE | 42 20 757 A1 | 1/1994 |
| DE | 42 21 961 A1 | 1/1994 |
| DE | 42 34 382 A1 | 4/1994 |
| DE | 44 45 045 A1 | 6/1996 |
| DE | 196 19 036 A1 | 11/1997 |
| EP | 0 742 203 B1 | 9/1999 |
| WO | 87 00834 | 2/1987 |
| WO | 89 10351 | 11/1989 |
| WO | WO 94/14453 A1 | 7/1994 |
| WO | 97 00242 | 1/1997 |
| WO | WO 97/00242 A1 | 1/1997 |

OTHER PUBLICATIONS

Balasubramanian et al "Recent Developments in Cancer, Etc." Annual Reports in Medicinal Chemistry, 33, 1998, Academic Press, San Diego, pp. 151-159.*
Draetta (Ann. Reports Med. Chem.), Draetta et al. In "Annual Reports in Medicinal Chemistry"., 1996, Academic Press, San Diego, Section V, Capter 25, pp. 241-248.*

* cited by examiner

*Primary Examiner*—Sabiha N. Qazi
(74) *Attorney, Agent, or Firm*—Millen, White, Zelano, Branigan, P.C.

(57) ABSTRACT

The invention relates to novel vitamin D derivatives of general formula (I), a method for the production thereof, intermediate products of the method and the utilization of vitamin D derivatives for producing medicaments.

29 Claims, No Drawings

VITAMIN D DERIVATIVES WITH CYCLOPROPYL RINGS IN THE LATERAL CHAINS, A METHOD AND INTERMEDIATE PRODUCTS FOR THE PRODUCTION THEREOF AND THE UTILIZATION THEREOF FOR PRODUCING MEDICAMENTS

The invention relates to new vitamin D derivatives of general formula I

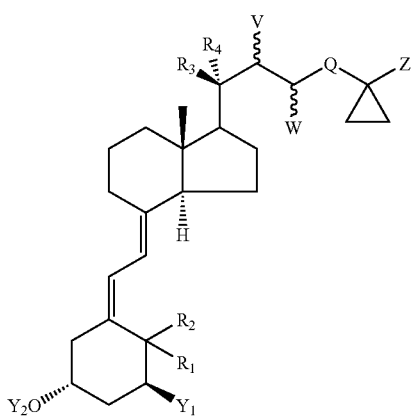

process for their production, intermediate products of the process as well as the use for the production of pharmaceutical agents.

PRIOR ART

Natural vitamins $D_2$ and $D_3$ are inherently biologically inactive and are converted into biologically active metabolites [$1\alpha$,25-dihydroxy vitamin $D_3$ (calcitriol) or -$D_2$] only after hydroxylation at C-atom 25 in the liver and at C-atom 1 in the kidney. The action of the active metabolites involves the regulation of the calcium and phosphate concentration in the serum; they counteract a dropping of the calcium concentration in the serum by increasing the calcium absorption in the intestine and under certain circumstances promoting calcium mobilization from the bones. FIG. 1 shows known vitamin D derivatives together with the commonly used numbering diagram.

In addition to their pronounced effect on the calcium and phosphate metabolism, the active metabolites of vitamins $D_2$ and $D_3$ and their synthetic derivatives have a proliferation-inhibiting and differentiation-stimulating action on tumor cells and normal cells, such as, for example, skin cells. In addition, a pronounced effect on cells of the immune system (inhibiting of proliferation and interleukin 2-synthesis of lymphocytes, increase of cytotoxicity and phagocytosis in vitro of monocytes) has been found, which manifests itself in an immunomodulatory action, and finally, because of a stimulating action on bone-forming cells, an increased formation of bone in normal and osteoporotic rats is found [R. Bouillon et al. "Short Term Course of 1,25(OH)$_2$D$_3$ Stimulates Osteoblasts But Not Osteoclasts," Calc. Tissue Int. 49, 168 (1991)].

All actions are mediated by bonding to the vitamin D receptor. Because of the bonding, the activity of specific genes is regulated.

When using biologically active metabolites of vitamins $D_2$ and $D_3$, a toxic effect on the calcium metabolism is produced (hypercalcemia).

By structural manipulations of the side chain, therapeutically usable effectiveness can be separated from undesirable hypercalcemic activity. A suitable structural variant is the introduction of 24-hydroxy derivatives.

$1\alpha$-Cholecalciferols that are hydroxylated in 24-position are already described in DE 25 26 981. They have a lower toxicity than the corresponding non-hydroxylated $1\alpha$-cholecalciferol. Further, 24-hydroxy derivatives are described in the following patent applications: DE 39 33 034, DE 40 03 854, DE 40 34 730, EP 0 421 561, EP 0 441 467, WO 87/00834, and WO 91/12238.

Finally, 25-carboxylic acid derivatives of calcitriol that are hydroxylated at C-24 are described in WO 94/07853, and said derivatives exhibit a more advantageous spectrum of action than calcitriol. The equivalent is also true for new vitamin D derivatives with substituents at C-25 (WO 97/00242). While the ability to trigger a hypercalcemia is considerably weakened, proliferation-inhibiting and differentiation-stimulating actions are maintained. Generally, however, the introduction of the 24-hydroxyl group results in metabolic destabilization of the derivatives, especially if a cyclopropyl ring is in the neigboring position. For this reason, these compounds are only conditionally suitable for systemic administration.

There is therefore a need for new vitamin D derivatives that have as advantageous a spectrum of action as the compounds that are described in the prior art (especially WO 94/07853 and WO 97/00242), but that are better suited for systemic administration owing to their higher metabolic stability.

The object of this patent application is to make available such vitamin D derivatives. This object is achieved by the compounds that are disclosed in the claims.

This invention therefore relates to vitamin D derivatives of general formula I,

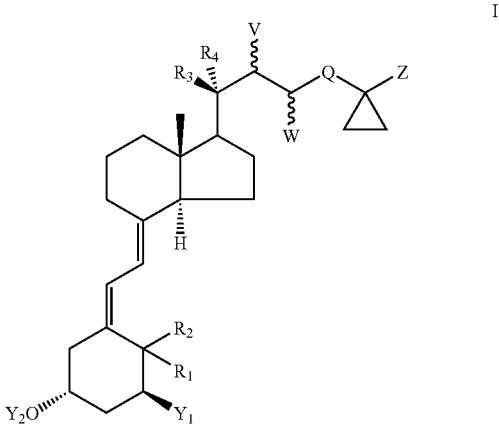

in which
  $Y_1$ means a hydrogen atom, a hydroxyl group, a fluorine, chlorine or bromine atom or a group —O(CO)R$_8$, in which
    $R_8$ is an aliphatic or aromatic radical with 1 to 12 C atoms,
  $Y_2$ means a hydrogen atom or a group —(CO)R$_9$, in which $R_9$ is an aliphatic or aromatic radical with 1 to 12 C atoms, $R_1$ and $R_2$ each mean a hydrogen atom or together an exocyclic methylene group, $R_3$ and $R_4$, independently of one another, mean a hydrogen atom, a chlorine or fluorine atom, an alkyl group with 1 to 4 carbon atoms, together a methylene group or together with quaternary carbon atom 20 a 3- to 7-membered, saturated or unsaturated carbocyclic ring, V and W together mean an E-double bond or V means a hydroxyl group and W means a hydrogen atom, Q means a straight-chain or branched carbon unit with up to 10 carbon atoms, which at any positions can have α- or β-hydroxyl groups, which in turn can be etherified or esterified, keto groups, amino groups or halogen atoms, Z means a straight-chain or branched-chain, saturated or unsaturated hydrocarbon radical with up to 12 carbon atoms, which at any positions can have keto groups, α- or β-hydroxyl groups, which in turn can be etherified or esterified, amino groups, fluorine, chlorine, or bromine atoms.

The invention also relates to a process for the production of the compounds according to the invention, intermediate products in the production process as well as use of the compounds according to the invention for the production of pharmaceutical agents.

Especially advantageous embodiments of the invention are the subject of the subclaims.

Radicals $R_1$ and $R_2$ preferably stand for hydrogen atoms.

For $R_3$ and $R_4$, the following preferred combinations apply: $R_3$=H, $R_4$=methyl or $R_3$=methyl, $R_4$=H; $R_3$=F, $R_4$=methyl or $R_3$=methyl, $R_4$=F; $R_3$, $R_4$=methyl; $R_3$ and $R_4$ together form a methylene group or together with tertiary carbon atom 20 form a cyclopropyl ring.

Optional radicals $R_8$ and $R_9$ are organic groups with 1 to 12 C atoms. These radicals can be saturated or unsaturated, branched or unbranched, acyclic, carbocyclic or heterocyclic. Examples of radicals $R_8$ and $R_9$ are methyl, ethyl, propyl, i-propyl, butyl or phenyl groups. The radicals of naturally occurring amino acids, such as, e.g., —CH$_2$—CH(CH$_3$)$_2$, —CH$_2$—Ph, —CH$_2$OH, —CH(OH)—CH$_3$, —CH$_2$SH, —CH$_2$—SCH$_3$, —CH$_2$CO$_2$H, —CH$_2$CH$_2$—CO$_2$H, —(CH$_2$)$_4$—NH$_2$, —(CH$_2$)$_3$—C(NH)NH$_2$, but also the radicals of the amino acids tryptophan, tyrosine or histamine are also possible, however.

The preferred radicals are derived from $C_1$ to $C_9$, especially $C_2$ to $C_5$ alkanecarboxylic acids, such as, for example, acetic acid, propionic acid, butyric acid or pivaloyl acid. Among the aromatic groups, the phenyl group and substituted phenyl groups are preferred.

Q is a straight-chain or branched carbon unit with up to 10 carbon atoms, e.g., —CH$_2$—, —(CH$_2$)$_2$—, —(CH$_2$)$_3$—, —(CH$_2$)$_4$—, —(CH$_2$)$_7$—, —CH$_2$—C(CH$_3$)$_2$—CH$_2$—, —CH$_2$—CH(CH$_3$)—CH$_2$—CH(CH$_3$)—CH$_2$—. The carbon atoms that are contained in Q can have hydroxyl groups at any positions, e.g., —CH(OH)—, —CH$_2$—CH(OH)—, —CH$_2$—CH$_2$—CH(OH)—, —CH(OH)—CH$_2$—, —CH(OH)—CH$_2$—CH$_2$—, —CH$_2$—CH(OH)—CH$_2$—CH(OH)—CH$_2$—, —CH$_2$—CH(OH)—CH$_2$—, —CH$_2$—CH(OH)—CH$_2$—CH(OH)—CH$_2$—. The hydroxyl groups can in turn be esterified or etherified, e.g., —CH(OCH$_3$)—, —CH$_2$—CH(OC$_2$H$_5$)—, —CH$_2$—CH(OCOCH$_3$)—CH$_2$—CH(OCOCH$_3$)—CH$_2$—, —CH$_2$—CH(OCOC$_4$H$_9$)—CH$_2$—. Group Q can also exhibit keto groups, amino groups or halogen atoms, e.g., —CO—, —CO—CH$_2$—, —CO—CH$_2$—CH$_2$—, —CH$_2$COCH$_2$—, —CH(Cl)—, —CH(Cl)—CH$_2$—, —CH$_2$—CH(Cl)—, —CH(NH$_2$)—, —CH(NH$_2$)—CH$_2$—, —CH(N(CH$_3$)$_2$)—, —CH(N(CH$_3$)$_2$)—CH$_2$—, —CH$_2$—CH(N(CH$_3$)$_2$)—CH$_2$—CH(N(CH$_3$)$_2$)—CH$_2$—, —CH(F)—, —CH(F)—CH$_2$—, —CH$_2$—CH(F)—CH$_2$.

The following groups Q are preferred:

Q is an unsubstituted, unbranched alkylene unit with 1, 2 or 3 carbon atoms or

Q is a hydroxymethylene group (hydroxyl group in α- or β-position) or

Q=—CH(OH)—CH$_2$— or —CH(OH)—CH$_2$—CH$_2$— (hydroxyl groups in α or β-position).

Radical Y1 preferably stands for a hydrogen atom, a fluorine atom or a hydroxyl group.

Z is a straight-chain or branched-chain, saturated or unsaturated hydrocarbon radical with up to 12 carbon atoms, e.g., —CH$_3$, —CH$_2$—CH$_3$, —(CH$_2$)$_2$—CH$_3$, —(CH$_2$)$_3$—CH$_3$, —(CH$_2$)$_4$—CH$_3$, —(CH$_2$)$_5$—CH$_3$, —(CH$_2$)$_6$—CH$_3$, —(CH$_2$)$_7$—CH$_3$, —CH$_2$—C(CH$_3$)$_2$—CH$_2$—CH$_3$, —CH$_2$—CH(CH$_3$)—CH$_2$—CH(CH$_3$)—CH$_2$—CH$_3$. The carbon atoms that are contained in Z can exhibit hydroxyl groups at any positions, e.g., —CH(OH)—CH$_3$, —CH$_2$—CH(OH)—CH$_3$, —CH$_2$—CH(OH)—CH$_2$—CH(OH)—CH$_2$—CH$_3$, —CH$_2$—CH(OH)—CH$_2$—CH$_3$, —CH$_2$—CH(OH)—CH$_2$—CH(OH)—CH$_2$—CH$_3$. In turn, the hydroxyl groups can be esterified or etherified, e.g., —CH(OCH$_3$)—CH$_3$, —CH$_2$—CH(OC$_2$H$_5$)—CH$_3$, —CH$_2$—CH(OCOCH$_3$)—CH$_2$—CH(OCOCH$_3$)—CH$_2$—CH$_3$, —CH$_2$—CH(OCOC$_4$H$_9$)—CH$_2$—CH$_3$. Group Z can also exhibit keto groups, amino groups or halogen atoms, e.g., —CH$_2$COCH$_2$—CH$_3$, —CH$_2$—CH(Cl)—CH$_3$, —CH$_2$—CH(N(CH$_3$)$_2$)—CH$_2$—CH(N(CH$_3$)$_2$)—CH$_2$—CH$_3$, —CH$_2$—CH(F)—CH$_2$—CH$_3$.

The following groups Z are preferred:

Z is a 1-oxoalkyl group with 1–12 carbon atoms,

Z is an alkyl group with 1–12 carbon atoms,

Z is an alkenyl group with 1–12 carbon atoms, in which the double bond can have E- or Z-geometry and can be present at any positions of the side chain.

The groups V and W either together form an E-double bond or V is a hydroxyl group and W is a hydrogen atom. The two possibilities for the structural element in question are pictured below:

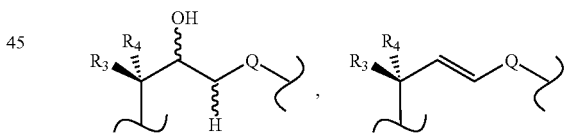

Of the compounds of general formula I according to the invention, the following compounds are quite especially preferred:

(5Z,7E,22E)-(1S,3R)-25-Acetyl-26,27-cyclo-9,10-secocholesta-5,7,10(19),22-tetraene-1,3-diol, (5Z,7E,22E)-(1S,3R)-25-(1-oxopropyl)-26,27-cyclo-9,10-secocholesta-5,7,10(19),22-tetraene-1,3-diol, (5Z,7E,22E)-(1S,3R)-25-(1-oxobutyl)-26,27-cyclo-9,10-secocholesta-5,7,10(19),22-tetraene-1,3-diol, (5Z,7E,22E)-(1S,3R)-25-(1-oxopentyl)-26,27-cyclo-9,10-secocholesta-5,7,10(19),22-tetraene-1,3-diol, (5Z,7E,22E)-(1S,3R)-25-(1-oxohexyl)-26,27-cyclo-9,10-secocholesta-5,7,10(19),22-tetraene-1,3-diol, (5Z,7E,22E)-(1S,3R)-25-(1-oxoheptyl)-26,27-cyclo-9,10-secocholesta-5,7,10(19),22-tetraene-1,3-diol, (5Z,7E,22E)-(1S,3R)-25-(1-oxooctyl)-26,27-cyclo-9,10-secocholesta-5,7,10(19),22-tetraene-1,3-diol, (5Z,7E,22E)-(1S,3R)-25-(1-oxononyl)-26,27-cyclo-9,10-secocholesta-5,7,10(19),22-tetraene-1,3-diol,
(5Z,7E,22E)-(1S,3R)-25-(1-oxodecyl)-26,27-cyclo-9,10-secocholesta-5,7,10(19),22-tetraene-1,3-diol,
(5Z,7E)-(1S,3R,22S)-25-acetyl-26,27-cyclo-9,10-secocholesta-5,7,10(19)-triene-1,3,22-triol,
(5Z,7E)-(1S,3R,22R)-25-acetyl-26,27-cyclo-9,10-secocholesta-5,7,10(19)-triene-1,3,22-triol,
(5Z,7E)-(1S,3R,22S)-25-(1-oxopropyl)-26,27-cyclo-9,10-secocholesta-5,7,10(19)-triene-1,3,22-triol,
(5Z,7E)-(1S,3R,22R)-25-(1-oxopropyl)-26,27-cyclo-9,10-secocholesta-5,7,10(19)-triene-1,3,22-triol,
(5Z,7E)-(1S,3R,22S)-25-(1-oxobutyl)-26,27-cyclo-9,10-secocholesta-5,7,10(19)-triene-1,3,22-triol,
(5Z,7E)-(1S,3R,22R)-25-(1-oxobutyl)-26,27-cyclo-9,10-secocholesta-5,7,10(19)-triene-1,3,22-triol,
(5Z,7E)-(1S,3R,22S)-25-(1-oxopentyl)-26,27-cyclo-9,10-secocholesta-5,7,10(19)-triene-1,3,22-triol,
(5Z,7E)-(1S,3R,22R)-25-(1-oxopentyl)-26,27-cyclo-9,10-secocholesta-5,7,10(19)-triene-1,3,22-triol,
(5Z,7E)-(1S,3R,22S)-25-(1-oxohexyl)-26,27-cyclo-9,10-secocholesta-5,7,10(19)-triene-1,3,22-triol,
(5Z,7E)-(1S,3R,22R)-25-(1-oxohexyl)-26,27-cyclo-9,10-secocholesta-5,7,10(19)-triene-1,3,22-triol,
(5Z,7E)-(1S,3R,22S)-25-(1-oxoheptyl)-26,27-cyclo-9,10-secocholesta-5,7,10 (19)-triene-1,3,22-triol,
(5Z,7E)-(1S,3R,22R)-25-(1-oxoheptyl)-26,27-cyclo-9,10-secocholesta-5,7,10(19)-triene-1,3,22-triol,
(5Z,7E)-(1S,3R,22S)-25-(1-oxooctyl)-26,27-cyclo-9,10-secocholesta-5,7,10(19)-triene-1,3,22-triol, (5Z,7E)-(1S,3R,22R)-25-(1-oxooctyl)-26,27-cyclo-9,10-secocholesta-5,7,10 (19)-triene-1,3,22-triol,
(5Z,7E)-(1S,3R,22S)-25-(1-oxononyl)-26,27-cyclo-9,10-secocholesta-5,7,10-(19)-triene-1,3,22-triol,
(5Z,7E)-(1S,3R,22R)-25-(1-oxononyl)-26,27-cyclo-9,10-secocholesta-5,7,10(19)-triene-1,3,22-triol,
(5Z,7E)-(1S,3R,22S)-25-(1-oxodecyl)-26,27-cyclo-9,10-secocholesta-5,7,10(19)-triene-1,3,22-triol,
(5Z,7E)-(1S,3R,22R)-25-(1-oxodecyl)-26,27-cyclo-9,10-secocholesta-5,7,10(19)-triene-1,3,22-triol,
(5Z,7E,22E)-(1S,3R)-25-acetyl-26,27-cyclo-24a-homo-9,10-secocholesta-5,7,10(19),22-tetraene-1,3-diol,
(5Z,7E,22E)-(1S,3R)-25-(1-oxopropyl)-26,27-cyclo-24a-homo-9,10-secocholesta-5,7,10(19),22-tetraene-1,3-diol,
(5Z,7E,22E)-(1S,3R)-25-(1-oxobutyl)-26,27-cyclo-24a-homo-9,10-secocholesta-5,7,10(19),22-tetraene-1,3-diol,
(5Z,7E,22E)-(1S,3R)-25-(1-oxopentyl)-26,27-cyclo-24a-homo-9,10-secocholesta-5,7,10(19),22-tetraene-1,3-diol,
(5Z,7E,22E)-(1S,3R)-25-(1-oxohexyl)-26,27-cyclo-24a-homo-9,10-secocholesta-5,7,10(19),22-tetraene-1,3-diol,
(5Z,7E,22E)-(1S,3R)-25-(1-oxoheptyl)-26,27-cyclo-24a-homo-9,10-secocholesta-5,7,10(19),22-tetraene-1,3-diol,
(5Z,7E,22E)-(1S,3R)-25-(1-oxooctyl)-26,27-cyclo-24a-homo-9,10-secocholesta-5,7,10(19),22-tetraene-1,3-diol,
(5Z,7E,22E)-(1S,3R)-25-(1-oxononyl)-26,27-cyclo-24a-homo-9,10-secocholesta-5,7,10(19),22-tetraene-1,3-diol,
(5Z,7E,22E)-(1S,3R)-25-(1-oxodecyl)-26,27-cyclo-24a-homo-9,10-secocholesta-5,7,10(19),22-tetraene-1,3-diol,
(5Z,7E)-(1S,3R,22S)-25-acetyl-26,27-cyclo-24a-homo-9,10-secocholesta-5,7,10(19)-triene-1,3,22-triol,
(5Z,7E)-(1S,3R,22R)-25-acetyl-26,27-cyclo-24a-homo-9,10-secocholesta-5,7,10(19)-triene-1,3,22-triol,
(5Z,7E)-(1S,3R,22S)-25-(1-oxopropyl)-26,27-cyclo-24a-homo-9,10-secocholesta-5,7,10(19)-triene-1,3,22-triol,
(5Z,7E)-(1S,3R,22R)-25-(1-oxopropyl)-26,27-cyclo-24a-homo-9,10-secocholesta-5,7, 10(19)-triene-1,3,22-triol,
(5Z,7E)-(1S,3R,22S)-25-(1-oxobutyl)-26,27-cyclo-24a-homo-9,10-secocholesta-5,7,10(19)-triene-1,3,22-triol,
(5Z,7E)-(1S,3R,22R)-25-(1-oxobutyl)-26,27-cyclo-24a-homo-9,10-secocholesta-5,7,10(19)-triene-1,3,22-triol,
(5Z,7E)-(1S,3R,22S)-25-(1-oxopentyl)-26,27-cyclo-24a-homo-9,10-secocholesta-5,7,10(19)-triene-1,3,22-triol,
(5Z,7E)-(1S,3R,22R)-25-(1-oxopentyl)-26,27-cyclo-24a-homo-9,10-secocholesta-5,7,10(19)-triene-1,3,22-triol,
(5Z,7E)-(1S,3R,22S)-25-(1-oxohexyl)-26,27-cyclo-24a-homo-9,10-secocholesta-5,7,10 (19)-triene-1,3,22-triol,
(5Z, 7E)-(1S,3R,22R)-25-(1-oxohexyl)-26,27-cyclo-24a-homo-9,10-secocholesta-5,7,10(19)-triene-1,3,22-triol,
(5Z,7E)-(1S,3R,22S)-25-(1-oxoheptyl)-26,27-cyclo-24a-homo-9,10-secocholesta-5,7,10(19)-triene-1,3,22-triol,
(5Z,7E)-(1S,3R,22R)-25-(1-oxoheptyl)-26,27-cyclo-24a-homo-9,10-secocholesta-5,7,10(19)-triene-1,3,22-triol,
(5Z,7E)-(1S,3R,22S)-25-(1-oxooctyl)-26,27-cyclo-24a-homo-9,10-secocholesta-5,7,10(19)-triene-1,3,22-triol,
(5Z,7E)-(1S,3R,22R)-25-(1-oxooctyl)-26,27-cyclo-24a-homo-9,10-secocholesta-5,7,10(19)-triene-1,3,22-triol,
(5Z,7E)-(1S,3R,22S)-25-(1-oxononyl)-26,27-cyclo-24a-homo-9,10-secocholesta-5,7,10(19)-triene-1,3,22-triol,
(5Z,7E)-(1S,3R,22R)-25-(1-oxononyl)-26,27-cyclo-24a-homo-9,10-secocholesta-5,7,10(19)-triene-1,3,22-triol,
(5Z,7E)-(1S,3R,22S)-25-(1-oxodecyl)-26,27-cyclo-24a-homo-9,10-secocholesta-5,7,10(19)-triene-1,3,22-triol,
(5Z,7E)-(1S,3R,22R)-25-(1-oxodecyl)-26,27-cyclo-24a-homo-9,10-secocholesta-5,7,10(19)-triene-1,3,22-triol,
(5Z,7E,22E)-(1S,3R,24R)-25-acetyl-26,27-cyclo-24a,24b-dihomo-9,10-secocholesta-5,7,10(19),22-tetraene-1,3,24-triol,
(5Z,7E,22E)-(1S,3R,24S)-25-acetyl-26,27-cyclo-24a,24b-dihomo-9,10-secocholesta-5,7,10(19),22-tetraene-1,3,24-triol,
(5Z,7E,22E)-(1S,3R,24R)-25-(1-oxopropyl)-26,27-cyclo-24a,24b-dihomo-9,10-secocholesta-5,7,10(19),22-tetraene-1,3,24-triol,
(5Z,7E,22E)-(1S,3R,24S)-25-(1-oxopropyl)-26,27-cyclo-24a,24b-dihomo-9,10-secocholesta-5,7,10(19),22-tetraene-1,3,24-triol,
(5Z,7E,22E)-(1S,3R,24R)-25-(1-oxobutyl)-26,27-cyclo-24a,24b-dihomo-9,10-secocholesta-5,7,10(19),22-tetraene-1,3,24-triol,
(5Z,7E,22E)-(1S,3R,24S)-25-(1-oxobutyl)-26,27-cyclo-24a,24b-dihomo-9,10-secocholesta-5,7,10(19),22-tetraene-1,3,24-triol,
(5Z,7E,22E)-(1S,3R,24R)-25-(1-oxopentyl)-26,27-cyclo-24a,24b-dihomo-9,10-secocholesta-5,7,10(19),22-tetraene-1,3,24-triol,
(5Z,7E,22E)-(1S,3R,24S)-25-(1-oxopentyl)-26,27-cyclo-24a,24b-dihomo-9,10-secocholesta-5,7,10(19),22-tetraene-1,3,24-triol,
(5Z,7E,22E)-(1S,3R,24R)-25-(1-oxohexyl)-26,27-cyclo-24a,24b-dihomo-9,10-secocholesta-5,7,10(19),22-tetraene-1,3,24-triol,
(5Z,7E,22E)-(1S,3R, 24S)-25-(1-oxohexyl)-26,27-cyclo-24a,24b-dihomo-9,10-secocholesta-5,7,10(19),22-tetraene-1,3,24-triol,
(5Z,7E,22E)-(1S,3R,24R)-25-(1-oxoheptyl)-26,27-cyclo-24a,24b-dihomo-9,10-secocholesta-5,7,10(19),22-tetraene-1,3,24-triol,
(5Z,7E,22E)-(1S,3R,24S)-25-(1-oxoheptyl)-26,27-cyclo-24a,24b-dihomo-9,10-secocholesta-5,7,10(19),22-tetraene-1,3,24-triol,
(5Z,7E,22E)-(1S,3R,24R)-25-(1-oxooctyl)-26,27-cyclo-24a,24b-dihomo-9,10-secocholesta-5,7,10(19),22-tetraene-1,3,24-triol, (5Z,7E,22E)-(1S,3R,24S)-25-(1-oxooctyl)-26,27-cyclo-24a,24b-dihomo-9,10-secocholesta-5,7,10(19),22-tetraene-1,3,24-triol, (5Z,7E,22E)-(1S,3R,24R)-25-(1-oxononyl)-26,27-cyclo-24a,24b-dihomo-9,10-secocholesta-5,7,10(19),22-tetraene-1,3,24-triol, (5Z,7E,22E)-(1S,3R,24S)-25-(1-oxononyl)-26,27-cyclo-24a,24b-dihomo-9,10-secocholesta-5,7,10(19),22-tetraene-1,3,24-triol, (5Z,7E,22E)-(1S,3R,24R)-25-(1-oxodecyl)-26,27-cyclo-24a,24b-dihomo-9,10-secocholesta-5,7,10(19),22-tetraene-1,3,24-triol, (5Z,7E,22E)-(1S,3R,24S)-25-(1-oxodecyl)-26,27-cyclo-24a,24b-dihomo-9,10-secocholesta-5,7,10(19),22-tetraene-1,3,24-triol, (5Z,7E,22E)-(1S,3R,24R)-25-acetyl-24-methoxy-26,27-cyclo-24a,24b-dihomo-9,10-secocholesta-5,7,10(19),22-tetraene-1,3-diol, (5Z,7E,22E)-(1S,3R,24S)-25-acetyl-24-methoxy-26,27-cyclo-24a,24b-dihomo-9,10-secocholesta-5,7,10(19),22-tetraene-1,3-diol, (5Z,7E,22E)-(1S,3R,24R)-24-methoxy-25-(1-oxopropyl)-26,27-cyclo-24a,24b-dihomo-9,10-secocholesta-5,7,10(19),22-tetraene-1,3-diol, (5Z,7E,22E)-(1S,3R,24S)-24-methoxy-25-(1-oxopropyl)-26,27-cyclo-24a,24b-dihomo-9,10-secocholesta-5,7,10(19),22-tetraene-1,3-diol, (5Z,7E,22E)-(1S,3R,24R)-24-methoxy-25-(1-oxobutyl)-26,27-cyclo-24a,24b-dihomo-9,10-secocholesta-5,7,10(19),22-tetraene-1,3-diol, (5Z,7E,22E)-(1S,3R,24S)-24-methoxy-25-(1-oxobutyl)-26,27-cyclo-24a,24b-dihomo-9,10-secocholesta-5,7,10(19),22-tetraene-1,3-diol, (5Z,7E,22E)-(1S,3R,24R)-24-methoxy-25-(1-oxopentyl)-26,27-cyclo-24a,24b-dihomo-9,10-secocholesta-5,7,10(19),22-tetraene-1,3-diol, (5Z,7E,22E)-(1S,3R,24S)-24-methoxy-25-(1-oxopentyl)-26,27-cyclo-24a,24b-dihomo-9,10-secocholesta-5,7,10(19),22-tetraene-1,3-diol, (5Z,7E,22E)-(1S,3R,24R)-24-methoxy-25-(1-oxohexyl)-26,27-cyclo-24a,24b-dihomo-9,10-secocholesta-5,7,10(19), 22-tetraene-1,3-diol, (5Z,7E,22E)-(1S,3R,24S)-24-methoxy-25-(1-oxohexyl)-26,27-cyclo-24a,24b-dihomo-9,10-secocholesta-5,7,10(19),22-tetraene-1,3-diol, (5Z,7E,22E)-(1S,3R,24R)-24-methoxy-25-(1-oxoheptyl)-26,27-cyclo-24a,24b-dihomo-9,10-secocholesta-5,7,10(19),22-tetraene-1,3-diol, (5Z,7E,22E)-(1S,3R,24S)-24-methoxy-25-(1-oxoheptyl)-26,27-cyclo-24a,24b-dihomo-9,10-secocholesta-5,7,10(19),22-tetraene-1,3-diol, (5Z,7E,22E)-(1S,3R,24R)-24-methoxy-25-(1-oxooctyl)-26,27-cyclo-24a,24b-dihomo-9,10-secocholesta-5,7,10(19),22-tetraene-1,3-diol, (5Z,7E,22E)-(1S,3R,24S)-24-methoxy-25-(1-oxooctyl)-26,27-cyclo-24a,24b-dihomo-9,10-secocholesta-5,7,10(19),22-tetraene-1,3-diol, (5Z,7E,22E)-(1S,3R,24R)-24-methoxy-25-(1-oxononyl)-26,27-cyclo-24a,24b-dihomo-9,10-secocholesta-5,7,10(19),22-tetraene-1,3-diol, (5Z,7E,22E)-(1S,3R,24S)-24-methoxy-25-(1-oxononyl)-26,27-cyclo-24a,24b-dihomo-9,10-secocholesta-5,7,10(19),22-tetraene-1,3-diol, (5Z,7E,22E)-(1S,3R,24R)-24-methoxy-25-(1-oxodecyl)-26,27-cyclo-24a,24b-dihomo-9,10-secocholesta-5,7,10(19),22-tetraene-1,3-diol, (5Z,7E,22E)-(1S,3R,24S)-24-methoxy-25-(1-oxodecyl)-26,27-cyclo-24a,24b-dihomo-9,10-secocholesta-5,7,10(19),22-tetraene-1,3-diol, (5Z,7E,22E)-(1S,3R,24S)-25-methyl-26,27-cyclo-9,10-secocholesta-5,7,10(19),22-tetraene-1,3,24-triol, (5Z,7E,22E)-(1S,3R,24R)-25-methyl-26, 27-cyclo-9,10-secocholesta-5,7,10(19),22-tetraene-1,3,24-triol, (5Z,7E,22E)-(1S,3R,24S)-25-ethyl-26,27-cyclo-9,10-secocholesta-5,7,10(19),22-tetraene-1,3,24-triol, (5Z,7E,22E)-(1S,3R,24R)-25-ethyl-26,27-cyclo-9,10-secocholesta-5,7,10(19),22-tetraene-1,3,24-triol, (5Z,7E,22E)-(1S,3R,24S)-25-propyl-26,27-cyclo-9,10-secocholesta-5,7,10(19),22-tetraene-1,3,24-triol, (5Z,7E,22E)-(1S,3R,24R)-25-propyl-26,27-cyclo-9,10-secocholesta-5,7,10(19),22-tetraene-1,3,24-triol, (5Z,7E,22E)-(1S,3R,24S)-25-butyl-26,27-cyclo-9,10-secocholesta-5,7,10(19),22-tetraene-1,3,24-triol, (5Z,7E,22E)-(1S,3R,24R)-25-butyl-26,27-cyclo-9,10-secocholesta-5,7,10(19),22-tetraene-1,3,24-triol, (5Z,7E,22E)-(1S,3R,24S)-25-pentyl-26,27-cyclo-9,10-secocholesta-5,7,10(19),22-tetraene-1,3,24-triol, (5Z,7E,22E)-(1S,3R,24R)-25-pentyl-26,27-cyclo-9,10-secocholesta-5,7,10(19),22-tetraene-1,3,24-triol, (5Z,7E,22E)-(1S,3R,24S)-25-hexyl-26,27-cyclo-9,10-secocholesta-5,7,10 (19),22-tetraene-1,3,24-triol, (5Z,7E,22E)-(1S,3R,24R)-25-hexyl-26,27-cyclo-9,10-secocholesta-5,7,10(19),22-tetraene-1,3,24-triol, (5Z,7E,22E)-(1S,3R,24S)-25-heptyl-26,27-cyclo-9,10-secocholesta-5,7,10(19),22-tetraene-1,3,24-triol, (5Z,7E,22E)-(1S,3R,24R)-25-heptyl-26,27-cyclo-9,10-secocholesta-5,7,10(19),22-tetraene-1,3,24-triol, (5Z,7E,22E)-(1S,3R,24S)-25-octyl-26,27-cyclo-9,10-secocholesta-5,7,10(19),22-tetraene-1,3,24-triol, (5Z,7E,22E)-(1S,3R,24R)-25-octyl-26,27-cyclo-9,10-secocholesta-5,7,10(19),22-tetraene-1,3,24-triol, (5Z,7E,22E)-(1S,3R,24S)-25-nonyl-26,27-cyclo-9,10-secocholesta-5,7,10(19),22-tetraene-1,3,24-triol, (5Z,7E,22E)-(1S,3R,24R)-25-nonyl-26,27-cyclo-9,10-secocholesta-5,7,10(19),22-tetraene-1,3,24-triol, (5Z,7E,22E)-(1S,3R,24S)-25-decyl-26,27-cyclo-9,10-secocholesta-5,7,10(19),22-tetraene-1,3,24-triol, (5Z,7E,22E)-(1S,3R,24R)-25-decyl-26,27-cyclo-9,10-secocholesta-5,7,10(19),22-tetraene-1,3,24-triol, (5Z,7E,22E)-(1S,3R,24S)-25-ethylene-26,27-cyclo-9,10-secocholesta-5,7,10(19),22-tetraene-1,3,24-triol, (5Z,7E,22E)-(1S,3R,24R)-25-ethylene-26,27-cyclo-9,10-secocholesta-5,7,10(19),22-tetraene-1,3,24-triol,

[5Z,7E,22E,25(E)]-(1S,3R,24S)-25-(1-propenyl)-26,27-cyclo-9,10-secocholesta-5,7,10(19),22-tetraene-1,3,24-triol,

[5Z,7E,22E,25(E)]-(1S,3R,24R)-25-(1-propenyl)-26,27-cyclo-9,10-secocholesta-5,7,10(19),22-tetraene-1,3,24-triol,

[5Z,7E,22E,25(E)]-(1S,3R,24S)-25-(1-butenyl)-26,27-cyclo-9,10-secocholesta-5,7,10(19),22-tetraene-1,3,24-triol,

[5Z,7E,22E,25(E)]-(1S,3R,24R)-25-(1-butenyl)-26,27-cyclo-9,10-secocholesta-5,7,10(19),22-tetraene-1,3,24-triol,

[5Z,7E,22E,25(E)]-(1S,3R,24S)-25-(1-pentenyl)-26,27-cyclo-9,10-secocholesta-5,7,10(19),22-tetraene-1,3,24-triol,

[5Z,7E,22E,25(E)]-(1S,3R,24R)-25-(1-pentenyl)-26,27-cyclo-9,10-secocholesta-5,7,10(19),22-tetraene-1,3,24-triol,

[5Z,7E,22E,25(E)]-(1S,3R,24S)-25-(1-hexenyl)-26,27-cyclo-9,10-secocholesta-5,7,10(19),22-tetraene-1,3,24-triol,

[5Z,7E,22E,25(E)]-(1S,3R,24R)-25-(1-hexenyl)-26,27-cyclo-9,10-secocholesta-5,7,10(19),22-tetraene-1,3,24-triol,

[5Z,7E,22E,25(E)]-(1S,3R,24S)-25-(1-heptenyl)-26,27-cyclo-9,10-secocholesta-5,7,10(19),22-tetraene-1,3,24-triol,

[5Z,7E,22E,25(E)]-(1S,3R,24R)-25-(1-heptenyl)-26,27-cyclo-9,10-secocholesta-5,7,10(19),22-tetraene-1,3,24-triol,

[5Z,7E,22E,25(E)]-(1S,3R,24S)-25-(1-octenyl)-26,27-cyclo-9,10-secocholesta-5,7,10(19),22-tetraene-1,3,24-triol,

[5Z,7E,22E,25(E)]-(1S,3R,24R)-25-(1-octenyl)-26,27-cyclo-9,10-secocholesta-5,7,10(19),22-tetraene-1,3,24-triol,

[5Z,7E,22E,25(E)]-(1S,3R,24S)-25-(1-nonenyl)-26,27-cyclo-9,10-secocholesta-5,7,10(19),22-tetraene-1,3,24-triol,

[5Z,7E,22E,25(E)]-(1S,3R,24R)-25-(1-nonenyl)-26,27-cyclo-9,10-secocholesta-5,7,10(19),22-tetraene-1,3,24-triol,

[5Z,7E,22E,25(E)]-(1S,3R,24S)-25-(1-decenyl)-26,27-cyclo-9,10-secocholesta-5,7,10(19),22-tetraene-1,3,24-triol,

[5Z,7E,22E,25(E)]-(1S,3R,24R)-25-(1-decenyl)-26,27-cyclo-9,10-secocholesta-5,7,10(19),22-tetraene-1,3,24-triol,

[5Z,7E,22E,25(Z)]-(1S,3R,24S)-25-(1-propenyl)-26,27-cyclo-9,10-secocholesta-5,7,10(19),22-tetraene-1,3,24-triol,

[5Z,7E,22E,25(Z)]-(1S,3R,24R)-25-(1-propenyl)-26,27-cyclo-9,10-secocholesta-5,7,10(19),22-tetraene-1,3,24-triol,

[5Z,7E,22E,25(Z)]-(1S,3R,24S)-25-(1-butenyl)-26,27-cyclo-9,10-secocholesta-5,7,10(19),22-tetraene-1,3,24-triol,

[5Z,7E,22E,25(Z)]-(1S,3R,24R)-25-(1-butenyl)-26,27-cyclo-9,10-secocholesta-5,7,10(19),22-tetraene-1,3,24-triol,

[5Z,7E,22E,25(Z)]-(1S,3R,24S)-25-(1-pentenyl)-26,27-cyclo-9,10-secocholesta-5,7,10(19),22-tetraene-1,3,24-triol,

[5Z,7E,22E,25(Z)]-(1S,3R,24R)-25-(1-pentenyl)-26,27-cyclo-9,10-secocholesta-5,7,10(19),22-tetraene-1,3,24-triol,

[5Z,7E,22E,25(Z)]-(1S,3R,24S)-25-(1-hexenyl)-26,27-cyclo-9,10-secocholesta-5,7,10(19),22-tetraene-1,3,24-triol,

[5Z,7E,22E,25(Z)]-(1S,3R,24R)-25-(1-hexenyl)-26,27-cyclo-9,10-secocholesta-5,7,10(19),22-tetraene-1,3,24-triol,

[5Z,7E,22E,25(Z)]-(1S,3R,24S)-25-(1-heptenyl)-26,27-cyclo-9,10-secocholesta-5,7,10(19),22-tetraene-1,3,24-triol,

[5Z,7E,22E,25(Z)]-(1S,3R,24R)-25-(1-heptenyl)-26,27-cyclo-9,10-secocholesta-5,7,10(19),22-tetraene-1,3,24-triol,

[5Z,7E,22E,25(Z)]-(1S,3R,24S)-25-(1-octenyl)-26,27-cyclo-9,10-secocholesta-5,7,10(19),22-tetraene-1,3,24-triol,

[5Z,7E,22E,25(Z)]-(1S,3R,24R)-25-(1-octenyl)-26,27-cyclo-9,10-secocholesta-5,7,10(19),22-tetraene-1,3,24-triol,

[5Z,7E,22E,25(Z)])-(1S,3R,24S)-25-(1-nonenyl)-26,27-cyclo-9,10-secocholesta-5,7,10(19),22-tetraene-1,3,24-triol,

[5Z,7E,22E,25(Z)]-(1S,3R,24R)-25-(1-nonenyl)-26,27-cyclo-9,10-secocholesta-5,7,10(19),22-tetraene-1,3,24-triol,

[5Z,7E,22E,25(Z)]-(1S,3R,24S)-25-(1-decenyl)-26,27-cyclo-9,10-secocholesta-5,7,10(19),22-tetraene-1,3,24-triol,

[5Z,7E,22E,25(Z)]-(1S,3R,24R)-25-(1-decenyl)-26,27-cyclo-9,10-secocholesta-5,7,10(19),22-tetraene-1,3,24-triol.

The substances according to the invention have a considerably higher metabolic stability than the structurally related compounds of the prior art and are therefore suitable in a special way for systemic administrations.

Relative to the structurally related compounds of the prior art, some of the substances according to the invention are also characterized in that they show a stronger action on cell differentiation, whereby the action on the calcium balance does not increase. Others of the substances according to the invention, however, exhibit an antagonistic or partial agonistic profile of action, which makes possible new uses.

Determination of Biological Activity

The vitamin D activity of the substances according to the invention is determined with the aid of the calcitriol-receptor test. It is carried out using a protein extract from the intestines of juvenile pigs.

Receptor-containing protein extract is incubated in a test tube with $^3$H-calcitriol ($5 \times 10^{-10}$ mol/l) in a reaction volume of 0.270 ml in the absence and in the presence of test substances for two hours at 4° C. To separate free and receptor-bound calcitriol, a charcoal-dextran absorption is carried out. 250 µl of a charcoal-dextran suspension is fed to each test tube and incubated at 4° C. for 20 minutes. Then, the samples are centrifuged at 10,000 g for 5 minutes at 4° C. The supernatant is decanted and measured in a β-counter after 1 hour of equilibration in Picofluor $_{15}$™.

The competition curves that are obtained at various concentrations of test substance as well as of reference substance (unlabeled calcitriol) at constant concentration of the reference substance ($^3$H-calcitriol) are placed in relation to one another, and a competition factor (KF) is determined.

It is defined as a quotient of the concentrations of the respective test substance and the reference substance, which are necessary for 50% competition:

KF = Concentration of test substance at 50% competition
Concentration of reference substance at 50% competition It is common to the compounds according to the invention that they all have a considerable affinity to the calcitriol receptor.

To determine the acute hypercalcemic action of various calcitriol derivatives, the test that is described below is carried out:

The action of control (solution base), reference substance (1,25-dihydroxy vitamin $D_3$=calcitriol) and test substance is tested in each case after one-time subcutaneous administration in groups of 10 healthy male rats (140–170 g). During the testing time, the rats are kept in special cages to determine the excretion of water and mineral substances. Urine is collected in 2 fractions (0–16 hours and 16–22 hours). An oral dose of calcium (0.1 mmol of calcium in 6.5% alpha-hydroxypropylcellulose, 5 ml/animal) replaces at 1600 hours the calcium intake that is lacking by food deprivation. At the end of the test, the animals are killed by decapitation and exsanguinated to determine the serum-calcium values. For the primary screen test in vivo, an individual standard dose (200 µg/kg) is tested. For selected substances, the result is supported by establishing a dose-effect relation.

A hypercalcemic action is shown in serum-calcium level values that are higher than in the control.

The significance of differences between substance groups and controls and between test substance and reference substance are supported with suitable statistical processes. The result is indicated as dose ratio DR (DR=factor of test substance dose/reference substance dose for comparable actions).

The differentiation-stimulating action of calcitriol analogues is also detected quantitatively.

It is known in the literature [Mangelsdorf, D. J. et al., J. Cell. Biol. 98: 391 (1984)] that the treatment of human leukemia cells (promyelocyte cell line HL 60) in vitro with calcitriol induces the differentiation of cells to macrophages.

HL 60 cells are cultivated in tissue culture medium (RPMI 10% fetal calf serum) at 37° C. in an atmosphere of 5% $CO_2$ in air.

For substance testing, the cells are centrifuged off, and $2.0 \times 10^5$ cells/ml in phenol red-free tissue culture medium is taken up. The test substances are dissolved in ethanol and diluted with tissue culture medium without phenol red to the desired concentration. The dilution stages are mixed with the cell suspension at a ratio of 1:10, and 100 µl each of this cell suspension that is mixed with substance is pipetted into an indentation of a 96-hole plate. For control, a cell suspension is mixed analogously with the solvent.

After incubation for 96 hours at 37° C. in 5% $CO_2$ in air, 100 µl of an NBT-TPA solution (nitro blue tetrazolium (NBT), final concentration in the batch of 1 mg/ml, tetradecanoyl phorbolmyristate-13-acetate (TPA), final concentration in the batch of $2 \times 10^{-7}$ mol/l) is pipetted into each indentation of the 96-hole plate in the cell suspension.

By incubation for 2 hours at 37° C. and 5% $CO_2$ in air, NBT is reduced to insoluble formazan because of the intracellular oxygen radical release, stimulated by TPA, in the cells that are differentiated to macrophages.

To complete the reaction, the indentations of the 96-hole plate are suctioned off, and the cells are affixed to the bottom of the plate by adding methanol and dried after affixing. To dissolve the intracellular formazan crystals that are formed, 100 µl of potassium hydroxide (2 mol/l) and 100 µl of dimethyl sulfoxide are pipetted into each indentation and ultrasonically treated for 1 minute. The concentration of formazan is measured by spectrophotometry at 650 nm.

As a yardstick for the differentiation induction of HL 60 cells to macrophages, the concentration of formed formazan applies. The result is indicated as a dose ratio (DR=factor of test substance dose/reference substance dose for comparable semi-maximum actions).

To determine the metabolic stability, the test substance is incubated with tissue homogenate (from the rat liver) in the presence of buffer systems. The drop in starting concentration is tracked as a function of time. After a certain time, the incubation is stopped, and the unaltered test substance is extracted from the homogenate (diethyl ether), concentrated by evaporation under nitrogen, isolated via HPLC (mobile solvent: acetonitrile/water) and detected using UV-absorption.

The results of the calcitriol-receptor test and the determination of the dose ratio of the differentiation induction of HL 60 cells and the dose ratio for hypercalcemia as well as the half-life in the liver homogenate are summarized below:

Examples of Test Compounds:
(5Z,7E,22E)-(1S,3R)-25-Acetyl-26,27-cyclo-9,10-secocholesta-5,7,10(19),22-tetraene-1,3-diol 66
(5Z,7E,22E)-(1S,3R)-25-(1-oxobutyl)-26,27-cyclo-9,10-secocholesta-5,7,10(19),22-tetraene-1,3-diol 71
(5Z,7E,22E)-(1S,3R)-25-(1-oxopentyl)-26,27-cyclo-9,10-secocholesta-5,7,10(19),22-tetraene-1,3-diol 76
(5Z,7E,22E)-(1S,3R)-25-acetyl-26,27-cyclo-24a-homo-9,10-secocholesta-5,7,10(19),22-tetraene-1,3-diol 126
(5Z,7E)-(1S,3R,22S)-25-acetyl-26,27-cyclo-24a-homo-9,10-secocholesta-5,7,10(19)-triene-1,3,22-triol 127
(5Z,7E,22E)-(1S,3R)-25-(1-oxobutyl)-26,27-cyclo-24a-homo-9,10-secocholesta-5,7,10(19),22-tetraene-1,3-diol 131
(5Z,7E,22E)-(1S,3R)-25-(1-oxopentyl)-26,27-cyclo-24a-homo-9,10-secocholesta-5,7,10(19),22-tetraene-1,3-diol 136
(5Z,7E,22E)-(1S,3R,24S)-25-acetyl-26,27-cyclo-24a,24b-dihomo-9,10-secocholesta-5,7,10(19),22-tetraene-1,3,24-triol 168b
(5Z,7E,22E)-(1S,3R,24S)-25-(1-oxobutyl)-26,27-cyclo-24a,24b-dihomo-9,10-secocholesta-5,7,10(19),22-tetraene-1,3,24-triol 175b
(5Z,7E,22E)-(1S,3R,24S)-25-(1-oxopentyl)-26,27-cyclo-24a,24b-dihomo-9,10-secocholesta-5,7,10(19),22-tetraene-1,3,24 triol 182b
(5Z,7E,22E)-(1S,3R,24S)-25-ethyl-26,27-cyclo-9,10-secocholesta-5,7,10(19),22-tetraene-1,3,24-triol 214a
(5Z,7E,22E)-(1S,3R,24R)-25-ethyl-26,27-cyclo-9,10-secocholesta-5,7,10(19),22-tetraene-1,3,24-triol 214b
[5Z,7E,22E,25(E)]-(1S,3R,24R)-25-(1-butenyl)-26,27-cyclo-9,10-secocholesta-5,7,10(19),22-tetraene-1,3,24-triol 221b
(5Z,7E,22E)-(1S,3R,24S)-25-butyl-26,27-cyclo-9,10-secocholesta-5,7,10(19),22-tetraene-1,3,24,-triol 226a
(5Z,7E,22E)-(1S,3R,24R)-25-butyl-26,27-cyclo-9,10-secocholesta-5,7,10(19),22-tetraene-1,3,24-triol 226b
(5Z,7E,22E)-(1S,3R,24R)-25-hexyl-26,27-cyclo-9,10-secocholesta-5,7,10(19),22-tetraene-1,3,24-triol 231b
(5Z,7E,22E)-(1S,3R,24R)-25-heptyl-26,27-cyclo-9,10-secocholesta-5,7,10(19),22-tetraene-1,3,24-triol 236b
[5Z,7E,22E,25(Z)]-(1S,3R,24S)-25-(1-octenyl)-26,27-cyclo-9,10-secocholesta-5,7,10(19),22-tetraene-1,3,24-triol 246b Comparison Compounds:

Calcitriol
(5Z,7E,22E)-(1S,3R,24S)-26,27-Cyclo-9,10-secocholesta-5,7,10(19),22-tetraene-1,3,24-triol (calcipotriol)

| Compound | KF | DR HL 60 | DR Ca | T½ (min) |
|---|---|---|---|---|
| 66 | 10 | 0.5 | 30 | 110 |
| 71 | 9 | 1.7 | 100 | 120 |
| 76 | 7 | 19 | >100 | >120 |
| 81 | 40 | 9 | >>300 | >120 |
| 126 | 5 | 0.5 | 20 | 120 |
| 127 | 30 | 4 | >100 | 120 |
| 131 | 10 | 0.2 | 30 | 120 |
| 132 | 20 | 2 | >100 | 100 |
| 136 | 10 | 17 | >100 | >120 |
| 168b | 3 | 7 | >100 | 120 |
| 175b | 1 | 3 | >100 | 90 |
| 182b | 2 | 18 | >100 | 100 |
| 214a | 3 | 1.5 | >>1 | 80 |
| 214b | 1 | 0.1 | >1 | 100 |
| 221b | 2 | 0.1 | 10 | 90 |

-continued

| Compound | KF | DR HL 60 | DR Ca | T½ (min) |
|---|---|---|---|---|
| 226a | 4 | 2 | >>1 | 80 |
| 226b | 3 | 0.4 | >5 | 100 |
| 231b | 9 | 2 | >100 | 75 |
| 236b | 20 | 4 | >>30 | 100 |
| 246b | 10 | 2 | >>10 | 100 |
| calcitriol | 1 | 1 | 1 | 120 |
| calcipotriol | 1 | 1 | 50 | 40 |

In addition to an affinity to the vitamin D receptor, which is comparable to that of calcitriol, the compounds listed partially show a likewise comparable or better cell-differentiating activity.

The induction of a hypercalcemia is carried out, however, only at very much higher doses than in the case of calcitriol.

The metabolic stability of the compounds equals that of calcitriol and is considerably higher than that of the structurally related calcipotriol.

Use of the Compounds According to the Invention

By the reduced property of triggering a hypercalcemia as well as the high metabolic stability, the substances according to the invention are suitable in a special way for the production of pharmaceutical agents for the treatment of diseases that are characterized by hyperproliferation and deficient cell differentiation. Included in these are, for example, hyperproliferative diseases of the skin (psoriasis, pityriasis subia pilasis, acne, ichthyosis) and pruritus, as well as tumor diseases and precancerous stages (for example, tumors of the intestines, carcinomas of the breast, lung tumors, prostate carcinomas, leukemias, T-cell lymphomas, melanomas, Batazell Larzin, squamous carcinoma, actinic keratoses, cervix dysplasias, and metastasizing tumors of any type).

Also, for the treatment and prophylaxis of diseases that are characterized by a disequilibrium of the immune system, the substances according to the invention are suitable. These include eczemas and diseases of the atopic Formon series and inflammatory diseases (rheumatoid arthritis, asthma), as well as auto-immune diseases, such as, for example, multiple sclerosis, diabetes mellitus type I, myasthenia gravis, lupus erythematosus, scleroderma, bullous skin diseases (pemphigus, pemphigoid), further rejection reactions in the case of autologous, allogeneic or xenogeneic transplants, as well as AIDS. In all these diseases, the new compounds of general formula I can be combined advantageously with other substances that have an immunosuppressive action, such as cyclosporin A, FK 506, rapamycin and anti-CD 4-antibodies.

The substances are also suitable for therapy of secondary hyperparathyroidism and renal osteodystrophia because of the property of calcitriols to drop the parathormone synthesis.

Owing to the presence of the vitamin D receptor in the insulin-producing cells of the pancreas, the substances are suitable by increasing the insulin secretion for the therapy of diabetes mellitus type II.

Further, it has been found, surprisingly enough, that by topical application of the compounds according to the invention on the skin of mice, rats and guinea pigs, an increased reddening of the skin and increase of the thickness of the epidermis can be induced. The increase in the reddening of the skin is determined based on the increase in the red value of the skin surface that can be quantified with a calorimeter. The red value is typically increased 1.5-fold after the substance (dose 0.003%) is administered three times at intervals of 24 hours. The increase in the thickness of the epidermis is quantified in the histological preparation. It is typically increased 2.5-fold. The number of proliferating epidermal cells (cells in the S-phase of the cell cycle) is determined by flow cytometry and is typically increased by a factor of 6.

These properties of the derivatives in the vitamin D series according to the invention can appear suitable for therapeutic use in the case of atrophic skin, as it occurs in natural skin aging because of increased light exposure or medicinally-induced skin atrophy by treatment with glucocorticoids.

Further, it can be assumed that wound healing can be accelerated by topical application with the new compounds.

In cell populations of the hair follicle, which contribute decisively to hair growth or to hair cycle regulation, it was possible to detect vitamin $D_3$ receptor proteins [Stumpf, W. E. et al., Cell Tissue Res. 238, 489 (1984); Milde, P. et al., J. Invest. Dermatol. 97, 230 (1991)]. In addition, in vitro findings on isolated hair follicle keratinocytes show a proliferation-inhibiting and differentiation-stimulating influence of $1,25\text{-}(OH)_2\text{-}D_3$.

From clinical observations, it is known that the vitamin $D_3$-resistant rickets often accompanies alopecia, which develops in early infancy. Experimental findings show that the vitamin $D_3$ bonding site of the VDR in this disease mutates, i.e., is defective [Kristjansson, K. et al., J. Clin. Invest. 92, 12 (1993)]. Keratinocytes, which were isolated from the hair follicles of these patients, do not react in vitro to the addition of $1,25\text{-}(OH)_2\text{-}D_3$ [Arase, S. et al., J. Dermatol. Science 2, 353 (1991)].

These findings indicate a decisive role for $1,25\text{-}(OH)_2\text{-}D_3$ in the regulation of hair growth.

These analogues are therefore especially suitable for the production of pharmaceutical agents for the treatment of diseases which accompany disrupted hair growth (androgenetic alopecia, alopecia areata/totalis, chemotherapy-induced alopecia) or for supporting physiological hair growth without causing the side-effects of calcitriol (especially hypercalcemia).

Senile and postmenopausal osteoporosis is characterized by an increased bone turnover with an overall negative balance. Owing to the bone shrinkage especially of trabecular bones, fractures result to an increased extent. Owing to the stimulating action of calcitriol, both in the number and the conduct of synthesis of cells forming new bones (osteoblasts), the substances according to the invention are suitable for therapy and prophylaxis of senile and postmenopausal osteoporosis (EP 0 634 173 A1), of steroid-induced osteoporosis as well as for accelerated healing of arthroplasties without causing the side-effects of calcitriol (especially hypercalcemia). For the therapy of various forms of osteoporosis, they can be combined advantageously with estradiol or other derivatives of estrogen.

Finally, it was possible to show that calcitriol increases the synthesis of a growth substance for nerve cells (nerve growth factor) [M. S. Saporito et al. Brain Res. 633, 189 (1994)]. The compounds according to the invention are therefore also suitable for treating degenerative diseases of the peripheral and central nervous system, such as Alzheimer's disease and amyotrophic lateral sclerosis.

In addition, it has been found that certain compounds of general formula I in HL 60 cells antagonize, surprisingly enough, the action of calcitriol (see also WO 94/07853, WO 97/00242).

Such compounds can be used for the therapy of hypercalcemias, such as, for example, in hypervitaminosis D or intoxication with calcitriol and calcitriol-like active substances, or in the case of increased extrarenal calcitriol synthesis in granulomatous diseases (sarcoidosis, tuberculosis). Also, paraneoplastic hypercalcemias (for example, in osteolytic metastases and tumors with increased synthesis of parathormone-related peptides) as well as in hypercalcemias in the case of hyperparathyroidism.

In addition, calcitriol antagonists can be used for birth control. In the reproductive tracts of female and male animals, the vitamin D receptor is expressed. It is known that the female and male fertility of vitamin-D-deficient animals is reduced. By short-term substitution of calcitriol, the reproductive output can be increased. Calcitriol antagonists are therefore able to influence female and male fertility.

Since calcitriol, under certain conditions, shows an immunosuppressive action, calcitriol receptor antagonists can also be used as immunostimulants, e.g., in the case of weak defenses against infections.

Calcitriol is known to be able to modulate hair growth. Calcitriol antagonists can therefore be used therapeutically in the case of undesirable hair growth, e.g., in hirsutism.

Vitamin D has long been known to play a stimulating role in the formation of arteriosclerotic plaque. In such vascular lesions, a calcitriol-regulated protein, osteopontin, is found to be increased, to which a role in vascular sclerosis is attributed [R. Eisenstein et al. Arch. Path. 77, 27 (1964), L. A. Fitzpatrick et al., J. Clin. Invest. 94, 1597 (1994)]. Calcitriol antagonists are therefore suitable for therapy and prophylaxis of all types of arteriosclerosis.

Finally, calcitriol antagonists are suitable because of the property of calcitriol to increase unspecific immune reactions of monocytic cells, for therapy of inflammatory diseases, especially of a chronic nature, such as rheumatoid arthritis, Crohn's disease, ulcerative colitis, and granulomatous diseases such as sarcoidosis and other foreign-body reactions.

For all listed therapeutic applications, it is true that the compounds according to the invention are able to achieve a therapeutic action in the above-mentioned clinical pictures without causing the side-effects of calcitriol (especially hypercalcemia).

This invention thus relates to pharmaceutical preparations that contain at least one compound according to general formula I together with a pharmaceutically compatible vehicle.

The compounds can be formulated as solutions in pharmaceutically compatible solvents or as emulsions, suspensions or dispersions in suitable pharmaceutical solvents or vehicles or as pills, tablets or capsules, which contain solid vehicles in a way known in the art. For topical use, the compounds are advantageously formulated as creams or ointments or in a similar form of pharmaceutical agent that is suitable for topical use. Each such formulation can also contain other pharmaceutically compatible and nontoxic adjuvants, such as, e.g., stabilizers, antioxidants, binders, dyes, emulsifiers or flavoring additives.

The compounds are advantageously administered by injection, intravenous infusion of suitable sterile solutions, as an aerosol via bronchial tubes and lungs, or as oral dosage via the alimentary tract or topically in the form of creams, ointments, lotions or suitable transdermal patches, as is described in EP-A 0 387 077.

The daily dose is approximately 0.1 µg/patient/day-1000 µg/patient/day, preferably 1.0 µg/patient/day-500 µg/patient/day.

Process for the Production of the Compounds According to the Invention

The production of the vitamin D derivatives of general formula I is carried out according to the invention from a compound of general formula II,

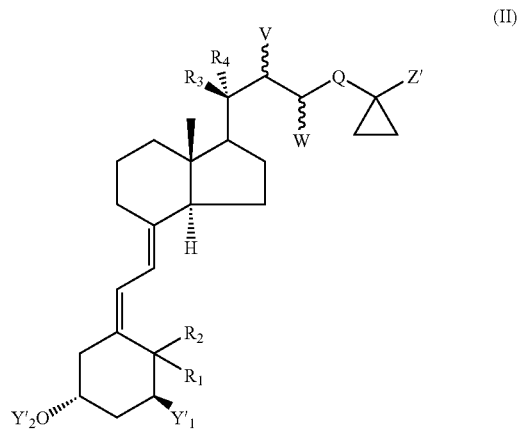

(II)

in which $Y'_1$ means a hydrogen atom, a halogen atom or a protected hydroxyl group and $Y'_2$ means a hydroxy protective group.

Z' is distinguished from Z in that optionally present hydroxyl groups or keto groups can be present in protected form.

The protective groups are preferably alkyl-, aryl- or mixed alkylaryl-substituted silyl groups, e.g., the trimethylsilyl (TMS), triethylsilyl (TES), tert-butyldimethylsilyl (TBDMS), tert-butyldiphenylsilyl (TBDPS) or triisopropylsilyl (TIPS) groups or another standard hydroxy protective group (methoxymethyl, methoxyethoxymethyl, ethoxyethyl, tetrahydrofuranyl and tetrahydropyranyl groups); for the keto groups, these are preferably ketals (1,3-dioxolans, 1,3-dioxanes, dialkoxyketals) (see T. W. Greene, P. G. M. Wuts "Protective Groups in Organic Synthesis," $2^{nd}$ Edition, John Wiley & Sons, 1991).

By simultaneous or successive cleavage of the hydroxy and keto protective groups and optionally by partial, successive or complete esterification of the free hydroxyl groups, II is converted into a compound of general formula I.

In the case of the silyl protective groups or the trimethylsilylethoxymethyl group, tetrabutylammonium fluoride, hydrofluoric acid or hydrofluoric acid/pyridine or acidic ion exchanger is used for their cleavage; in the case of the ether groups (methoxymethyl, methoxyethoxymethyl, ethoxyethyl, tetrahydropyranyl ether) and ketals, the latter are cleaved off under catalytic action of acid, for example, p-toluenesulfonic acid, pyridinium-p-toluenesulfonate, acetic acid, hydrochloric acid, phosphoric acid or an acidic ion exchanger.

The esterification of the free hydroxy groups can be carried out according to standard processes with the corresponding carboxylic acid chlorides, -bromides or -anhydrides.

The production of the starting compounds for general formula II starts from various starting compounds depending on the ultimately desired substitution pattern in 10- and 20-position.

For the production of compounds of general formula II, in which $R_1$ and $R_2$ together mean an exocyclic methylene group and $Y'_1$ means a hydrogen atom or a protected hydroxyl group and $Y'_2$ means a hydroxy protective group, a start is made from known aldehyde III (M. Calverley Tetrahedron 43, 4609 (1987), WO 87/00834).

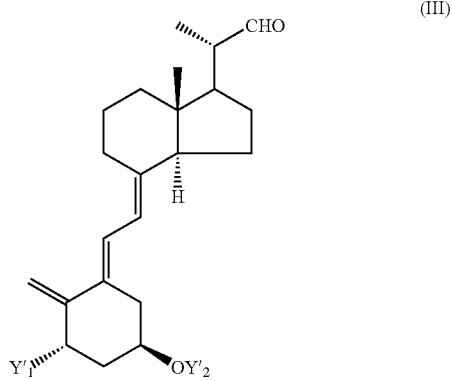
(III)

For $Y'_1$ and $Y'_2$, protective groups other than those mentioned in the bibliographic references can be obtained by analogous procedure using correspondingly modified silyl chlorides (e.g., tert-butyldiphenylsilyl chloride instead of tert-butyldimethylsilyl chloride). By foregoing the corresponding stages for 1α-hydroxylation, derivatives of $Y'_1$=H type can be obtained.

The compounds of general formula III are now converted, analogously to known processes, into aldehydes of general formula IV [EP 647 219, WO 94/07853, M. J. Calverley, L. Binderup Bioorg. Med. Chem. Lett. 3, 1845–1848 (1993)].

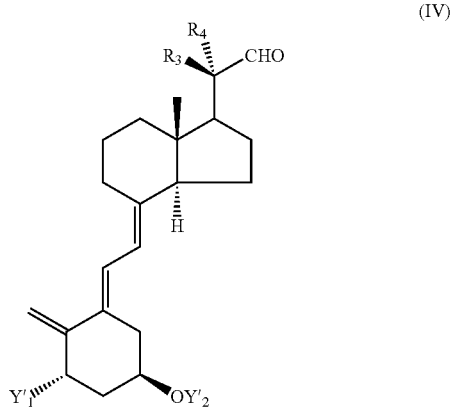
(IV)

For $R_3$ and $R_4$, the definitions that are already mentioned above apply.

To establish the natural vitamin D-triene system, a photochemical isomerization of the compounds of general formula IV is performed. Irradiation with ultraviolet light is carried out in the presence of a so-called triplet sensitizer. Within the scope of this invention, anthracene is used in this respect. By cleavage of the π-bond of the 5,6-double bond, rotation of the A ring by 180° around the 5,6-single bond and reestablishing the 5,6-double bond, the stereoisomerism on the 5,6-double bond is reversed, whereby compounds of general formula V accumulate,

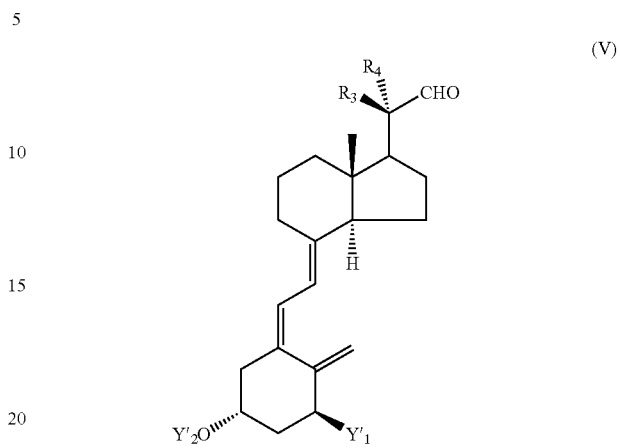
(V)

In principle, this isomerization reaction is also possible in a later stage. By way of example, the reactions of aldehyde VI with natural configuration at C-20 are described below.

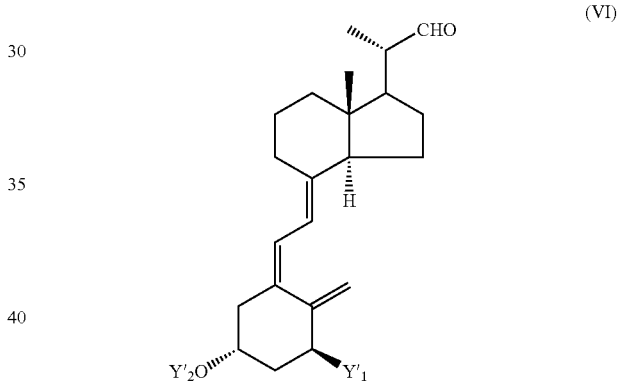
(VI)

In principle, however, the following reactions are also possible with the above-mentioned substitution models at C-20.

First, the synthesis of compounds, which represent a special case of general formula II, is described. $R_1$ and $R_2$ thus form together a methylene group, $R_3$ is a hydrogen atom and $R_4$ is a methyl group, Q is a methylene group and Z' means a straight-chain 1-oxoalkyl group with 1–12 carbon atoms, in which the keto group is protected (e.g., ketal: dialkoxyketal, 1,3-dioxolan, 1,3-dioxane, 5,5-dimethyl-1,3-dioxane).

Starting material for the side-chain fragments is an acetoacetic acid ester of general formula VII.

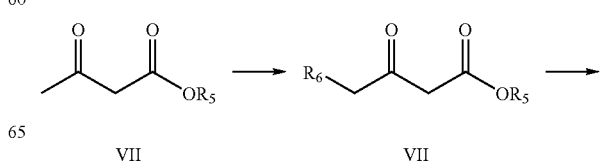
VII          VII

-continued

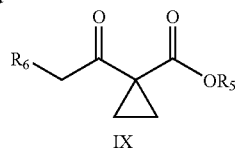

IX

R$_5$ can be a straight-chain or branched alkyl group with up to 6 carbon atoms (preferably methyl or ethyl group). To create longer chains, compound VII is double-deprotonated with two equivalents of one or two different bases (e.g., lithium diisopropylamide, n-butyllithium, sodium hydride, potassium hydride) and then alkylated with an equivalent of an alkyl halide (bromide or iodide) at the reactive position, whereby the compound of general formula VIII accumulates [L. Weiler et al. J. Am. Chem. Soc. 96, 1082–1087 (1974), N. Haddad et al. J. Org. Chem. 60, 6883–6887 (1995), D. F. Taber et al. J. Org. Chem. 60, 2283–2285 (1995)]. R$_6$ means a straight-chain or branched alkyl group with up to 11 carbon atoms.

Compounds VII or VIII are now reacted with a base (e.g., potassium carbonate, sodium carbonate, potassium alcoholate) and 1,2-dibromoethane, whereby compounds of general formula IX are produced. R$_6$ has the meaning already mentioned or is a hydrogen atom [D. F. Taber et al. J. Org. Chem. 57, 436–441 (1992)].

The keto group of compound IX is now converted into a ketal under standard conditions, whereby compound X is produced, in which K means a keto protective group. As keto protective groups, all in "Protective Groups in Organic Synthesis," 2nd Edition, John Wiley & Sons, 1991 (T. W. Greene, P. G. M. Wuts) are suitable (e.g., 1,3-dioxolan, 1,3-dioxane, 5,5-dimethyl-1,3-dioxane, dialkoxyketals). By way of example, 1,3-dioxolan derivative X (K=—O—CH$_2$—CH$_2$—O—) is described below. The use of other ketal groups is, however, possible in principle.

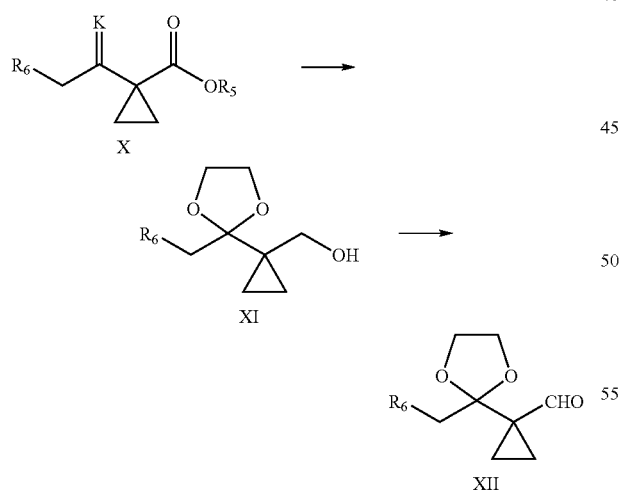

Reduction of the ester unit to alcohol XI can be carried out with a standard reducing agent (e.g., lithium aluminum hydride, diisobutylaluminum hydride). Subsequent oxidation under the usual conditions (manganese dioxide, pyridinium chlorochromate, pyridinium dichromate, Swern conditions) yields aldehyde XII as an important intermediate product (depicted in the drawing as a 1,3-dioxolan derivative, not limited to this protective group, but rather also can be produced with other keto protective groups, see above). In a Wittig reaction with the ylide of methyltriphenylphosphonium iodide or bromide (deprotonation with, e.g., n-butyllithium), olefin XIII is generated.

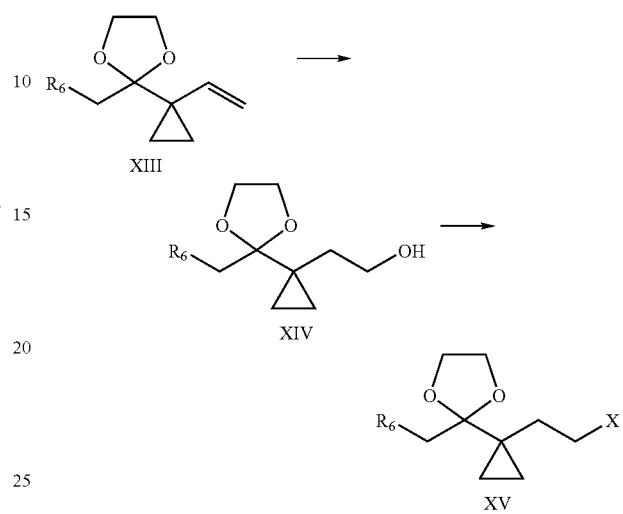

The double bond can now be hydroborated under standard conditions and converted into alcohol XIV after oxidative working-up [Pelter, Smith, Brown, Borane Reagents; Academic Press: New York, 1988; H. C. Browm et al. Heterocycles 25, 641–567 (1987).] The alcohol function is now tosylated (XV, X=OTos) and reacted with the thiophenolate anion to thioether XV (X=SPh). Oxidation (e.g., with hydrogen peroxide, metachloroperbenzoic acid, tert-butylhydroperoxide, sodium periodate) then yields sulfone XV (X=SO$_2$Ph) [P. C. Bulman Page et al. Synth. Comm. 23, 1507–1514 (1993)].

Sulfone XV is now deprotonated with a base (e.g., n-butyllithium, lithium diisopropylamide, sodium hydride, potassium hydride) and reacted at low temperature (between −100° C. and −20° C.) with aldehyde VI, whereby hydroxysulfones of general formula XVI (X=SO$_2$Ph) accumulate.

(XVI)

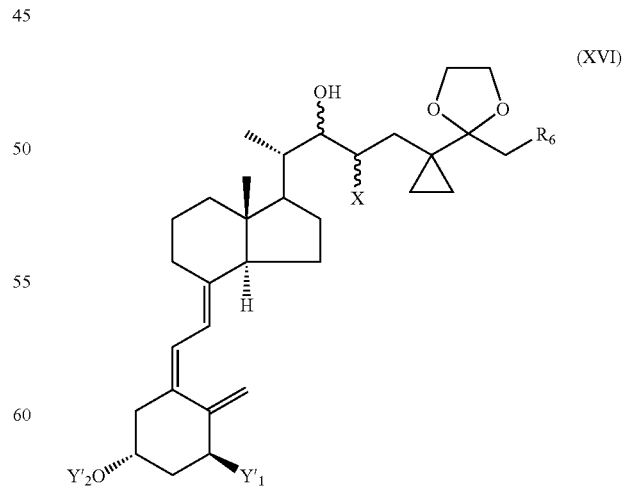

Conversion of the hydroxysulfones into compounds that carry a double bond in the side chain is possible in the case of vitamin D derivatives, preferably by reaction with a sodium amalgam (H. F. DeLuca et al. Bioorg. Chem. 15, 152–166 (1987), H. F. DeLuca et al. Biochemistry 29, 190–196 (1990)].

(XVII)

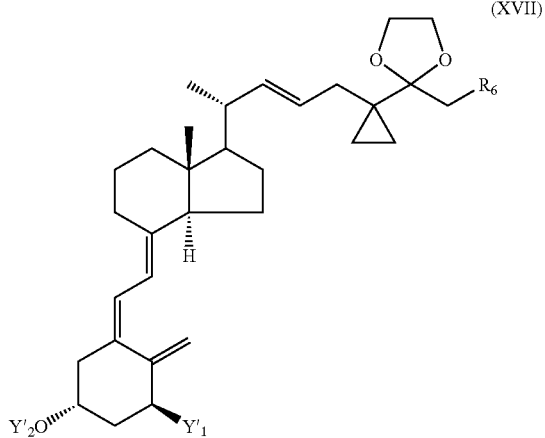

(XVIII)

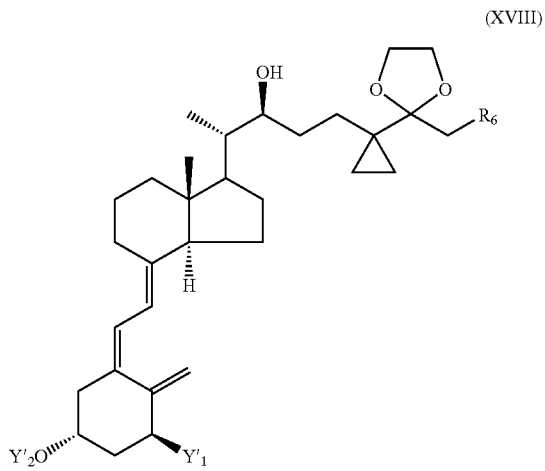

In addition to the olefins of general formula XVII, the alcohols of general formula XVIII, which are separated by chromatography, also accumulate.

The compounds of general formulas XVII and XVIII can be regarded as special cases of general formula II and can be converted into the title compounds of general formula I as described above.

Below, the synthesis of compounds that represent another special case of general formula II is described. $R_1$ and $R_2$ together thus form a methylene group, $R_3$ is a hydrogen atom, and $R_4$ is a methyl group, Q is an ethylene group and Z' has the definition already mentioned above.

To create the side-chain fragments, aldehydes of general formula XII are reacted in the Horner-Wadsworth-Emmons reactions with deprotonated phosphonoacetic acid esters (base: e.g., lithium diisopropylamide, n-butyllithium, sodium hydride, potassium hydride), whereby esters of general formula XIX accumulate.

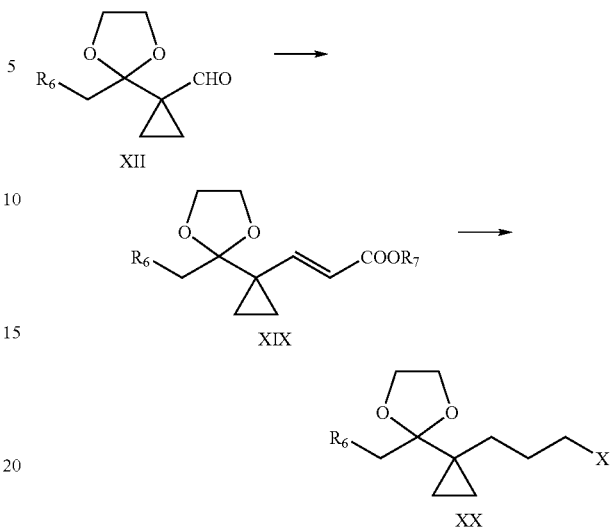

Reduction under Birch conditions (lithium, sodium or calcium in liquid ammonia or amines) yields the alcohols of general formula XX (X=OH).

The alcohol group is now tosylated (XX, X=OTos) and reacted with the thiophenolate anion to thioether XX (X=SPh). Oxidation (e.g., with hydrogen peroxide, metachloroperbenzoic acid, tert-butylhydroperoxide, sodium periodate) then yields sulfone XX (X=SO$_2$Ph) [P. C. Bulman Page et al. Synth. Comm. 23, 1057–1514 (1993)].

Sulfone XX is now deprotonated with a base (e.g., n-butyllithium, lithium diisopropylamide, sodium hydride, potassium hydride) and reacted at low temperature (between $-100°$ C. and $-20°$ C.) with aldehyde VI, whereby hydroxysulfones of general formula XXI (X=SO$_2$Ph) accumulate.

(XXI)

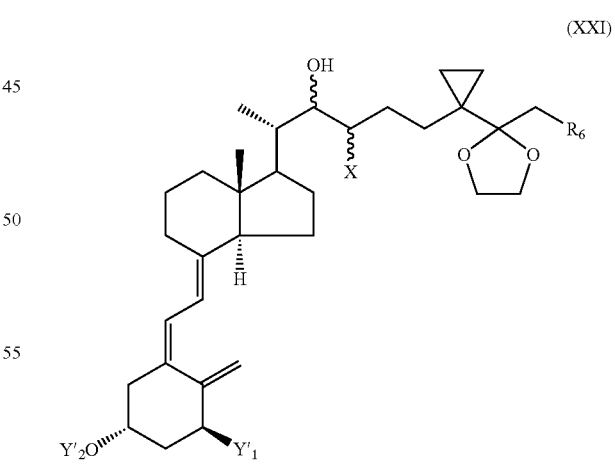

Conversion of the hydroxysulfones into compounds that carry a double bond in the side chain is possible in the case of vitamin D derivatives, preferably by reaction with a sodium amalgam (H. F. DeLuca et al. Bioorg. Chem. 15, 152–166 (1987), H. F. DeLuca et al. Biochemistry 29, 190–196 (1990)].

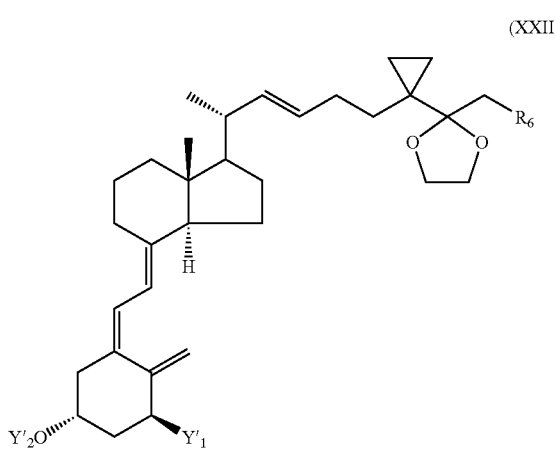

(XXII)

(XXIII)

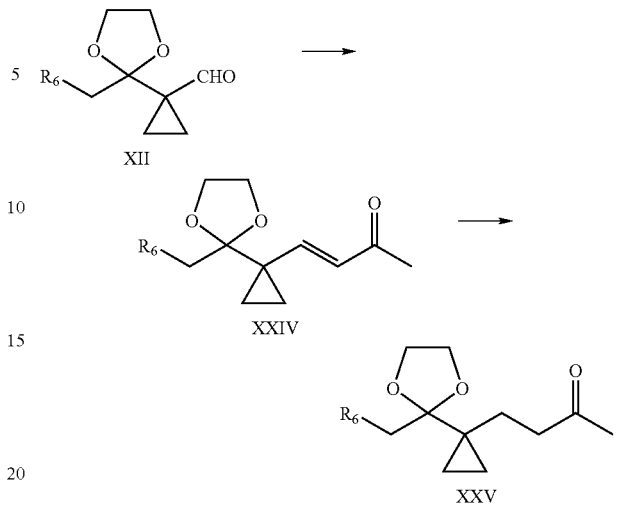

In addition to the olefins of general formula XXII, the alcohols of general formula XXIII, which are separated by chromatography, also accumulate.

The compounds of general formulas XXII and XXIII can be regarded as special cases of general formula II and can be converted into the title compounds of general formula I as described above.

Below, the synthesis of compounds that represent another special case of general formula II is described. $R_1$ and $R_2$ together thus form a methylene group, $R_3$ is a hydrogen atom and $R_4$ is a methyl group, Q means —CH(OH)—CH$_2$—CH$_2$—, and Z' has the meaning already mentioned above.

In this case, the aldehyde of general formula XII is converted with oxopropylphosphonic acid dialkyl ester in the presence of a base (triethylamine, ethyldiisopropylamine, triisopropylamine, diazabicyclononane, diazabicycloundecane, sodium hydride) with the optional addition of lithium chloride into ketone XXIV [S. Masamune et al. Tetrahedron Lett. 25, 2183–2186 (1984), B. Resul et al. J. Med. Chem. 36, 243–248 (1993)].

Reaction to form saturated ketones of general formula XXV can be carried out by Birch reduction (described above) optionally followed by reoxidation (e.g., with pyridinium dichromate, pyridinium chlorochromate, Swern conditions) or by hydrogenation of the double bond. To avoid hydrogenolytic cleavage of the cyclopropyl ring, platinum (VI) oxide or a soluble rhodium catalyst (e.g., Wilkinson's catalyst) should be used as a catalyst.

Ketones XXV are regioselectively deprotonated with a base (e.g., lithium diisopropylamide, lithium or sodium hexamethyl disilazide) and reacted at low temperature with the aldehyde of general formula VI, whereby compounds of general formula XXVI (X=OH) accumulate.

(XXVI)

The hydroxyl group is then converted into a leaving group under standard conditions, whereby compounds of general formula XXVI (X=e.g., acetate, trifluoroacetate, tosylate, mesylate or triflate) are produced.

Elimination with the aid of bases (e.g., diazabicyclononane, diazabicycloundecane, triethylamine, diisopropylamine, ethyldiisopropylamine) at optionally increased reaction temperatures yields the ketones of general formula XXVII.

(XXVII)

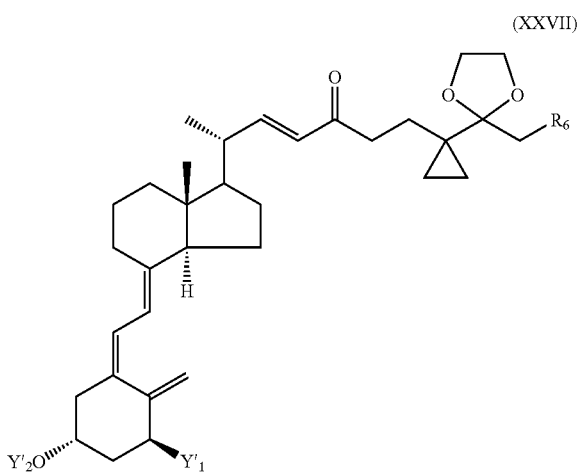

The carbonyl groups in XXVII can now be reduced to diastereomeric alcohols XXVIII (reducing agent: e.g., sodium borohydride/cerium trichloride, lithium aluminum hydride, diisobutylaluminum hydride, lithium borohydride) and are separated by chromatography.

(XXVIII)

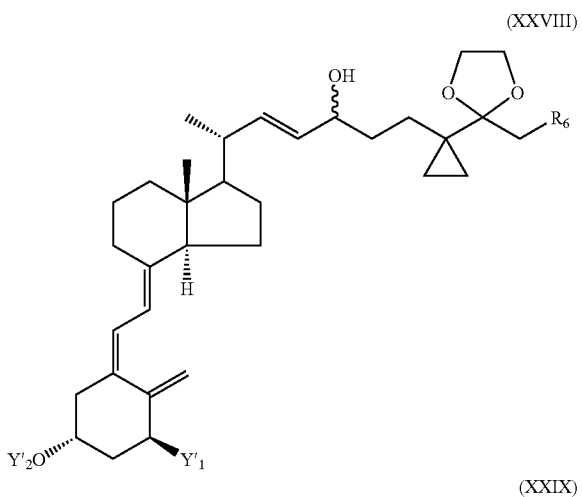

(XXIX)

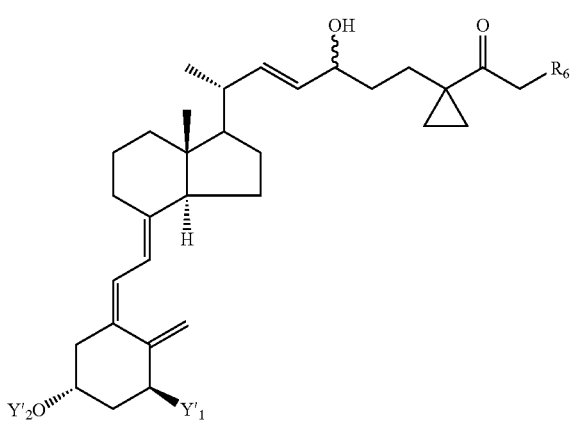

The cleavage of the protective groups at the compound of general formula XXVIII, which is to be viewed as a special case of general formula II, should be carried out in a successive manner. The ketal is cleaved off by mild acid reaction conditions (e.g., pyridinium-p-toluenesulfonate, oxalic acid/silica gel), whereby compounds of general formula XXIX accumulate. As described, compounds of general formula I are then obtained.

Below, the synthesis of compounds that represent another special case of general formula II is described. $R_1$ and $R_2$ together thus form a methylene group, $R_3$ is a hydrogen atom and $R_4$ is a methyl group, Q means —CH(OH)—, and Z' means an alkyl or alkenyl group with 1–12 carbon atoms.

The aldehyde of general formula XII, if $R_6$ is a hydrogen atom, is reacted with alkyltriphenylphosphonium salts in the presence of bases (e.g., n-butyllithium, sodium hydride, potassium hydride) in Wittig reactions, whereby compounds of general formula XXX accumulate. $R_7$ means a straight-chain or branched alkyl or alkenyl group with 1–10 carbon atoms. Double-bond E,Z-mixtures usually occur. Chromatographic separation of isomers is carried out only at a later stage.

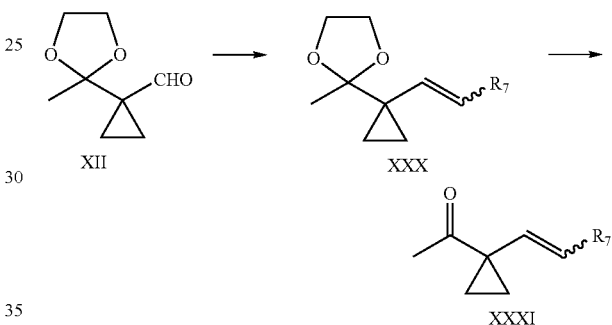

The cleavage of the ketal unit is carried out under acidic reaction conditions (e.g., hydrochloric acid, acetone; p-toluenesulfonic acid, methanol; oxalic acid, silica gel), whereby compounds of general formula XXXI are obtained.

Ketones XXXI are deprotonated with a base (e.g., lithium diisopropylamide, lithium or sodium hexamethyldisilazide) and reacted at low temperature with the aldehyde of general formula VI, whereby compounds of general formula XXXII (X=OH) accumulate.

(XXXII)

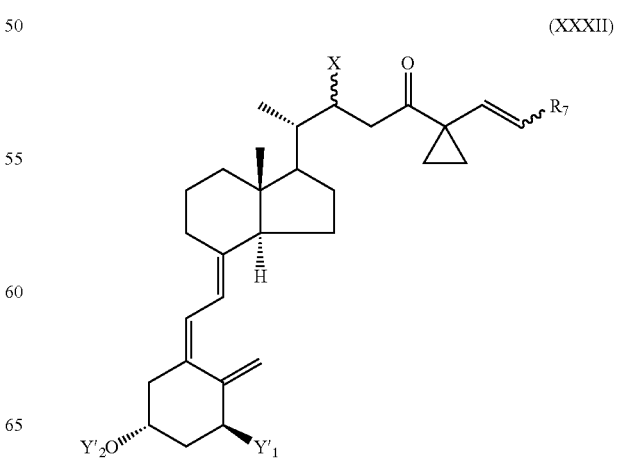

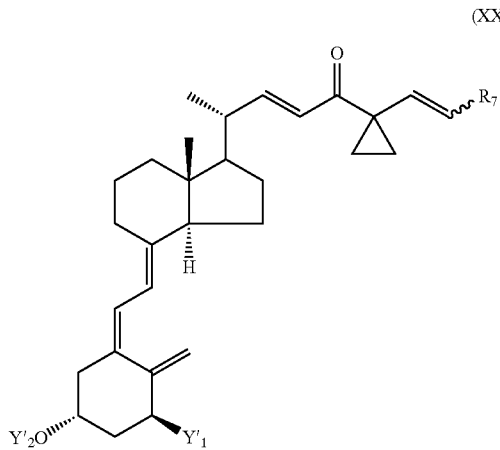

(XXXIII)

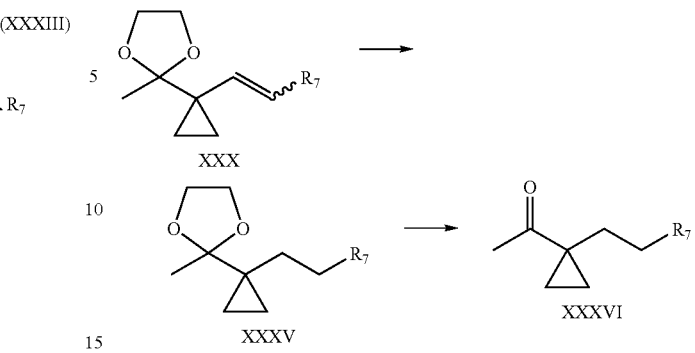

The cleavage of the ketal to form ketone XXXVI and the linkage to the vitamin D skeleton are carried out as described above, so that finally a compound of general formula XXXVII that is to be regarded as a special case of general formula II is produced.

The hydroxyl group is then converted under standard conditions into a leaving group, whereby compounds of general formula XXXII (X=e.g., acetate, trifluoroacetate, tosylate, mesylate or triflate) are produced.

Elimination with the aid of bases (e.g., diazabicyclononane, diazabicycloundecane, triethylamine, diisopropylamine, ethyldiisopropylamine) at optionally higher reaction temperatures yields the ketones of general formula XXXIII.

The carbonyl groups in XXXIII can now be reduced to the diastereomeric alcohols XXXIV (reducing agent: e.g., sodium borohydride/cerium trichloride, lithium aluminum hydride, diisobutylaluminum hydride, lithium borohydride) and are separated by chromatography.

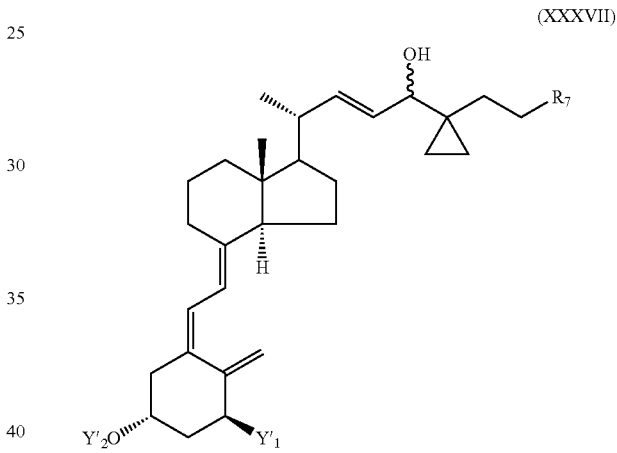

(XXXVII)

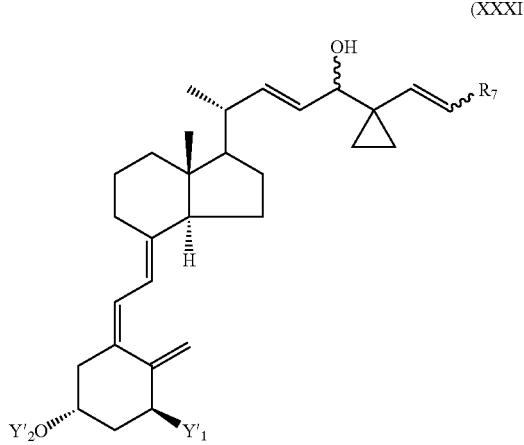

(XXXIV)

The conversion into a compound of general formula I is carried out as described.

For synthesis of compounds of general formula II for which $R_1$ and $R_2$ are hydrogen atoms, a convergent synthesis method must be employed, in which CD- and A-ring fragments are synthesized separately. For synthesis of the CD-fragments, aldehyde XXXVIII that is known in the literature [H. H. Inhoffen et al. Chem. Ber. 92, 781–791 (1958); H. H. Inhoffen et al. Chem. Ber. 92, 1772–1788 (1959); W. G. Dauben et al., Tetrahedron Lett. 30, 677–680 )] is used,

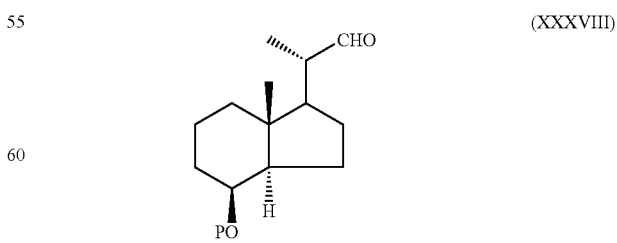

(XXXVIII)

The compound of general formula XXXIV can be regarded as a special case of general formula II and is converted, as described, into the compound of general formula I.

In addition, the double bond of the compound of general formula XXX can be hydrogenated, whereby a compound of general formula XXXV accumulates. As catalysts, soluble rhodium catalysts (Wilkinson's catalyst) or platinum(VI) oxide are to be preferred here.

in which P means an acyl-, alkyl- or aryl-substituted silyl group, or a tetrahydropyranyl, tetrahydrofuranyl, methoxymethyl or ethoxyethyl group, an acyl group (e.g., acetyl or benzoyl group) or another hydroxy protective group (see T. W. Greene, P. G. M. Wuts Protective Groups in organic Synthesis, 2$^{nd}$ Edition, John Wiley and Sons, Inc. 1991).

According to the known processes, the already described modifications at C-20 can be introduced here (WO 94/07853), whereby a compound of general formula XXXIX accumulates.

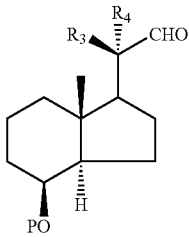
(XXXIX)

The introduction of the side chains is carried out here analogously to the case of vitamin D-aldehyde XII, whereby compounds of general formula XL are obtained.

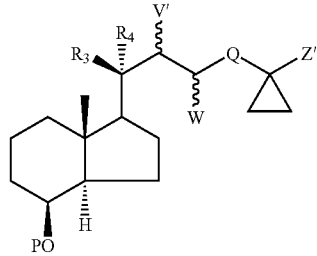
(XL)

V' means a protected hydroxyl group or together with W an E-double bond. The other variables were already defined previously.

In the selection of suitable protective groups (e.g., P=triethylsilyl, V'=tetrahydropyranoxy), P is selectively cleaved off (e.g., with tetrabutylammonium fluoride), whereby the compound of general formula XLI accumulates.

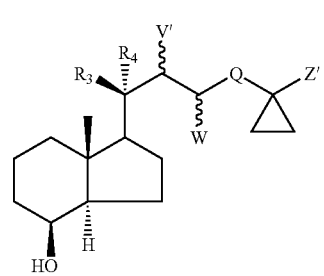
XLI

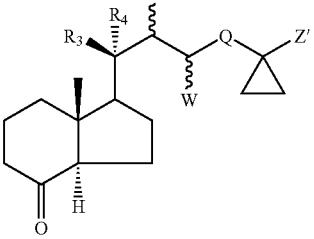
XLII

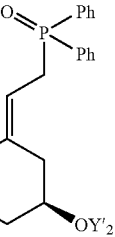
XLIII

Oxidation according to known methods (e.g., pyridinium chlorochromate, pyridinium dichromate, Swern conditions) produces a compound of general formula XLII, which by reaction with the anion, produced by a base (e.g., lithium diisopropylamide, n-butyllithium), of the phosphine oxide of general formula XLIII known in the literature [H. F. DeLuca et al. Tetrahedron Lett. 32, 7663–7666 (1991)], in which Y'$_2$ has the already described meaning, is converted into corresponding compounds of general formula II for which the following is true: Y'$_1$=OY'$_2$. Further reaction to form the compound of general formula I is carried out as already described.

The following examples are used for a more detailed explanation of the invention.

Synthesis of the Starting Compounds in the 24-Methylene Series 1. (5Z,7E)-(1S,3R)-1,3-Bis[[dimethyl(1,1-dimethylethyl)-silyl]-oxy]-9,10-secopregna-5,7,10(19)-triene-20-carbaldehyde 2

7.5 g of (5E,7E)-(1S,3R)-1,3-bis[[dimethyl(1,1-dimethylethyl)silyl]oxy]-9,10-secopregna-5,7,10(19)-triene-20-carbaldehyde 1 [M. J. Calverley Tetrahedron 43, 4609–4619 (1987)] is dissolved in 200 ml of toluene, 2 g of anthracene and 0.5 ml of triethylamine are added and irradiated while nitrogen is passing through it in a Pyrex apparatus with a high-pressure mercury-vapor lamp for 30 minutes. Then, it is filtered, concentrated by evaporation, and the residue is chromatographed on silica gel with ethyl acetate/hexane, whereby 7.1 g of title compound 2 is obtained as a colorless foam.

$^1$H-NMR (300 MHz, CDCl$_3$): δ=0.05 ppm (s, 12H); 0.55 (s, 3H); 0.88 (s, 18H); 1.11 (d, 3H); 2.37 (m, 1H); 4.18 (m, 1H); 4.37 (m, 1H); 4.84 (brs, 1H); 5.17 (brs, 1H); 6.00 (d, 1H); 6.22 (d, 1H); 9.58 (d, 1H)

2. 1-Acetylcyclopropanecarboxylic acid methyl ester 4

56 g of acetoacetic acid methyl ester 3 is dissolved in 500 ml of acetone, and 276.2 g of potassium carbonate as well as 86 ml of dibromoethane are added while being cooled with ice. It is heated under nitrogen to 50° C. and stirred for 72 hours at this temperature. After cooling, the mixture is diluted with ethyl acetate, washed with water and saturated sodium chloride solution, dried on sodium sulfate and concentrated by evaporation. The residue is distilled in a vacuum, whereby 66 g of the title compound is obtained as a colorless oil.

$^1$H-NMR (300 MHz, CDCl$_3$): δ=1.48 ppm (s, 4H); 2.47 (s, 3H); 3.74 (s, 3H)

3. 1-(2-Methyl-1,3-dioxolan-2-yl)cyclopropanecarboxylic acid methyl ester 5

18.7 g of 4 is dissolved in 500 ml of benzene, 30 ml of ethylene glycol and 1 g of p-toluenesulfonic acid are added and heated under nitrogen in a water separator for 12 hours. After cooling, sodium bicarbonate solution is added, extracted with ethyl acetate, dried on sodium sulfate and concentrated by evaporation, whereby 23 g of title compound 5 accumulates as a colorless oil.

$^1$H-NMR (300 MHz, CDCl$_3$): δ=1.02 ppm (m, 2H); 1.16 (m, 2H); 1.61 (s, 3H); 3.69 (s, 3H); 3.92 (m, 4H)

4. 1-(2-Methyl-1,3-dioxolan-2-yl)cyclopropane methanol 6

11.2 g of 5 is dissolved in 150 ml of toluene and cooled under nitrogen to 0° C. 125 ml of DIBAH solution (1.2 M in toluene) is now slowly added in drops and stirred for 2 more hours. Then, 1.25 ml of isopropanol and 25 ml of water are added in drops and stirred overnight. The precipitate is filtered off, the filtrate is concentrated by evaporation and chromatographed on silica gel with ethyl acetate/hexane, whereby 9.1 of title compound 6 accumulates as a colorless oil.

$^1$H-NMR (300 MHz, CDCl$_3$): δ=0.47 ppm (m, 2H); 0.72 (m, 2H); 1.41 (s, 3H); 2.92 (t, OH); 3.53 (d, 2H); 3.97 (m, 4H)

5. 1-(2-Methyl-1,3-dioxolan-2-yl)cyclopropanecarbaldehyde 7

10 g of 6 is dissolved in 500 ml of dichloromethane, and 3.7 g of sodium acetate and 19.3 g of pyridinium chlorochromate are added at room temperature under nitrogen. After 3 hours at room temperature, it is filtered on silica gel, concentrated by evaporation, diluted with diethyl ether, filtered again, and the solvent is removed, whereby 7.8 g of title compound 7 is obtained as a colorless oil.

$^1$H-NMR (300 MHz, CDCl$_3$): δ=1.16 ppm (m, 4H); 1.57 (s, 3H); 3.97 (m, 3H); 9.49 (s, 1H)

6. 2-(1-Ethenylcyclopropyl)-2-methyl-1,3-dioxolan 8

44.6 g of methyltriphenylphosphonium bromide in 700 ml of diethyl ether is introduced, and 50 ml of n-butyllithium solution (2.5 M in hexane) is added in drops at 0° C. under nitrogen. It is stirred for 1 more hour at room temperature and then 9.5 g of 7 in 10 ml of diethyl ether is added. After 1 hour, the reaction solution is quenched with sodium chloride solution, extracted with ethyl acetate, washed with sodium chloride solution, dried on sodium sulfate, and the solvent is removed. The residue is chromatographed on silica gel with ethyl acetate/hexane, whereby 5.4 g of title compound 8 is obtained as a colorless oil.

$^1$H-NMR (300 MHZ, CDCl$_3$): δ=0.59 ppm (m, 2H); 0.86 (m, 2H); 1.41 (s, 3H); 3.95 (m, 4H); 4.98 (d, 1H); 4.99 (d, 1H); 6.21 (dd, 1H)

7. 1-(2-Methyl-1,3-dioxolan-2-yl)cyclopropanethanol 9

5.4 g of 8 is dissolved in 200 ml of tetrahydrofuran (THF), and 14 ml of borane-THF solution (1.0 M in THF) is added in drops at 0° C. under nitrogen. The reaction mixture is then allowed to reach room temperature, and it is stirred for 2 more hours. After cooling was again performed at 0° C., 17 ml of water, 17 ml of aqueous sodium hydroxide solution (25%) and 2 ml of hydrogen peroxide (30%) are added in succession and stirred for 1 more hour. Then, sodium thiosulfate solution is added, extracted with ethyl acetate, washed with sodium chloride solution, dried on sodium sulfate and concentrated by evaporation. The residue is chromatographed on silica gel with ethyl acetate/hexane, whereby 3.9 g of title compound 9 is obtained as a colorless oil.

$^1$H-NMR (300 MHz, CDCl$_3$): δ=0.29 ppm (m, 2H); 0.73 (m, 2H); 1.43 (s, 3H); 1.63 (t, 2H); 3.52 (t, OH); 3.79 (q, 2H); 3.93 (m, 4H)

8. 4-Methylbenzenesulfonic acid 2-[1-(2-methyl-1,3-dioxolan-2-yl)cyclopropyl]ethyl ester 10

470 mg of 9 is dissolved in 10 ml of pyridine, and p-toluenesulfonyl chloride is added at 0° C. under nitrogen. It is stirred for 1 hour at 0° C., and then sodium bicarbonate solution is added. It is extracted with ethyl acetate, washed with dilute hydrochloric acid and then with sodium bicarbonate solution, dried on sodium sulfate and concentrated by evaporation. After the residue is chromatographed on silica gel with ethyl acetate/hexane, 670 mg of the title compound remains as a colorless oil.

$^1$H-NMR (300 MHz, CDCl$_3$): δ=0.27 ppm (m, 2H); 0.61 (m, 2H); 1.29 (s, 3H); 1.78 (t, 2H); 2.46 (s, 3H); 3.80 (m, 4H); 4.23 (t, 2H); 7.35 (d, 2H); 7.81 (d, 2H)

9. 2-Methyl-2-[1-[2-(phenylsulfanyl)ethyl]cyclopropyl]-1,3-dioxolan 11

590 mg of 10 is dissolved in 2 ml of dimethylformamide (DMF) and added under nitrogen to a mixture of 300 mg of potassium-t-butylate and 0.27 ml of thiophenol in 5 ml of DMF. It is stirred for 1 hour at room temperature and then quenched with sodium chloride solution. It is extracted with ethyl acetate, washed with sodium bicarbonate solution and sodium chloride solution, dried on sodium sulfate, concentrated by evaporation, and the residue is chromatographed on silica gel with ethyl acetate/hexane, whereby 630 mg of title compound 11 accumulates as a yellowish oil.

$^1$H-NMR (300 MHz, CDCl$_3$): δ=0.29 ppm (m, 2H); 0.68 (m, 2H); 1.38 (s, 3H); 1.75 (t, 2H); 3.10 (m, 2H); 3.92 (m, 4H); 7.28 (d, 5H)

10. 2-Methyl-2-[1-[2-(phenylsulfonyl)ethyl]cyclopropyl]-1,3-dioxolan 12

480 mg of 11 is dissolved in 18 ml of methanol, and 180 mg of potassium carbonate, 221 mg of acetonitrile and 612 mg of hydrogen peroxide are added under nitrogen and stirred for 6 hours at room temperature. Sodium thiosulfate solution is now added, extracted with ethyl acetate, washed with sodium chloride solution, dried on sodium sulfate, concentrated by evaporation, and the residue is chromatographed on silica gel with ethyl acetate/hexane, whereby 380 mg of title compound 12 is obtained as a colorless oil.

$^1$H-NMR (300 MHz, CDCl$_3$): δ=0.25 ppm (m, 2H); 0.68 (m, 2H); 1.23 (s, 3H); 1.78 (m, 2H); 3.39 (m, 2H); 3.82 (m, 4H); 7.57 (t, 2H); 7.66 (t, 1H); 7.90 (d, 2H)

11. 3-Oxohexanoic acid methyl ester 13

44.4 g of sodium hydride suspension (60% in paraffin oil) is introduced into 1500 ml of THF, and 107.5 ml of acetoacetic acid methyl ester 3 is added under nitrogen at 0° C. After 10 minutes, 440 ml of n-butyllithium solution (2.5 M in hexane) is then added in drops, and it is stirred for another 30 minutes at $_0$C. Now, 88.9 ml of iodoethane is added, and it is stirred overnight at room temperature. For working-up, it is again cooled to 0° C. and neutralized with 4N hydrochloric acid. The organic phase is diluted with ethyl acetate, washed with thiosulfate solution and sodium chloride solution, dried on sodium sulfate and concentrated by evaporation. The residue is then chromatographed on silica gel with ethyl acetate/hexane, whereby 95.13 g of title compound 13 is obtained as a colorless oil.

$^1$H-NMR (300 MHz, CDCl$_3$): δ=0.93 ppm (t, 3H); 1.64 (quint, 2H); 2.52 (t, 2H); 3.46 (s, 2H); 3.75 (s, 3H)

12. 1-Oxobutylcyclopropanecarboxylic acid methyl ester 14

95 g of 13 is reacted analogously to 2., and 110 g of title compound 14 is obtained as a colorless oil.

$^1$H-NMR (300 MHz, CDCl$_3$): δ=0.91 ppm (t, 3H); 1.43 (s, 4H); 1.61 (quint, 2H); 2.81 (t, 2H); 3.75 (s, 3H)

13. 1-(2-Propyl-1,3-dioxolan-2-yl)cyclopropanecarboxylic acid methyl ester 15

113 g of 14 is reacted analogously to 3., and 78 g of title compound 15 is obtained as a colorless oil.

$^1$H-NMR (300 MHz, CDCl$_3$): δ=0.91 ppm (t, 3H); 1.00 (m, 2H); 1.04 (m, 2H); 1.40 (m, 2H); 2.04 (m, 2H); 3.68 (s, 3H); 3.93–3.98 (m, 4H)

14. 1-(2-Propyl-1,3-dioxolan-2-yl)cyclopropanemethanol 16

52 g of 15 is reacted analogously to 4., and 41.50 g of title compound 16 is obtained as a colorless oil.

$^1$H-NMR (300 MHz, CDCl$_3$): δ=0.40 ppm (m, 2H); 0.68 (m, 2H); 0.93 (t, 3H); 1.40 (m, 2H); 1.84 (m, 2H); 2.98 (t, OH); 3.50 (d, 2H); 3.98 (m, 4H)

15. 1-(2-Propyl-1,3-dioxolan-2-yl)cyclopropanecarbaldehyde 17

25.65 g of 16 is reacted analogously to 5., and 19.62 g of title compound 17 is obtained as a colorless oil.

$^1$H-NMR (300 MHz, CDCl$_3$): δ=0.92 ppm (t, 3H); 1.10 (s, 4H); 1.42 (m, 2H); 1.90 (m, 2H); 3.98 (m, 4H); 9.58 (s, 1H)

16. 2-(1-Ethenylcyclopropyl)-2-propyl-1,3-dioxolan 18

4.2 g of 17 is reacted analogously to 6., and 4.15 g of title compound 18 is obtained as a colorless oil.

$^1$H-NMR (300 MHz, CDCl$_3$): δ=0.54 ppm (m, 2H); 0.80 (m, 2H); 0.90 (t, 3H); 1.40 (m, 2H); 1.75 (m, 2H); 3.96 (m, 4H); 4.94 (d, 1H); 4.95 (d, 1H); 6.23 (dd, 1H)

17. 1-(2-Propyl-1,3-dioxolan-2-yl)cyclopropanethanol 19

4.15 g of 18 is reacted analogously to 7., and 2.71 g of title compound 19 is obtained as a colorless oil.

$^1$H-NMR (300 MHz, CDCl$_3$): δ=0.22 ppm (m, 2H); 0.69 (m, 2H); 0.94 (t, 3H); 3.65 (t, OH); 3.70 (m, 2H); 3.94 (m, 4H)

18. 4-Methylbenzenesulfonic acid 2-[1-(2-propyl-1,3-dioxolan-2-yl)cyclopropyl]ethyl ester 20

1.85 g of 19 is reacted analogously to 8., and 1.41 g of title compound 20 is obtained as a colorless oil.

$^1$H-NMR (300 MHz, CDCl$_3$): δ=0.20 ppm (m, 2H); 0.59 (m, 2H); 0.87 (t, 3H); 1.70 (t, 2H); 2.45 (s, 3H); 3.80 (m, 4H); 4.26 (t, 2H); 7.35 (d, 2H); 7.80 (d, 2H)

19. 2-[1-[2-(Phenylsulfanyl)ethyl]cyclopropyl]-2-propyl-1,3-dioxolan 21

1.41 g of 20 is reacted analogously to 9., and 980 mg of title compound 21 is obtained as a colorless oil.

$^1$H-NMR (300 MHz, CDCl$_3$): δ=0.23 ppm (m, 2H); 0.65 (m, 2H); 0.92 (t, 3H); 1.75 (t, 2H); 3.12 (t, 2H); 3.94 (m, 4H); 7.30 (m, 5H)

20. 2-[1-[2-(Phenylsulfonyl)ethyl]cyclopropyl]-2-propyl-1,3-dioxolan 22

910 mg of 21 is reacted analogously to 10., and 722 mg of title compound 22 is obtained as a colorless oil.

$^1$H-NMR (300 MHz, CDCl$_3$): δ=0.18 ppm (m, 2H); 0.62 (m, 2H); 0.86 (t, 3H); 1.32 (m, 2H); 1.58 (m, 2H); 1.72 (m, 2H); 3.40 (m, 2H); 3.81 (m, 4H); 7.57 (t, 2H); 7.65 (t, 1H); 7.90 (d, 2H)

21. 3-Oxoheptanoic acid methyl ester 23

118 ml of acetoacetic acid methyl ester 3 is reacted with n-iodopropane analogously to 11., and 135 g of title compound 23 is obtained as a colorless oil.

$^1$H-NMR (300 MHz, CDCl$_3$): δ=0.91 ppm (t, 3H); 1.32 (hex, 2H); 1.59 (quint, 2H); 2.53 (t, 2H); 3.47 (s, 2H); 3.75 (s, 3H)

22. 1-Oxopentylcyclopropanecarboxylic acid methyl ester 24

135 g of 23 is reacted analogously to 2., and 123 g of title compound 24 is obtained as a colorless oil.

$^1$H-NMR (300 MHz, CDCl$_3$): δ=0.90 ppm (t, 3H); 1.30 (hex, 2H); 1.42 (s, 4H); 1.58 (quint, 2H); 2.83 (t, 2H); 3.72 (s, 3H)

23. 1-(2-Butyl-1,3-dioxolan-2-yl)cyclopropanecarboxylic acid methyl ester 25

59 g of 24 is reacted analogously to 3., and 45 g of title compound 25 is obtained as a colorless oil.

¹H-NMR (300 MHz, CDCl₃): δ=0.89 ppm (t, 3H); 1.00 (m, 2H); 1.12 (m, 2H); 1.30 (m, 4H); 2.05 (m, 2H); 3.68 (s, 3H); 3.96 (m, 4H)

24. 1-(2-Butyl-1,3-dioxolan-2-yl)cyclopropanemethanol 26

25 g of 25 is reacted analogously to 4., and 16.8 g of title compound 26 is obtained as a colorless oil.
¹H-NMR (300 MHz, CDCl₃): δ=0.40 ppm (m, 2H); 0.69 (m, 2H); 0.89 (t, 3H); 1.32 (m, 4H); 1.84 (m, 2H); 3.02 (brs, OH); 3.50 (brs, 2H); 3.97 (m, 4H)

25. 1-(2-Butyl-1,3-dioxolan-2-yl)cyclopropanecarbaldehyde 27

16.3 g of 26 is reacted analogously to 5., and 16.0 g of title compound 27 is obtained as a colorless oil.
¹H-NMR (300 MHz, CDCl₃): δ=0.90 ppm (t, 3H); 1.10 (s, 4H); 1.33 (m, 4H); 1.90 (m, 2H); 3.98 (m, 4H); 9.58 (s, 1H)

26. 2-Butyl-2-(1-ethenylcyclopropyl)-1,3-dioxolan 28

5.0 g of 27 is reacted analogously to 6., and 3.89 g of title compound 28 is obtained as a colorless oil.
¹H-NMR (300 MHz, CDCl₃): δ=0.54 ppm (m, 2H); 0.80 (m, 2H); 0.90 (t, 3H); 1.30 (m, 4H); 1.79 (m, 2H); 3.94 (m, 4H); 4.94 (d, 1H); 4.95 (d, 1H); 6.22 (dd, 1H)

27. 1-(2-Butyl-1,3-dioxolan-2-yl)cyclopropanethanol 29

1.51 g of 28 is reacted analogously to 7., and 1.10 g of title compound 29 is obtained as a colorless oil.
¹H-NMR (300 MHz, CDCl₃): δ=0.22 ppm (m, 2H); 0.69 (m, 2H); 0.90 (t, 3H); 1.31 (m, 4H); 1.60 (t, 2H); 1.83 (m, 2H); 3.63 (brs, OH); 3.70 (m, 2H); 3.94 (m, 4H)

28. 4-Methylbenzenesulfonic acid 2-[1-(2-butyl-1,3-dioxolan-2-yl)cyproyl]ethyl ester 30

1.10 g of 29 is reacted analogously to 8., and 1.05 g of title compound 30 is obtained as a colorless oil.
¹H-NMR (300 MHz, CDCl₃): δ=0.20 ppm (m, 2H); 0.60 (m, 2H); 0.89 (t, 3H); 1.70 (t, 2H); 2.47 (s, 3H); 3.80 (m, 4H); 4.24 (t, 2H); 7.33 (d, 2H); 7.79 (d, 2H)

29. 2-Butyl-2-[1-[2-(phenylsulfanyl)ethyl]cyclopropyl]-1,3-dioxolan 31

1.05 g of 30 is reacted analogously to 9., and 675 mg of title compound 31 is obtained as a colorless oil.
¹H-NMR (300 MHz, CDCl₃): δ=0.23 ppm (m, 2H); 0.64 (m, 2H); 0.90 (t, 3H); 1.30 (m, 4H); 1.72 (m, 4H); 3.11 (m, 2H); 3.91 (m, 4H); 7.28 (m, 5H)

30. 2-Butyl-2-[1-[2-(phenylsulfonyl)ethyl]cyclopropyl]-1,3-dioxolan 32

1.15 g of 31 is reacted analogously to 10., and 913 mg of title compound 32 is obtained as a colorless oil.
¹H-NMR (300 MHz, CDCl₃): δ=0.19 ppm (m, 2H); 0.64 (m, 2H); 0.87 (t, 3H); 1.28 (m, 6H); 1.72 (m, 2H); 3.40 (m, 2H); 3.82 (m, 4H); 7.58 (t, 2H); 7.68 (t, 1H); 7.92 (d, 2H)

31. 3-Oxooctanoic acid methyl ester 33

23 g of acetoacetic acid methyl ester 3 is reacted with n-iodobutane analogously to 11., and 29.4 g of title compound 33 is obtained as a colorless oil.
¹H-NMR (300 MHz, CDCl₃): δ=0.90 ppm (t, 3H); 1.29 (m, 4H); 1.60 (m, 2H); 2.52 (t, 2H); 3.46 (s, 2H); 3.73 (s, 3H)

32. 1-Oxohexylcyclopropanecarboxylic acid methyl ester 34

18.3 g of 33 is reacted analogously to 2., and 15.2 g of title compound 34 is obtained as a colorless oil.
¹H-NMR (300 MHz, CDCl₃): δ=0.89 ppm (t, 3H); 1.30 (m, 4H); 1.45 (s, 4H); 1.60 (m, 2H); 2.81 (t, 2H); 3.75 (s, 3H)

33. 1-(2-Pentyl-1,3-dioxolan-2-yl)cyclopropanecarboxylic acid methyl ester 35

15.1 g of 34 is reacted analogously to 3., and 13.2 g of title compound 35 is obtained as a colorless oil.
¹H-NMR (300 MHz, CDCl₃): δ=0.89 ppm (t, 3H); 1.00 (m, 2H); 1.14 (m, 2H); 1.30 (m, 6H); 2.05 (m, 2H); 3.69 (s, 3H); 3.92 (m, 4H)

34. 1-(2-Pentyl-1,3-dioxolan-2-yl)cyclopropanemethanol 36

10.0 g of 35 is reacted analogously to 4., and 7.3 g of title compound 36 is obtained as a colorless oil.
¹H-NMR (300 MHz, CDCl₃): δ=0.40 ppm (m, 2H); 0.69 (m, 2H); 0.90 (t, 3H); 1.33 (m, 6H); 1.85 (m, 2H); 3.01 (t, OH); 3.50 (d, 2H); 3.97 (m, 4H)

35. 1-(2-Pentyl-1,3-dioxolan-2-yl)cyclopropanecarbaldehyde 37

7.3 g of 36 is reacted analogously to 5., and 5.9 g of title compound 37 is obtained as a colorless oil.
¹H-NMR (300 MHz, CDCl₃) δ=0.89 ppm (t, 3H); 1.10 (s, 4H); 1.24–1.47 (m, 6H); 1.90 (m, 2H); 3.98 (m, 4H); 9.58 (s, 1H)

36. 2-(1-Ethenylcyclopropyl)-2-pentyl-1,3-dioxolan 38

5.3 g of 37 is reacted analogously to 6., and 1.98 g of compound 38 is obtained as a colorless oil.
¹H-NMR (300 MHz, CDCl₃): δ=0.53 ppm (m, 2H); 0.80 (m, 2H); 0.89 (t, 3H); 1.20–1.45 (m, 6H); 1.77 (m, 2H); 3.96 (m, 4H); 4.96 (d, 1H); 4.97 (d, 1H); 6.23 (dd, 1H)

37. 1-(2-Pentyl-1,3-dioxolan-2-yl)cyclopropanethanol 39

1.70 g of 38 is reacted analogously to 7., and 1.20 g of title compound 39 is obtained as a colorless oil.
¹H-NMR (300 MHz, CDCl₃): δ=0.23 ppm (m, 2H); 0.70 (m, 2H); 0.90 (t, 3H); 1.22–1.43 (m, 6H); 1.62 (m, 2H); 1.85 (m, 2H); 3.57 (brs, OH); 3.70 (m, 2H); 3.94 (m, 4H)

38. 4-Methylbenzenesulfonic acid 2-[1-(2-pentyl-1,3-dioxolan-2-yl)cyclopropyl]ethyl ester 40

456 mg of 39 is reacted analogously to 8., and 620 mg of title compound 40 is obtained as a colorless oil.

$^1$H-NMR (300 MHz, CDCl$_3$): δ=0.20 ppm (m, 2H); 0.60 (m, 2H); 0.90 (t, 3H); 1.29 (m, 6H); 1.63 (m, 2H); 1.72 (t, 2H); 2.47 (s, 3H); 3.80 (m, 4H); 4.25 (t, 2H); 7.35 (d, 2H); 7.80 (d, 2H)

39. 2-Pentyl-2-[1-[2-(phenylsulfanyl)ethyl]cyclopropyl]-1,3-dioxolan 41

610 mg of 40 is reacted analogously to 9., and 499 mg of pound 41 is obtained as a colorless oil.

$^1$H-NMR (300 MHz, CDCl$_3$): δ=0.21 ppm (m, 2H); 0.63 (m, 2H); 0.89 (t, 3H); 1.19–1.42 (m, 6H); 1.72 (m, 4H); 3.10 (m, 2H); 3.90 (m, 4H); 7.30 (m, 5H)

40. 2-Pentyl-2-[1-[2-(phenylsulfonyl)ethyl]cyclopropyl]-1,3-dioxolan 42

318 mg of 41 is reacted analogously to 10., and 287 mg of pound 42 is obtained as a colorless oil.

$^1$H-NMR (300 MHz, CDCl$_3$): δ=0.17 ppm (m, 2H); 0.62 (m, 2H); 0.88 (t, 3H); 1.23 (m, 6H); 1.58 (m, 2H); 1.70 (m, 2H); 3.39 (m, 2H); 3.83 (m, 4H); 7.59 (t, 2H); 7.67 (t, 1H); 7.92 (d, 2H)

41. 3-Oxononanoic acid methyl ester 43

53.5 ml of acetoacetic acid methyl ester 3 is reacted with n-iodopentane analogously to 11., and 87.9 g of title compound 43 is obtained as a colorless oil.

$^1$H-NMR (300 MHz, CDCl$_3$): δ=0.88 ppm (t, 3H); 1.29 (m, 6H); 1.60 (m, 2H); 2.53 (t, 2H); 3.45 (s, 2H); 3.74 (s, 3H)

42. 1-Oxoheptylcyclopropanecarboxylic acid methyl ester 44

87.9 g of 43 is reacted analogously to 2., and 99.6 g of title compound 44 is obtained as a colorless oil.

$^1$H-NMR (300 MHz, CDCl$_3$): δ=0.88 ppm (t, 3H); 1.29 (m, 6H); 1.45 (s, 4H); 1.58 (m, 2H); 2.82 (t, 2H); 3.72 (s, 3H)

43. 1-(2-Hexyl-1,3-dioxolan-2-yl)cyclopropanecarboxylic acid methyl ester 45

102.4 g of 44 is reacted analogously to 3., and 85.86 g of title compound 45 is obtained as a colorless oil.

$^1$H-NMR (300 MHz, CDCl$_3$): δ=0.89 ppm (t, 3H); 1.00 (m, 2H); 1.15 (m, 2H); 1.30 (m, 8H); 2.05 (m, 2H); 3.67 (s, 3H); 3.94 (m, 4H)

44. 1-(2-Hexyl-1,3-dioxolan-2-yl)cyclopropanemethanol 46

63.45 g of 45 is reacted analogously to 4., and 51.92 g of title compound 46 is obtained as a colorless oil.

$^1$H-NMR (300 MHz, CDCl$_3$): δ=0.40 ppm (m, 2H); 0.70 (m, 2H); 0.90 (t, 3H); 1.32 (m, 8H); 1.87 (m, 2H); 3.01 (brs, OH); 3.51 (d, 2H); 3.97 (m, 4H)

45. 1-(2-Hexyl-1,3-dioxolan-2-yl)cyclopropanecarbaldehyde 47

10 g of 46 is reacted analogously to 5., and 7.9 g of title compound 47 is reacted as a colorless oil.

$^1$H-NMR (300 MHz, CDCl$_3$): δ=0.89 ppm (t, 3H); 1.10 (s, 4H); 1.29 (m, 8H); 1.90 (m, 2H); 3.97 (m, 4H); 9.60 (s, 1H)

46. 2-(1-Ethenylcyclopropyl)-2-hexyl-1,3-dioxolan 48

5.65 g of 47 is reacted analogously to 6., and 4.9 g of title compound 48 is obtained as a colorless oil.

$^1$H-NMR (300 MHz, CDCl$_3$): δ=0.57 ppm (m, 2H); 0.80 (m, 2H); 0.89 (t, 3H); 1.32 (m, 8H); 1.78 (m, 2H); 3.95 (m, 4H); 4.98 (d, 1H); 4.99 (d, 1H); 6.23 (dd, 1H)

47. 1-(2-Hexyl-1,3-dioxolan-2-yl)cyclopropanethanol 49

3.6 g of 48 is reacted analogously to 7., and 2.9 g of title compound 49 is obtained as a colorless oil.

$^1$H-NMR (300 MHz, CDCl$_3$): δ 0.22 ppm (m, 2H); 0.69 (m, 2H); 0.89 (t, 3H); 1.30 (m, 8H); 1.60 (t, 2H); 1.85 (m, 2H); 3.57 (brs, OH); 3.69 (m, 2H); 3.95 (m, 4H)

48. 4-Methylbenzenesulfonic acid 2-[1-(2-hexyl-1,3-dioxolan-2-yl)cyclopropyl]ethyl ester 50

2.1 g of 49 is reacted analogously to 8., and 2.3 g of title compound 50 is obtained as a colorless oil.

$^1$H-NMR (300 MHz, CDCl$_3$): δ=0.22 ppm (m, 2H); 0.60 (m, 2H); 0.90 (t, 3H); 1.29 (m, 8H); 1.68 (m, 2H); 1.73 (t, 2H); 2.48 (s, 3H); 3.84 (m, 4H); 4.29 (t, 2H); 7.38 (d, 2H); 7.82 (d, 2H)

49. 2-Hexyl-2-[1-[2-(phenylsulfanyl)ethyl]cyclopropyl]-1,3-dioxolan 51

2.3 g of 50 is reacted analogously to 9., and 1.98 g of title compound 51 is obtained as a colorless oil.

$^1$H-NMR (300 MHz, CDCl$_3$): δ=0.20 ppm (m, 2H); 0.61 (m, 2H); 0.89 (t, 3H); 1.19–1.42 (m, 8H); 1.73 (m, 4H); 3.10 (m, 2H); 3.91 (m, 4H); 7.30 (m, 5H)

50. 2-Hexyl-2-[1-[2-(phenylsulfonyl)ethyl]cyclopropyl]-1,3-dioxolan 52

1.98 g of 51 is reacted analogously to 10., and 1.50 g of title compound 52 is obtained as a colorless oil.

$^1$H-NMR (300 MHz, CDCl$_3$): δ 0.18 ppm (m, 2H); 0.63 (m, 2H); 0.89 (t, 3H); 1.28 (m, 8H); 1.58 (m, 2H); 1.72 (m, 2H); 3.40 (m, 2H); 3.82 (m, 4H); 7.58 (t, 2H); 7.67 (t, 1H); 7.92 (d, 2H)

51. 3-Oxodecanoic acid methyl ester 53

30 ml of acetoacetic acid methyl ester 3 is reacted with n-iodohexane analogously to 11., and 57.8 g of title compound 53 is obtained as a colorless oil.

$^1$H-NMR (300 MHz, CDCl$_3$): δ=0.88 ppm (t, 3H); 1.29 (m, 6H); 1.60 (m, 2H); 2.53 (t, 2H); 3.45 (s, 2H); 3.74 (s, 3H)

52. 1-Oxooctylcyclopropanecarboxylic acid methyl ester 54

57.8 g of 53 is reacted analogously to 2., and 62.6 g of title compound 54 is obtained as a colorless oil.

$^1$H-NMR (300 MHz, CDCl$_3$): δ=0.88 ppm (t, 3H); 1.30 (m, 10H); 1.40 (s, 4H); 2.82 (t, 2H); 3.68 (s, 3H)

53. 1-(2-Heptyl-1,3-dioxolan-2-yl)cyclopropanecarboxylic acid methyl ester 55

16.2 g of 54 is reacted analogously to 3., and 13.9 g of title compound 55 is obtained as a colorless oil.

$^1$H-NMR (300 MHz, CDCl$_3$): δ=0.89 ppm (t, 3H); 1.00 (m, 2H); 1.12 (m, 2H); 1.30 (m, 10H); 2.05 (m, 2H); 3.68 (s, 3H); 3.93 (m, 4H)

54. 1-(2-Heptyl-1,3-dioxolan-2-yl)cyclopropanemethanol 56

9.6 g of 55 is reacted analogously to 4., and 7.9 g of title compound 56 is obtained as a colorless oil.

$^1$H-NMR (300 MHz, CDCl$_3$): δ=0.40 ppm (m, 2H); 0.70 (m, 2H); 0.90 (t, 3H); 1.30 (m, 10H); 1.87 (m, 2H); 3.00 (d, OH); 3.51 (d, 2H); 3.98 (m, 4H)

55. 1-(2-Heptyl-1,3-dioxolan-2-yl)cyclopropanecarbaldehyde 57

11.4 g of 56 is reacted analogously to 5., and 7.6 g of title compound 57 is obtained as a colorless oil.

$^1$H-NMR (300 MHz, CDCl$_3$): δ=0.89 ppm (t, 3H); 1.10 (s, 4H); 1.30 (m, 10H); 1.90 (m, 2H); 3.98 (m, 4H); 9.58 (s, 1H)

56. 2-(1-Ethenylcyclopropyl)-2-heptyl-1,3-dioxolan 58

3.2 g of 57 is reacted analogously to 6., and 2.4 g of title compound 58 is obtained as a colorless oil.

$^1$H-NMR (300 MHz, CDCl$_3$): δ=0.54 ppm (m, 2H); 0.80 (m, 2H); 0.90 (t, 3H); 1.30 (m, 10H); 1.78 (m, 2H); 3.95 (m, 4H); 4.95 (d, 1H); 4.96 (d, 1H); 6.23 (dd, 1H)

57. 1-(2-Heptyl-1,3-dioxolan-2-yl)cyclopropanethanol 59

2.4 g of 58 is reacted analogously to 7., and 1.8 g of title compound 59 is obtained as a colorless oil.

$^1$H-NMR (300 MHz, CDCl$_3$): δ=0.23 ppm (m, 2H); 0.70 (m, 2H); 0.90 (t, 3H); 1.30 (m, 10H); 1.61 (t, 2H); 1.84 (m, 2H); 3.57 (brs, OH); 3.70 (m, 2H); 3.95 (m, 4H)

58. 4-Methylbenzensulfonic acid 2-[1-(2-heptyl-1,3-dioxolan-2-yl)cyclopropyl]ethyl ester 60

1.6 g of 59 is reacted analogously to 8., and 1.34 g of title compound 60 is obtained as a colorless oil.

$^1$H-NMR (300 MHz, CDCl$_3$): δ=0.23 ppm (m, 2H); 0.59 (m, 2H); 0.89 (t, 3H); 1.30 (m, 10H); 1.68 (m, 2H); 1.75 (t, 2H); 2.47 (s, 3H); 3.86 (m, 4H); 4.30 (t, 2H); 7.37 (d, 2H); 7.79 (d, 2H)

59. 2-Heptyl-2-[1-[2-(phenylsulfanyl)ethyl]cyclopropyl]-1,3-dioxolan 61

920 mg of 60 is reacted analogously to 9., and 743 mg of title compound 61 is obtained as a colorless oil.

$^1$H-NMR (300 MHz, CDCl$_3$): δ=0.20 ppm (m, 2H); 0.58 (m, 2H); 0.89 (t, 3H); 1.30 (m, 10H); 1.72 (m, 4H); 3.08 (m, 2H); 3.91 (m, 4H); 7.30 (m, 5H)

60. 2-Heptyl-2-[1-[2-(phenylsulfonyl)ethyl]cyclopropyl]-1,3-dioxolan 62

450 mg of 61 is reacted analogously to 10., and 356 mg of title compound 62 is obtained as a colorless oil.

$^1$H-NMR (300 MHz, CDCl$_3$): δ=0.18 ppm (m, 2H); 0.63 (m, 2H; 0.90 (t, 3H); 1.27 (m, 10H); 1.58 (m, 2H); 1.71 (m, 2H); 3.39 (m, 2H); 3.82 (m, 4H); 7.60 (t, 2H); 7.68 (t, 1H); 7.92 (d, 2H)

EXAMPLE 1

(5Z,7E,22E)-(1S,3R)-25-Acetyl-26,27-cyclo-9,10-secocholesta-5,7,10(19),22-tetraene-1,3-diol 66

61. Lithium diisopropylamide is prepared in 20 ml of THF at –78° C. under nitrogen from 0.18 ml of diisopropylamine and 0.57 ml of n-butyllithium solution (2.5 M in hexane). 380 mg of sulfone 12 is added in drops to 1 ml of THF, and it is stirred for 30 more minutes at –78° C. Then, 200 mg of aldehyde 2 in 0.5 ml of THF is added, and it is stirred for another 30 minutes. It is quenched with sodium chloride solution, extracted with diethyl ether, washed with sodium chloride solution, dried on sodium sulfate and concentrated by evaporation. The residue is chromatographed on silica gel with ethyl acetate/hexane, whereby 189 mg of (5Z,7E)-(1S,3R)-1,3-bis[[dimethyl(1,1-dimethylethyl)silyl]oxy]-25-(2-methyl-1,3-dioxolan-2-yl)-23-phenylsulfonyl-26,27-cyclo-9,10-secocholesta-5,7,10(19)-trien-22-ol 63 accumulates as a colorless foam.

62. 150 mg of 63 is introduced into 5 ml of methanol under nitrogen, and 10 ml of saturated, methanolic disodium hydrogen phosphate solution is added, and it is stirred for 15 minutes at room temperature. Then, 650 mg of a sodium amalgam (5%) is added, and it is stirred for 1 more hour. The mercury produced is decanted, and the reaction mixture is extracted with dichloromethane. After the organic phase is washed with sodium chloride solution, it is dried on sodium sulfate, the solvent is removed, and the residue is chromatographed on silica gel with ethyl acetate/hexane, whereby 65 mg of (5Z,7E,22E)-(1S,3R)-1,3-bis[[dimethyl(1,1-dimethylethyl)silyl]oxy]-25-(2-methyl-1,3-dioxolan-2-yl)-26,27-cyclo-9,10-secocholesta-5,7,10(19),22-tetraene 64 and 70 mg of (5Z,7E)-(1S,3R,22S)-1,3-bis[[dimethyl(1,1-dimethylethyl)silyl]oxy]-25-(2-methyl-1,3-dioxolan-2-yl)-26,27-cyclo-9,10-secocholesta-5,7,10(19)-trien-22-ol 65 accumulate in succession as colorless foams.

$^1$H-NMR (300 MHz, CDCl$_3$): 64: δ=0.03 ppm (s, 12H); 0.25 (m, 2H); 0.48 (m, 2H); 0.52 (s, 3H); 0.85 (s, 18H); 0.98 (d, 3H); 1.32 (s, 3H); 3.80 (m, 4H); 4.16 (m, 1H); 4.36 (m, 1H); 4.82 (s, 1H); 5.15 (s, 1H); 5.20 (m, 2H); 6.00 (d, 1H); 6.23 (d, 1H)

65: δ=0.04 ppm (s, 12H); 0.23 (m, 2H); 0.52 (s, 3H); 0.58 (m, 2H); 0.85 (d, 3H); 0.85 (s, 18H); 1.32 (s, 3H); 3.55 (m, 1H); 3.82 (m, 4H); 4.16 (m, 1H); 4.36 (m, 1H); 4.83 (s, 1H); 5.16 (s, 1H); 6.01 (d, 1H); 6.23 (d, 1H)

63. 35 mg of 64 is dissolved in 10 ml of dichloromethane/methanol (1:9), and it is stirred under nitrogen at room temperature with 350 mg of Dowex ion exchanger (activated) for 48 hours. Then, it is filtered, the filtrate is washed with sodium bicarbonate solution and sodium chloride solution, dried on sodium sulfate, concentrated by evaporation, and the residue is chromatographed on silica gel with ethyl acetate/hexane, whereby 13 mg of title compound 66 accumulates as a colorless foam.

$^{1}$H-NMR (300 MHz, CD$_{2}$Cl$_{2}$): δ=0.53 ppm (s, 3H); 0.78 (m, 2H); 1.01 (d, 3H); 1.20 (m, 2H); 2.10 (s, 3H); 4.19 (m, 1H); 4.39 (m, 1H); 4.98 (s, 1H); 5.30 (s, 1H); 5.32 (m, 2H); 6.01 (d, 1H); 6.38 (d, 1H)

EXAMPLE 2

64. (5Z,7E)-(1S,3R,22S)-25-Acetyl-26,27-cyclo-9,10-secocholesta-5,7,10(19)-triene-1,3,22-triol 67

11 mg of 65 is reacted analogously to 63., and 4.4 mg of the title compound is obtained as a colorless foam.

$^{1}$H-NMR (300 MHz, CD$_{2}$Cl$_{2}$): δ=0.55 ppm (s, 3H); 0.88 (d, 3H); 0.89 (t, 3H); 0.90 (m, 4H); 2.08 (s, 3H); 3.57 (m, 1H); 4.17 (m, 1H); 4.38 (m, 1H); 4.97 (s, 1H); 5.30 (s, 1H); 6.01 (d, 1H); 6.38 (d, 1H)

EXAMPLE 3

(5Z,7E,22E)-(1S,3R)-25-(1-Oxobutyl)-26,27-cyclo-9,10-secocholesta-5,7,10(19),22-tetraene-1,3-diol 71

65. 573 mg of aldehyde 2 is reacted with 700 mg of sulfone 22 analogously to 61., and 687 mg of (5Z,7E)-(1S,3R)-1,3-bis[[dimethyl(1,1-dimethylethyl)silyl]oxy]-23-phenylsulfonyl-25-(2-propyl-1,3-dioxolan-2-yl)-26,27-cyclo-9,10-secocholesta-5,7,10(19)-trien-22-ol 68 is obtained as a colorless foam.

66. 500 mg of 68 is reacted analogously to 62., whereby 189 mg of (5Z,7E,22E)-(1S,3R)-1,3-bis[[dimethyl(1,1-dimethylethyl)silyl]oxy]-25-(2-propyl-1,3-dioxolan-2-yl)-26,27-cyclo-9,10-secocholesta-5,7,10(19),22-tetraene 69 and 156 mg of (5Z,7E)-(1S,3R,22S)-1,3-bis[[dimethyl(1,1-dimethylethyl)silyl]oxy]-25-(2-propyl-1,3-dioxolan-2-yl)-26,27-cyclo-9,10-secocholesta-5,7,10(19)-trien-22-ol 70 accumulate in succession as colorless foams.

$^{1}$H-NMR (300 MHz, CDCl$_{3}$): 69: δ=0.03 ppm (s, 12H); 0.23 (m, 2H); 0.48 (m, 2H); 0.51 (s, 3H); 0.86 (s, 18H); 0.89 (t, 3H); 0.99 (d, 3H); 3.89 (m, 4H); 4.17 (m, 1H); 4.37 (m, 1H); 4.83 (s, 1H); 5.15 (s, 1H); 5.20 (m, 2H); 5.99 (d, 1H); 6.22 (d, 1H)

70: δ=0.04 ppm (s, 12H); 0.23 (m, 2H); 0.54 (s, 3H); 0.60 (m, 2H); 0.83 (t, 3H); 0.89 (d, 3H); 0.90 (s, 18H); 3.61 (m, 1H); 3.88 (m, 4H); 4.18 (m, 1H); 4.38 (m, 1H); 4.85 (s, 1H); 5.18 (s, 1H); 6.01 (d, 1H); 6.23 (d, 1H)

67. 180 mg of 69 is treated analogously to 63., and 85 mg of title compound 71 is obtained as a colorless foam.

$^{1}$H-NMR (300 MHz, CD$_{2}$Cl$_{2}$): δ=0.52 ppm (s, 3H); 0.72 (m, 2H); 0.87 (t, 3H); 1.00 (d, 3H); 1.15 (m, 2H); 1.51 (hex, 2H); 2.37 (t, 2H); 4.18 (m, 1H); 4.38 (m, 1H); 4.95 (s, 1H); 5.29 (s, 1H); 5.30 (m, 2H); 6.00 (d, 1H); 6.35 (d, 1H)

EXAMPLE 4

68. (5Z,7E)-(1S,3R,22S)-25-(1-Oxobutyl)-26,27-cyclo-9,10-secocholesta-5,7,10(19)-triene-1,3,22-triol 72

140 mg of 70 is reacted analogously to 63., and 39 mg of the title compound is obtained as a colorless foam.

$^{1}$H-NMR (300 MHz, CD$_{2}$Cl$_{2}$): δ=0.53 ppm (s, 3H); 0.88 (d, 3H); 0.89 (t, 3H); 0.90 (m, 4H); 2.38 (t, 2H); 3.56 (m, 1H); 4.17 (m, 1H); 4.38 (m, 1H); 4.96 (s, 1H); 5.28 (s, 1H); 6.01 (d, 1H); 6.38 (d, 1H)

EXAMPLE 5

(5Z,7E,22E)-(1S,3R)-25-(1-Oxopentyl)-26,27-cyclo-9,10-secocholesta-5,7,10(19),22-tetraene-1,3-diol 76

69. 573 mg of aldehyde 2 is reacted with 300 mg of sulfone 32 analogously to 61., and 420 mg of (5Z,7E)-(1S,3R)-1,3-bis[[dimethyl(1,1-dimethylethyl)silyl]oxy]-23-phenylsulfonyl-25-(2-butyl-1,3-dioxolan-2-yl)-26,27-cyclo-9,10-secocholesta-5,7,10(19)-trien-22-ol 73 is obtained as a colorless foam.

70. 250 mg of 73 is reacted analogously to 62., whereby 98 mg of (5Z,7E,22E)-(1S,3R)-1,3-bis[[dimethyl(1,1-dimethylethyl)silyl]oxy]-25-(2-butyl-1,3-dioxolan-2-yl)-26,27-cyclo-9,10-secocholesta-5,7,10(19),22-tetraene 74 and 82 mg of (5Z,7E)-(1S,3R,22S)-1,3-bis[[dimethyl(1,1-dimethylethyl)silyl]oxy]-25-(2-butyl-1,3-dioxolan-2-yl)-26,27-cyclo-9,10-secocholesta-5,7,10(19)-trien-22-ol 75 accumulate in succession as colorless foams.

$^{1}$H-NMR (300 MHz, CDCl$_{3}$): 74: δ=0.03 ppm (s, 12H); 0.21 (m, 2H); 0.47 (m, 2H); 0.51 (s, 3H); 0.86 (s, 18H); 0.88 (t, 3H); 0.98 (d, 3H); 3.86 (m, 4H); 4.17 (m, 1H); 4.37 (m, 1H); 4.82 (s, 1H); 5.15 (s, 1H); 5.18 (m, 2H); 5.99 (d, 1H); 6.22 (d, 1H)

75: δ=0.03 ppm (s, 12H); 0.21 (m, 2H); 0.54 (s, 3H); 0.58 (m, 2H); 0.88 (t, 3H); 0.89 (d, 3H); 0.89 (s, 18H); 3.57 (m, 1H); 3.86 (m, 4H); 4.17 (m, 1H); 4.37 (m, 1H); 4.82 (s, 1H); 5.17 (s, 1H); 6.00 (d, 1H); 6.22 (d, 1H)

71. 65 mg of 74 is treated analogously to 63., and 28 mg of title compound 76 is obtained as a colorless foam.

$^{1}$H-NMR (300 MHz, CD$_{2}$Cl$_{2}$): δ=0.53 ppm (s, 3H); 0.71 (m, 2H); 0.89 (t, 3H); 1.00 (d, 3H); 1.10 (m, 2H); 2.38 (t, 2H); 4.17 (m, 1H); 4.38 (m, 1H); 4.95 (s, 1H); 5.29 (s, 1H); 5.29 (m, 2H); 6.0 (d, 1H); 6.37 (d, 1H)

EXAMPLE 6

72. (5Z,7E)-(1S,3R,22S)-25-(1-Oxopentyl)-26,27-cyclo-9,10-secocholesta-5,7,10(19)-triene-1,3,22-triol 77

82 mg of 75 is reacted analogously to 63., and 34 mg of the title compound is obtained as a colorless foam.

$^{1}$H-NMR (300 MHz, CD$_{2}$Cl$_{2}$): δ=0.54 ppm (s, 3H); 0.89 (d, 3H); 0.89 (t, 3H); 0.90 (m, 4H); 2.36 (t, 2H); 3.55 (m, 1H); 4.17 (m, 1H); 4.37 (m, 1H); 4.96 (s, 1H); 5.28 (s, 1H); 6.01 (d, 1H); 6.37 (d, 1H)

EXAMPLE 7

(5Z,7E,22E)-(1S,3R)-25-(1-Oxohexyl)-26,27-cyclo-9,10-secocholesta-5,7,10(19),22-tetraene-1,3-diol 81

73. 171 mg of aldehyde 2 is reacted with 210 mg of sulfone 42 analogously to 61., and 194 mg of (5Z,7E)-(1S,3R)-1,3-bis[[dimethyl(1,1-dimethylethyl)silyl]oxy]-25-(2-pentyl-1,3-dioxolan-2-yl)-23-phenylsulfonyl-26,27-cyclo-9,10-secocholesta-5,7,10(19)-trien-22-ol 78 is obtained as a colorless foam.

74. 175 mg of 78 is reacted analogously to 62., whereby 65 mg of (5Z,7E,22E)-(1S,3R)-1,3-bis[[dimethyl(1,1-dimethylethyl)silyl]oxy]-25-(2-pentyl-1,3-dioxolan-2-yl)-26, 27-cyclo-9,10-secocholesta-5,7,10(19),22-tetraene 79 and 40 mg of (5Z,7E)-(1S,3R,22S)-1,3-bis[[dimethyl(1,1-dimethylethyl)silyl]oxy]-25-(2-pentyl-1,3-dioxolan-2-yl)-26,27-cyclo-9,10-secocholesta-5,7,10(19)-trien-22-ol 80 accumulate in succession as colorless foams.

$^1$H-NMR (300 MHz, CDCl$_3$): 79: δ=0.03 ppm (s, 12H); 0.22 (m, 2H); 0.45 (m, 2H); 0.52 (s, 3H); 0.85 (s, 18H); 0.85 (t, 3H); 0.98 (d, 3H); 3.85 (m, 4H); 4.17 (m, 1H); 4.37 (m, 1H); 4.83 (s, 1H); 5.16 (s, 1H); 5.18 (m, 2H); 6.00 (d, 1H); 6.23 (d, 1H)

80: δ=0.03 ppm (s, 12H); 0.22 (m, 2H); 0.53 (s, 3H); 0.58 (m, 2H); 0.88 (t, 3H); 0.89 (d, 3H); 0.89 (s, 18H); 3.56 (m, 1H); 3.86 (m, 4H); 4.16 (m, 1H); 4.36 (m, 1H); 4.82 (s, 1H); 5.17 (s, 1H); 6.00 (d, 1H); 6.22 (d, 1H)

75. 64 mg of 79 is treated analogously to 63., and 26 mg of title compound 81 is obtained as a colorless foam.

$^1$H-NMR (300 MHz, CD$_2$Cl$_2$): δ=0.53 ppm (s, 3H); 0.70 (m, 2H); 0.89 (t, 3H); 0.99 (d, 3H); 1.10 (m, 2H); 2.37 (t, 2H); 4.17 (m, 1H); 4.38 (m, 1H); 4.96 (s, 1H); 5.30 (s, 1H); 5.31 (m, 2H); 6.00 (d, 1H); 6.36 (d, 1H)

EXAMPLE 8

76. (5Z,7E)-(1S,3R,22S)-25-(1-Oxohexyl)-26,27-cyclo-9,10-secocholesta-5,7,10(19)-triene-1,3,22-triol 82

35 mg of 80 is reacted analogously to 63., and 174 mg of the title compound is obtained as a colorless foam.

$^1$H-NMR (300 MHz, CD$_2$Cl$_2$): δ=0.55 ppm (s, 3H); 0.89 (d, 3H); 0.90 (t, 3H); 0.91 (m, 4H); 2.37 (t, 2H); 3.56 (m, 1H); 4.17 (m, 1H); 4.38 (m, 1H); 4.96 (s, 1H); 5.28 (s, 1H); 6.01 (d, 1H); 6.38 (d, 1H)

EXAMPLE 9

(5Z,7E,22E)-(1S,3R)-25-(1-Oxoheptyl)-26,27-cyclo-9,10-secocholesta-5,7,10(19),22-tetraene-1,3-diol 86

77. 573 mg of aldehyde 2 is reacted with 1.07 g of sulfone 52 analogously to 61., and 432 mg of (5Z,7E)-(1S,3R)-1,3-bis[[dimethyl(1,1-dimethylethyl)silyl]oxy]-25-(2-hexyl-1,3-dioxolan-2-yl)-23-phenylsulfonyl-26,27-cyclo-9,10-secocholesta-5,7,10(19)-trien-22-ol 83 is obtained as a colorless foam.

78. 432 mg of 83 is reacted analogously to 62., whereby 93 mg of (5Z,7E,22E)-(1S,3R)-1,3-bis[[dimethyl(1,1-dimethylethyl)silyl]oxy]-25-(2-hexyl-1,3-dioxolan-2-yl)-26,27-cyclo-9,10-secocholesta-5,7,10(19),22-tetraene 84 and 48 mg of (5Z,7E)-(1S,3R,22S)-1,3-bis[[dimethyl(1,1-dimethylethyl)silyl]oxy]-25-(2-hexyl-1,3-dioxolan-2-yl)-26,27-cyclo-9,10-secocholesta-5,7,10(19)-trien-22-ol 85 accumulate in succession as colorless foams.

$^1$H-NMR (300 MHz, CDCl$_3$): 84: δ=0.03 ppm (s, 12H); 0.20 (m, 2H); 0.46 (m, 2H); 0.52 (s, 3H); 0.85 (s, 18H); 0.88 (t, 3H); 0.99 (d, 3H); 3.85 (m, 4H); 4.17 (m, 1H); 4.37 (m, 1H); 4.82 (s, 1H); 5.15 (s, 1H); 5.20 (m, 2H); 6.00 (d, 1H); 6.22 (d, 1H)

85: δ=0.03 ppm (s, 12H); 0.20 (m, 2H); 0.53 (s, 3H); 0.55 (m, 2H); 0.87 (t, 3H); 0.88 (d, 3H); 0.89 (s, 18H); 3.55 (m, 1H); 3.84 (m, 4H); 4.16 (m, 1H); 4.36 (m, 1H); 4.82 (s, 1H); 5.16 (s, 1H); 6.01 (d, 1H); 6.23 (d, 1H)

79. 93 mg of 84 is treated analogously to 63., and 31 mg of title compound 86 is obtained as a colorless foam.

$^1$H-NMR (300 MHz, CD$_2$Cl$_2$): δ=0.53 ppm (s, 3H); 0.69 (m, 2H); 0.87 (t, 3H); 1.00 (d, 3H); 1.08 (m, 2H); 2.36 (t, 2H); 4.16 (m, 1H); 4.36 (m, 1H); 4.94 (s, 1H); 5.27 (s, 1H); 5.27 (m, 2H); 5.99 (d, 1H); 6.34 (d, 1H)

EXAMPLE 10

80. (5Z,7E)-(1S,3R,22S)-25-(1-Oxoheptyl)-26,27-cyclo-9,10-secocholesta-5,7,10(19)-triene-1,3,22-triol 87

48 mg of 85 is reacted analogously to 63., and 16 mg of the title compound is obtained as a colorless foam.

$^1$H-NMR (300 MHz, CD$_2$Cl$_2$): δ=0.53 ppm (s, 3H); 0.86 (d, 3H); 0.88 (t, 3H); 0.90 (m, 4H); 2.35 (t, 2H); 3.55 (m, 1H); 4.16 (m, 1H); 4.36 (m, 1H); 4.95 (s, 1H); 5.28 (s, 1H); 6.00 (d, 1H); 6.35 (d, 1H)

EXAMPLE 11

(5Z,7E,22E)-(1S,3R)-25-(1-Oxooctyl)-26,27-cyclo-9,10-secocholesta-5,7,10(19),22-tetraene-1,3-diol 91

81. 460 mg of aldehyde 2 is reacted with 600 mg of sulfone 62 analogously to 61., and 532 mg of (5Z,7E)-(1S,3R)-1,3-bis[[dimethyl(1,1-dimethylethyl)silyl]oxy]-25-(2-heptyl-1,3-dioxolan-2-yl)-23-phenylsulfonyl-26,27-cyclo-9,10-secocholesta-5,7,10(19)-trien-22-ol 88 is obtained as a colorless foam.

82. 500 mg of 88 is reacted analogously to 62., whereby 145 mg of (5Z,7E,22E)-(1S,3R)-1,3-bis[[dimethyl(,1-dimethylethyl)silyl]oxy]-25-(2-heptyl-1,3-dioxolan-2-yl)-26,27-cyclo-9,10-secocholesta-5,7,10(19),22-tetraene 89 and 158 mg of (5Z,7E)-(1S,3R,22S)-1,3-bis[[dimethyl(1,1-dimethylethyl)silyl]oxy]-25-(2-heptyl-1,3-dioxolan-2-yl)-26,27-cyclo-9,10-secocholesta-5,7,10(19)-trien-22-ol 90 accumulate in succession as colorless foams.

$^1$H-NMR (300 MHz, CDCl$_3$): 89: δ=0.04 ppm (s, 12H); 0.21 (m, 2H); 0.45 (m, 2H); 0.52 (s, 3H); 0.87 (s, 18H); 0.87 (t, 3H); 0.99 (d, 3H); 3.85 (m, 4H); 4.17 (m, 1H); 4.36 (m, 1H); 4.82 (s, 1H); 5.15 (s, 1H); 5.20 (m, 2H); 6.00 (d, 1H); 6.22 (d, 1H)

90: δ=0.03 ppm (s, 12H); 0.21 (m, 2H); 0.53 (s, 3H); 0.54 (m, 2H); 0.88 (t, 3H); 0.88 (d, 3H); 0.89 (s, 18H); 3.54 (m, 1H); 3.84 (m, 4H); 4.17 (m, 1H); 4.36 (m, 1H); 4.83 (s, 1H); 5.18 (s, 1H); 6.00 (d, 1H); 6.23 (d, 1H)

83. 121 mg of 89 is treated analogously to 63., and 52 mg of title compound 91 is obtained as a colorless foam.

$^1$H-NMR (300 MHz, CD$_2$Cl$_2$): δ=0.52 ppm (s, 3H); 0.70 (m, 2H); 0.88 (t, 3H); 0.99 (d, 3H); 1.10 (m, 2H); 2.36 (t, 2H); 4.17 (m, 1H); 4.37 (m, 1H); 4.94 (s, 1H); 5.28 (s, 1H); 5.30 (m, 2H); 5.99 (d, 1H); 6.35 (d, 1H)

EXAMPLE 12

84. (5Z,7E)-(1S,3R,22S)-25-(1-Oxooctyl)-26,27-cyclo-9,10-secocholesta-5,7,10(19)-triene-1,3,22-triol 92

130 mg of 90 is reacted analogously to 63., and 41 mg of title compound 92 is obtained as a colorless foam.

$^1$H-NMR (300 MHz, CD$_2$Cl$_2$): δ=0.55 ppm (s, 3H); 0.86 (d, 3H); 0.87 (t, 3H); 0.90 (m, 4H); 2.36 (t, 2H); 3.55 (m, 1H); 4.17 (m, 1H); 4.37 (m, 1H); 4.95 (s, 1H); 5.27 (s, 1H); 6.00 (d, 1H); 6.36 (d, 1H)

Synthesis of the Starting Compounds in the
24-Methylene-24-homo Series

85. (E)-3-[1-(2-Methyl-1,3-dioxolan-2-yl)cyclopropyl]propenoic acid methyl ester 93

3 g of sodium hydride suspension (60% in paraffin oil) is introduced into 750 ml of THF, cooled under nitrogen to 0° C., and 10.9 g of dimethylphosphonoacetic acid methyl ester is added. Then, 7.5 g of aldehyde 7 is added in drops to 15 ml of THF, and it is stirred at room temperature for 2 hours. It is now quenched carefully with sodium chloride solution, extracted with ethyl acetate, washed with sodium chloride solution, dried on sodium sulfate, and the solvent is removed. The residue is chromatographed on silica gel with ethyl acetate/hexane, whereby 9.5 g of title compound 93 accumulates as a colorless oil.

$^1$H-NMR (300 MHz, CDCl$_3$): δ=0.73 ppm (m, 2H); 1.09 (m, 2H); 1.45 (s, 3H); 3.72 (s, 3H); 3.95 (m, 4H); 5.79 (d, 1H); 7.18 (d, 1H)

86. 3-[1-(2-Methyl-1,3-dioxolan-2-yl)cyclopropane]-1-propanol 94

100 ml of liquid ammonia is introduced, and 2 g of lithium is added in portions. Then, 3.1 g of 93 is added in drops to 20 ml of THF, and it is stirred overnight at room temperature, whereby the ammonia is evaporated. The residue is taken up in ethyl acetate, washed with sodium chloride solution, dried on sodium sulfate, concentrated by evaporation, and chromatographed on silica gel with ethyl acetate/hexane, whereby 1.5 g of title compound 94 is obtained as a colorless oil.

$^1$H-NMR (300 MHz, CDCl$_3$): δ=0.29 ppm (m, 2H); 0.62 (m, 2H); 1.40 (s, 3H); 1.51–1.70 (m, 4H); 3.62 (t, 2H); 3.90 (m, 4H)

87. 4-Methylbenzenesulfonic acid 3-[1-(2-methyl-1,3-dioxolan-2-yl)-cyclopropyl]propyl ester 95

350 mg of 94 is reacted analogously to 8., whereby 405 mg of title compound 95 accumulates as a colorless oil.

$^1$H-NMR (300 MHz, CDCl$_3$): δ=0.19 ppm (m, 2H); 0.60 (m, 2H); 1.32 (s, 3H); 1.44 (m, 2H); 1.79 (m, 2H); 2.46 (s, 3H); 3.85 (m, 4H); 4.02 (t, 2H); 7.35 (d, 2H); 7.79 (d, 2H)

88. 2-Methyl-2-[1-[3-(phenylsulfanyl)ethyl]cyclopropyl]-1,3-dioxolan 96

400 mg of 95 is reacted analogously to 9., whereby 380 mg of title compound 96 accumulates as a colorless oil.

$^1$H-NMR (300 MHz, CDCl$_3$): δ=0.27 ppm (m, 2H); 0.60 (m, 2H); 1.38 (s, 3H); 1.61 (m, 2H); 1.76 (m, 2H); 2.92 (t, 2H); 3.89 (m, 4H); 7.28 (m, 5H)

89. 2-Methyl-2-[1-[3-(phenylsulfonyl)ethyl]cyclopropyl]-1,3-dioxolan 97

375 mg of 96 is reacted analogously to 10., whereby 268 mg of title compound 97 is obtained as a colorless oil.

$^1$H-NMR (300 MHz, CDCl$_3$): δ=0.20 ppm (m, 2H); 0.62 (m, 2H); 1.31 (s, 3H); 1.52 (m, 2H); 1.87 (m, 2H); 3.12 (t, 2H); 3.83 (m, 4H); 7.58 (t, 2H); 7.66 (t, 1H); 7.91 (d, 2H)

90. (E)-3-[1-(2-Propyl-1,3-dioxolan-2-yl)cyclopropyl]propenoic acid methyl ester 98

6.0 g of aldehyde 17 is reacted analogously to 85., and 6.7 g of title compound 98 is obtained as a colorless oil.

$^1$H-NMR (300 MHz, CDCl$_3$): δ=0.70 ppm (m, 2H); 0.90 (t, 3H); 0.90 (m, 2H); 1.03 (m, 2H); 1.73 (m, 2H); 3.72 (s, 3H); 3.95 (m, 4H); 5.70 (d, 1H); 7.25 (d, 1H)

91. 3-[1-(2-Propyl-1,3-dioxolan-2-yl)cyclopropane]-1-propanol 99

6.7 g of 98 is reacted analogously to 86., whereby 5.3 g of title compound 99 is obtained as a colorless oil.

$^1$H-NMR (300 MHz, CDCl$_3$): δ=0.23 ppm (m, 2H); 0.60 (m, 2H); 0.92 (t, 3H); 3.62 (t, 2H); 3.90 (m, 4H)

92. 4-Methylbenzenesulfonic acid 3-[1-(2-propyl-1,3-dioxolan-2-yl)cyclopropyl]propyl ester 100

1.3 g of 99 is reacted analogously to 8., whereby 1.52 g of title compound 100 accumulates as a colorless oil.

$^1$H-NMR (300 MHz, CDCl$_3$): δ=0.12 ppm (m, 2H); 0.57 (m, 2H); 0.90 (t, 3H); 2.47 (s, 3H); 3.83 (m, 4H); 4.02 (t, 2H); 7.35 (d, 2H); 7.79 (d, 2H)

93. 2-[1-[3-(Phenylsulfanyl)ethyl]cyclopropyl]-2-propyl-1,3-dioxolan 101

1.5 g of 100 is reacted analogously to 9., whereby 1.11 g of title compound 96 accumulates as a colorless oil.

$^1$H-NMR (300 MHz, CDCl$_3$): δ=0.20 ppm (m, 2H); 0.58 (m, 2H); 0.91 (t, 3H); 2.91 (t, 2H); 3.88 (m, 4H); 7.28 (m, 5H)

94. 2-[1-[3-(Phenylsulfonyl)ethyl]cyclopropyl]-2-propyl-1,3-dioxolan 102

1.1 g of 101 is reacted analogously to 10., whereby 785 mg of title compound 102 is obtained as a colorless oil.

$^1$H-NMR (300 MHz, CDCl$_3$): δ=0.17 ppm (m, 2H); 0.59 (m, 2H); 0.90 (t, 3H); 3.10 (t, 2H); 3.85 (m, 4H); 7.58 (t, 2H); 7.67 (t, 1H); 7.90 (d, 2H)

95. (E)-3-[1-(2-Butyl-1,3-dioxolan-2-yl)cyclopropyl]propenoic acid methyl ester 103

5.0 g of aldehyde 27 is reacted analogously to 85., and 4.6 g of title compound 103 is obtained as a colorless oil.

$^1$H-NMR (300 MHz, CDCl$_3$): δ=0.70 ppm (m, 2H); 0.89 (t, 3H); 1.04 (m, 2H); 1.30 (m, 4H); 1.79 (m, 2H); 3.72 (s, 3H); 3.96 (m, 4H); 5.71 (d, 1H); 7.25 (d, 1H)

96. 3-[1-(2-Butyl-1,3-dioxolan-2-yl)cyclopropane]-1-propanol 104

1.5 g of 103 is reacted analogously to 86., whereby 1.09 g of title compound 104 is obtained as a colorless oil.

$^1$H-NMR (300 MHz, CDCl$_3$): δ=0.23 ppm (m, 2H); 0.60 (m, 2H); 0.92 (t, 3H); 3.61 (t, 2H); 3.92 (m, 4H)

97. 4-Methylbenzenesulfonic acid 3-[1-(2-butyl-1,3-dioxolan-2-yl)cyclopropyl]propylester 105

1.09 g of 104 is reacted analogously to 8., whereby 1.36 g of title compound 105 accumulates as a colorless oil.

¹H-NMR (300 MHz, CDCl₃): δ=0.12 ppm (m, 2H); 0.58 (m, 2H); 0.89 (t, 3H); 2.47 (s, 3H); 3.85 (m, 4H); 4.02 (t, 2H); 7.35 (d, 2H); 7.80 (d, 2H)

98. 2-Butyl-2-[1-[3-(phenylsulfanyl)ethyl]cyclopropyl]-1,3-dioxolan 106

800 mg of 105 is reacted analogously to 9., whereby 967 mg of title compound 106 accumulates as a colorless oil.
¹H-NMR (300 MHz, CDCl₃): δ=0.20 ppm (m, 2H); 0.59 (m, 2H); 0.90 (t, 3H); 2.89 (t, 2H); 3.85 (m, 4H); 7.27 (m, 5H) 99. 2-Butyl-2-[1-[3-(phenylsulfonyl)ethyl]cyclopropyl]-1,3-dioxolan 107

950 g of 106 is reacted analogously to 10., whereby 634 mg of title compound 107 is obtained as a colorless oil.
¹H-NMR (300 MHz, CDCl₃): δ=0.15 ppm (m, 2H); 0.60 (m, 2H); 0.90 (t, 3H); 3.09 (t, 2H); 3.83 (m, 4H); 7.58 (t, 2H); 7.68 (t, 1H); 7.91 (d, 2H)

100. (E)-3-[1-(2-Pentyl-1,3-dioxolan-2-yl)cyclopropyl]propenoic acid methyl ester 108

1.8 g of aldehyde 37 is reacted analogously to 85., and 1.1 g of title compound 108 is obtained as a colorless oil.
¹H-NMR (300 MHz, CDCl₃): δ=0.70 ppm (m, 2H); 0.88 (t, 3H); 1.03 (m, 2H); 1.30 (m, 6H); 372 (s, 3H); 3.95 (m, 4H); 5.71 (d, 1H); 7.24 (d, 1H)

101. 3-[1-(2-Pentyl-1,3-dioxolan-2-yl)cyclopropane]-1-propanol109

2.68 g of 108 is reacted analogously to 86., whereby 1.57 g of title compound 109 is obtained as a colorless oil.
¹H-NMR (300 MHz, CDCl₃): δ=0.23 ppm (m, 2H); 0.60 (m, 2H); 0.90 (t, 3H); 3.61 (t, 2H); 3.91 (m, 4H)

102. 4-Methylbenzenesulfonic acid 3-[1-(2-pentyl-1,3-dioxolan-2-yl)cyclopropyl]propylester 110

590 mg of 109 is reacted analogously to 8., whereby 456 g of title compound 110 accumulates as a colorless oil.
¹H-NMR (300 MHz, CDCl₃): δ=0.18 ppm (m, 2H); 0.60 (m, 2H); 0.90 (t, 3H); 2.48 (s, 3H); 3.85 (m, 4H); 4.02 (t, 2H); 7.35 (d, 2H); 7.81 (d, 2H)

103. 2-Pentyl-2-[1-[3-(phenylsulfanyl)ethyl]cyclopropyl]-1,3-dioxolan 111

350 mg of 110 is reacted analogously to 9., whereby 272 mg compound 111 accumulates as a colorless oil.
¹H-NMR (300 MHz, CDCl₃): δ=0.19 ppm (m, 2H); 0.59 (m, 2H); 0.89 (t, 3H); 2.87 (t, 2H); 3.85 (m, 4H); 7.28 (m, 5H)

104. 2-Pentyl-2-[1-[3-(phenylsulfonyl)ethyl]cyclopropyl]-1,3-dioxolan 112

245 mg of 111 is reacted analogously to 10., whereby 191 mg of title compound 112 is obtained as a colorless oil.
¹H-NMR (300 MHz, CDCl₃): δ=0.14 ppm (m, 2H); 0.57 (m, 2H); 0.88 (t, 3H); 3.09 (t, 2H); 3.82 (m, 4H); 7.58 (t, 2H); 7.67 (t, 1H); 7.89 (d, 2H)

105. (E)-3-[1-(2-Hexyl-1,3-dioxolan-2-yl)cyclopropyl]propenoic acid methyl ester 113

5.65 g of aldehyde 47 is reacted analogously to 85., and 4.81 g of title compound 113 is obtained as a colorless oil.
¹H-NMR (300 MHz, CDCl₃): δ=0.70 ppm (m, 2H); 0.89 (t, 3H); 1.04 (m, 2H); 1.29 (m, 8H); 3.72 (s, 3H); 3.96 (m, 4H); 5.71 (d, 1H); 7.25 (d, 1H)

106. 3-[1-(2-Hexyl-1,3-dioxolan-2-yl)cyclopropane]-1-propanol 114

2.0 g of 113 is reacted analogously to 86., whereby 1.7 g of title compound 114 is obtained as a colorless oil.
¹H-NMR (300 MHz, CDCl₃): δ=0.22 ppm (m, 2H); 0.60 (m, 2H); 0.89 (t, 3H); 3.62 (t, 2H); 3.90 (m, 4H)

107. 4-Methylbenzenesulfonic acid 3-[1-(2-hexyl-1,3-dioxolan-2-yl)cyclopropyl]propyl ester 115

1.7 mg of 114 is reacted analogously to 8., whereby 1.6 g of title compound 115 accumulates as a colorless oil.
¹H-NMR (300 MHz, CDCl₃): δ=0.20 ppm (m, 2H); 0.60 (m, 2H); 0.91 (t, 3H); 2.49 (s, 3H); 3.85 (m, 4H); 4.03 (t, 2H); 7.36 (d, 2H); 7.81 (d, 2H)

108. 2-Hexyl-2-[1-[3-(phenylsulfanyl)ethyl]cyclopropyl]-1,3-dioxolan 116

1.5 mg of 115 is reacted analogously to 9., whereby 1.37 g of title compound 116 accumulates as a colorless oil.
¹H-NMR (300 MHz, CDCl₃): δ=0.19 ppm (m, 2H); 0.60 (m, 2H); 0.90 (t, 3H); 2.87 (t, 2H); 3.85 (m, 4H); 7.30 (m, 5H)

109. 2-Hexyl-2-[1-[3-(phenylsulfonyl)ethyl]cyclopropyl]-1,3-dioxolan 117

654 mg of 116 is reacted analogously to 10., whereby 630 mg of title compound 117 is obtained as a colorless oil.
¹H-NMR (300 MHz, CDCl₃): δ=0.14 ppm (m, 2H); 0.58 (m, 2H); 0.86 (t, 3H); 3.09 (t, 2H); 3.82 (m, 4H); 7.57. (t, 2H); 7.65 (t, 1H); 7.89 (d, 2H)

110. (E)-3-[1-(2-Heptyl-1,3-dioxolan-2-yl)cyclopropyl]propenoic acid methyl ester 118

2.2 g of aldehyde 57 is reacted analogously to 85., and 1.7 g of title compound 118 is obtained as a colorless oil.
¹H-NMR (300 MHz, CDCl₃): δ=0.70 ppm (m, 2H); 0.89 (t, 3H); 1.04 (m, 2H); 1.29 (m, 10H); 3.72 (s, 3H); 3.95 (m, 4H); 5.71 (d, 1H); 7.25 (d, 1H)

111. 3-[1-(2-Heptyl-1,3-dioxolan-2-yl)cyclopropane]-1-propanol 119

1.6 g of 118 is reacted analogously to 86., whereby 987 mg of title compound 119 is obtained as a colorless oil.
¹H-NMR (300 MHz, CDCl₃): δ=0.23 ppm (m, 2H); 0.60 (m, 2H); 0.89 (t, 3H); 3.62 (t, 2H); 3.90 (m, 4H)

112. 4-Methylbenzenesulfonic acid 3-[1-(2-heptyl-1,3-dioxolan-2-yl)cyclopropyl]propylester 120

900 mg of 119 is reacted analogously to 8., whereby 1.3 g of title compound 120 accumulates as a colorless oil.

¹H-NMR (300 MHz, CDCl₃): δ=0.22 ppm (m, 2H); 0.60 (m, 2H); 0.90 (t, 3H); 2.48 (s, 3H); 3.85 (m, 4H); 4.03 (t, 2H); 7.37 (d, 2H); 7.81 (d, 2H)

113. 2-Heptyl-2-[1-[3-(phenylsulfanyl)ethyl]cyclopropyl]-1,3-dioxolan 121

1.3 mg of 120 is reacted analogously to 9., whereby 921 mg compound 121 accumulates as a colorless oil.

¹H-NMR (300 MHz, CDCl₃): δ=0.22 ppm (m, 2H); 0.62 (m, 2H); 0.90 (t, 3H); 2.90 (t, 2H); 3.85 (m, 4H); 7.30 (m, 5H)

114. 2-Heptyl-2-[1-[3-(phenylsulfonyl)ethyl]cyclopropyl]-1,3-dioxolan 122

456 mg of 121 is reacted analogously to 10., whereby 376 mg of title compound 122 is obtained as a colorless oil.

¹H-NMR (300 MHz, CDCl₃): δ=0.17 ppm (m, 2H); 0.59 (m, 2H); 0.89 (t, 3H); 3.10 (t, 2H); 3.82 (m, 4H); 7.58 (t, 2H); 7.67 (t, 1H) 7.90 (d, 2H)

EXAMPLE 13

(5Z,7E,22E)-(1S,3R)-25-Acetyl-26,27-cyclo-24a-homo-9,10-secocholesta-5,7,10(19),22-tetraene-1,3-diol 126

115. 343 mg of aldehyde 2 is reacted with 260 mg of sulfone 97 analogously to 61., and 402 mg of (5Z,7E)-(1S,3R)-1,3-bis[[dimethyl(1,1-dimethylethyl)silyl]oxy]-25-(2-methyl-1,3-dioxolan-2-yl)-23-phenylsulfonyl-26,27-cyclo-24a-homo-9,10-secocholesta-5,7,10(19)-trien-22-ol 123 is obtained as a colorless foam.

116. 400 mg of 123 is reacted analogously to 62., whereby 123 mg of (5Z,7E,22E)-(1S,3R)-1,3-bis[[dimethyl(1,1-dimethylethyl)-silyl]oxy]-25-(2-methyl-1,3-dioxolan-2-yl)-26,27-cyclo-24a-homo-9,10-secocholesta-5,7,10(19),22-tetraene 124 and 70 mg of (5Z,7E)-(1S,3R,22S)-1,3-bis[[dimethyl(1,1-dimethylethyl)silyl]oxy]-25-(2-methyl-1,3-dioxolan-2-yl)-26,27-cyclo-24a-homo-9,10-secocholesta-5,7,10(19)-trien-22-ol 125 accumulate in succession as colorless foams.

¹H-NMR (300 MHz, CDCl₃): 124: δ=0.03 ppm (s, 12H); 0.23 (m, 2H); 0.52 (s, 3H); 0.55 (d, 2H); 0.86 (s, 18H); 0.86 (d, 3H); 1.32 (s, 3H); 3.83 (m, 4H); 4.16 (m, 1H); 4.36 (m, 1H); 4.82 (s, 1H); 5.15 (s, 1H); 5.22 (m, 2H); 6.00 (d, 1H); 6.23 (d, 1H)

125: δ=0.04 ppm (s, 12H); 0.23 (m, 2H); 0.52 (s, 3H); 0.55 (m, 2H); 0.85 (d, 3H); 0.86 (s, 18H); 1.32 (s, 3H); 3.61 (m, 1H); 3.82 (m, 4H); 4.16 (m, 1H); 4.36 (m, 1H); 4.82 (s, 1H); 5.15 (s, 1H); 6.01 (d, 1H); 6.23 (d, 1H)

117. 98 mg of 124 is reacted analogously to 63., whereby 43 mg of title compound 126 is obtained as a colorless foam.

¹H-NMR (300 MHz, CD₂Cl₂): δ=0.53 ppm (s, 3H); 0.78 (m, 2H); 1.00 (d, 3H); 1.20 (m, 2H); 2.00 (s, 3H); 4.19 (m, 1H); 4.38 (m, 1H); 4.99 (s, 1H); 5.28 (m, 2H); 5.30 (s, 1H); 6.01 (d, 1H); 6.38 (d, 1H)

EXAMPLE 14

118. (5Z,7E)-(1S,3R,22S)-25-Acetyl-26,27-cyclo-24a-homo-9,10-secocholesta-5,7,10(19)-triene-1,3,22-triol 127

61 mg of 125 is reacted analogously to 63., and 24 mg of the title compound is obtained as a colorless foam.

¹H-NMR (300 MHz, CD₂Cl₂): δ=0.56 ppm (s, 3H); 0.80 (m, 2H); 0.86 (d, 3H); 0.89 (t, 3H); 1.18 (m, 2H); 2.03 (s, 3H); 3.67 (m, 1H); 4.17 (m, 1H); 4.38 (m, 1H); 4.99 (s, 1H); 5.32 (s, 1H); 6.01 (d, 1H); 6.38 (d, 1H)

EXAMPLE 15

(5Z,7E,22E)-(1S,3R)-25-(1-oxobutyl)-26,27-cyclo-24a-homo-9,10-secocholesta-5,7,10(19),22-tetraene-1,3-diol 131

119. 570 mg of aldehyde 2 is reacted with 780 mg of sulfone 102 analogously to 61., and 606 mg of (5Z,7E)-(1S,3R)-1,3-bis[[dimethyl(1,1-dimethylethyl)silyl]oxy]-23-phenylsulfonyl-25-(2-propyl-1,3-dioxolan-2-yl)-26, 27-cyclo-24a-homo-9, 10-secocholesta-5,7,10(19)-trien-22-ol 128 is obtained as a colorless foam.

120. 600 mg of 128 is reacted analogously to 62., whereby 230 mg of (5Z,7E,22E)-(1S,3R)-1,3-bis[[dimethyl(1,1-dimethylethyl)silyl]oxy]-25-(2-propyl-1,3-dioxolan-2-yl)-26,27-cyclo-24a-homo-9,10-secocholesta-5,7,10(19),22-tetraene 129 and 186 mg of (5Z,7E)-(1S,3R,22S)-1,3-bis[[dimethyl(1,1-dimethylethyl)silyl]oxy]-25-(2-propyl-1,3-dioxolan-2-yl)-26,27-cyclo-24a-homo-9,10-secocholesta-5,7,10(19)-trien-22-ol 130 accumulate in succession as colorless foams.

¹H-NMR (300 MHz, CDCl₃): 129: δ=0.03 ppm (s, 12H); 0.18 (m, 2H); 0.50 (m, 2H); 0.51 (s, 3H); 0.84 (s, 18H); 0.85 (t, 3H); 0.96 (d, 3H); 3.85 (m, 4H); 4.17 (m, 1H); 4.36 (m, 1H); 4.82 (s, 1H); 5.15 (s, 1H); 5.25 (m, 2H); 6.00 (d, 1H); 6.23 (d, 1H)

130: δ=0.03 ppm (s, 12H); 0.19 (m, 2H); 0.50 (s, 3H); 0.56 (m, 2H); 0.87 (t, 3H); 0.88 (d, 3H); 0.89 (s, 18H); 3.57 (m, 1H); 3.86 (m, 4H); 4.17 (m, 1H); 4.37 (m, 1H); 4.81 (s, 1H); 5.17 (s, 1H); 6.00 (d, 1H); 6.23 (d, 1H)

121. 220 mg of 129 is treated analogously to 63, and 73 mg of title compound 131 is obtained as a colorless foam.

¹H-NMR (300 MHz, CD₂Cl₂): δ=0.56 ppm (s, 3H); 0.73 (m, 2H); 0.87 (t, 3H); 1.00 (d, 3H); 1.11 (m, 2H); 2.26 (t, 2H); 4.17 (m, 1H); 4.37 (m, 1H); 4.96 (s, 1H); 5.29 (s, 1H); 5.35 (m, 2H); 6.00 (d, 1H); 6.36 (d, 1H)

EXAMPLE 16

122. (5Z,7E)-(1S,3R,22S)-25-(1-Oxobutyl)-26,27-cyclo-24a-homo-9,10-secocholesta-5,7,10(19)-triene-1,3,22-triol 132

180 mg of 130 is reacted analogously to 63., and 38 mg of the title compound is obtained as a colorless foam.

¹H-NMR (300 MHz, CD₂Cl₂): δ=0.53 ppm (s, 3H); 0.70 (m, 2H); 0.88 (d, 3H); 0.89 (t, 3H); 1.12 (m, 2H); 2.19 (t, 2H); 3.62 (m, 1H); 4.17 (m, 1H); 4.37 (m, 1H); 4.96 (s, 1H); 5.29 (s, 1H); 6.00 (d, 1H); 6.36 (d, 1H)

EXAMPLE 17

(5Z,7E,22E)-(1S,3R)-25-(1-Oxopentyl)-26,27-cyclo-24a-homo-9,10-secocholesta-5,7,10(19),22-tetraene-1,3-diol 136

123. 286 mg of aldehyde 2 is reacted with 390 mg of sulfone 107 analogously to 61., and 325 mg of (5Z,7E)-(1S,3R)-1,3-bis[[dimethyl(1,1-dimethylethyl)silyl]oxy]-23-phenylsulfonyl-25-(2-butyl-1,3-dioxolan-2-yl)-26,27-cyclo-24a-homo-9,10-secocholesta-5,7,10(19)-trien-22-ol 133 is obtained as a colorless foam.

124. 200 mg of 133 is reacted analogously to 62., whereby 85 mg of (5Z,7E,22E)-(1S,3R)-1,3-bis[[dimethyl(1,1-dimethylethyl)silyl]oxy]-25-(2-butyl-1,3-dioxolan-2-yl)-26,27-cyclo-24a-homo-9,10-secocholesta-5,7,10(19),22-tetraene 134 and 70 mg of (5Z,7E)-(1S,3R,22S)-1,3-bis[[dimethyl(1,1-dimethylethyl)silyl]oxy]-25-(2-butyl-1,3-dioxolan-2-yl)-26,27-cyclo-24a-homo-9,10-secocholesta-5,7,10(19)-trien-22-ol 135 accumulate in succession as colorless foams.

$^1$H-NMR (300 MHz, CDCl$_3$): 134: δ=0.03 ppm (s, 12H); 0.18 (m, 2H); 0.51 (m, 2H); 0.52 (s, 3H); 0.86 (s, 18H); 0.87 (t, 3H); 0.99 (d, 3H); 3.85 (m, 4H); 4.17 (m, 1H); 4.36 (m, 1H); 4.82 (s, 1H); 5.15 (s, 1H); 5.18 (m, 2H); 6.00 (d, 1H); 6.22 (d, 1H)

135: δ=0.04 ppm (s, 12H); 0.22 (m, 2H); 0.55 (s, 3H); 0.58 (m, 2H); 0.89 (t, 3H); 0.89 (d, 3H); 0.89 (s, 18H); 3.68 (m, 1H); 3.90 (m, 4H); 4.18 (m, 1H); 4.38 (m, 1H); 4.85 (s, 1H); 5.18 (s, 1H); 6.01 (d, 1H); 6.23 (d, 1H)

125. 43 mg of 134 is treated analogously to 63., and 23 mg of title compound 136 is obtained as a colorless foam.

$^1$H-NMR (300 MHz, CD$_2$Cl$_2$): δ=0.54 ppm (s, 3H); 0.70 (m, 2H); 0.88 (t, 3H); 0.98 (d, 3H); 1.10 (m, 2H); 2.27 (t, 2H); 4.17 (m, 1H); 4.37 (m, 1H); 4.95 (s, 1H); 5.28 (s, 1H); 5.28 (m, 2H); 5.99 (d, 1H); 6.36 (d, 1H)

EXAMPLE 18

126. (5Z,7E)-(1S,3R,22S)-25-(1-Oxopentyl)-26,27-cyclo-24a-homo-9,10-secocholesta-5,7,10(19)-triene-1,3,22-triol 137

48 mg of 135 is reacted analogously to 63., and 23 mg of the title compound is obtained as a colorless foam.

$^1$H-NMR (300 MHz, CD$_2$Cl$_2$): δ=0.55 ppm (s, 3H); 0.71 (m, 2H); 0.87 (d, 3H); 0.89 (t, 3H); 1.12 (m, 4H); 2.23 (t, 2H); 3.64 (m, 1H); 4.16 (m, 1H); 4.36 (m, 1H); 4.94 (s, 1H); 5.28 (s, 1H); 6.00 (d, 1H); 6.35 (d, 1H)

EXAMPLE 19

(5Z,7E,22E)-(1S,3R)-25-(1-Oxohexyl)-26,27-cyclo-24a-homo-9,10-secocholesta-5,7,10(19),22-tetraene-1,3-diol 141

127. 286 mg of aldehyde 2 is reacted with 185 mg of sulfone 112 analogously to 61., and 187 mg of (5Z,7E)-(1S,3R)-1,3-bis[[dimethyl(1,1-dimethylethyl)silyl]oxy]-25-(2-pentyl-1,3-dioxolan-2-yl)-23-phenylsulfonyl-26,27-cyclo-24a-homo-9,10-secocholesta-5,7,10(19)-trien-22-ol 138 is obtained as a colorless foam.

128. 125 mg of 138 is reacted analogously to 62., whereby 35 mg of (5Z,7E,22E)-(1S,3R)-1,3-bis[[dimethyl(1,1-dimethylethyl)silyl]oxy]-25-(2-pentyl-1,3-dioxolan-2-yl)-26,27-cyclo-24a-homo-9,10-secocholesta-5,7,10(19),22-tetraene 139 and 27 mg of (5Z,7E)-(1S,3R,22S)-1,3-bis[[dimethyl(1,1-dimethylethyl)silyl]oxy]-25-(2-pentyl-1,3-dioxolan-2-yl)-26,27-cyclo-24a-homo-9,10-secocholesta-5,7,10(19)-trien-22-ol 140 accumulate in succession as colorless foams.

$^1$H-NMR (300 MHz, CDCl$_3$): 139: δ=0.04 ppm (s, 12H); 0.17 (m, 2H); 0.52 (m, 2H); 0.53 (s, 3H); 0.86 (s, 18H); 0.87 (t, 3H); 0.98 (d, 3H); 3.84 (m, 4H); 4.17 (m, 1H); 4.36 (m, 1H); 4.82 (s, 1H); 5.16 (s, 1H); 5.24 (m, 2H); 6.00 (d, 1H); 6.23 (d, 1H)

140: δ=0.04 ppm (s, 12H); 0.18 (m, 2H); 0.54 (s, 3H); 0.55 (m, 2H); 0.87 (t, 3H); 0.89 (d, 3H); 0.89 (s, 18H); 3.62 (m, 1H); 3.84 (m, 4H); 4.17 (m, 1H); 4.37 (m, 1H); 4.83 (s, 1H); 5.16 (s, 1H); 6.00 (d, 1H); 6.23 (d, 1H) 129. 35 mg of 139 is treated analogously to 63., and 16 mg of title compound 141 is obtained as a colorless foam.

$^1$H-NMR (300 MHz, CD$_2$Cl$_2$): δ=0.56 ppm (s, 3H); 0.70 (m, 2H); 0.88 (t, 3H); 0.98 (d, 3H); 1.09 (m, 2H); 2.23 (t, 2H); 4.17 (m, 1H); 4.36 (m, 1H); 4.97 (s, 1H); 5.28 (s, 1H); 5.29 (m, 2H); 5.99 (d, 1H); 6.34 (d, 1H)

EXAMPLE 20

130. (5Z,7E)-(1S,3R,22S)-25-(1-Oxohexyl)-26,27-cyclo-24a-homo-9,10-secocholesta-5,7,10(19)-triene-1,3,22-triol 142

25 mg of 140 is reacted analogously to 63., and 11 mg of the title compound is obtained as a colorless foam.

$^1$H-NMR (300 MHz, CD$_2$Cl$_2$): δ=0.55 ppm (s, 3H); 0.71 (m, 2H); 0.87 (d, 3H); 0.87 (t, 3H); 1.14 (m, 2H); 2.23 (t, 2H); 3.65 (m, 1H); 4.16 (m, 1H); 4.36 (m, 1H); 4.95 (s, 1H); 5.28 (s, 1H); 6.00 (d, 1H); 6.36 (d, 1H)

EXAMPLE 21

(5Z,7E,22E)-(1S,3R)-25-(1-Oxoheptyl)-26, 27-cyclo-24a-homo-9, 10-secocholesta-5,7,10(19) ,22-tetraene-1,3-diol 146

131. 573 mg of aldehyde 2 is reacted with 630 mg of sulfone 117 analogously to 61., and 599 mg of (5Z,7E)-(1S,3R)-1,3-bis[[dimethyl(1,1-dimethylethyl)silyl]oxy]-25-(2-hexyl-1,3-dioxolan-2-yl)-23-phenylsulfonyl-26, 27-cyclo-24a-homo-9, 10-secocholesta-5,7,10(19)-trien-22-ol 143 is obtained as a colorless foam.

132. 500 mg of 143 is reacted analogously to 62., whereby 156 mg of (5Z,7E,22E)-(1S,3R)-1,3-bis[[dimethyl(1,1-dimethylethyl)silyl]oxy]-25-(2-hexyl-1,3-dioxolan-2-yl)-26,27-cyclo-24a-homo-9,10-secocholesta-5,7,10(19),22-tetraene 144 and 98 mg of (5Z,7E)-(1S,3R,22S)-1,3-bis[[dimethyl(1,1-dimethylethyl)silyl]oxy]-25-(2-hexyl-1,3-dioxolan-2-yl)-26,27-cyclo-24a-homo-9,10-secocholesta-5,7,10(19)-trien-22-ol 145 accumulate in succession as colorless foams.

$^1$H-NMR (300 MHz, CDCl$_3$): 144: δ=0.03 ppm (s, 12H); 0.19 (m, 2H); 0.48 (m, 2H); 0.53 (s, 3H); 0.85 (s, 18H); 0.90 (t, 3H); 0.98 (d, 3H); 3.86 (m, 4H); 4.16 (m, 1H); 4.36 (m, 1H); 4.83 (s, 1H); 5.16 (s, 1H); 5.25 (m, 2H); 6.00 (d, 1H); 6.24 (d, 1H)

145: δ=0.04 ppm (s, 12H); 0.19 (m, 2H); 0.55 (s, 3H); 0.56 (m, 2H); 0.87 (t, 3H); 0.89 (d, 3H); 0.90 (s, 18H); 3.63 (m, 1H); 3.84 (m, 4H); 4.17 (m, 1H); 4.37 (m, 1H); 4.83 (s, 1H); 5.16 (s, 1H); 6.01 (d, 1H); 6.23 (d, 1H)

133. 95 mg of 144 is treated analogously to 63., and 27 mg of title compound 146 is obtained as a colorless foam.

$^1$H-NMR (300 MHz, CD$_2$Cl$_2$): δ=0.54 ppm (s, 3H); 0.71 (m, 2H); 0.86 (t, 3H); 1.00 (d, 3H); 1.12 (m, 2H); 2.22 (t, 2H); 4.16 (m, 1H); 4.36 (m, 1H); 4.94 (s, 1H); 5.25 (s, 1H); 5.25 (m, 2H); 5.99 (d, 1H); 6.34 (d, 1H)

EXAMPLE 22

134. (5Z,7E)-(1S,3R,22S)-25-(1-Oxoheptyl)-26,27-cyclo-24a-homo-9,10-secocholesta-5,7,10(19)-triene-1,3,22-triol 147

43 mg of 145 is reacted analogously to 63., and 14 mg of the title compound is obtained as a colorless foam.

$^1$H-NMR (300 MHz, CD$_2$Cl$_2$): δ=0.55 ppm (s, 3H); 0.73 (m, 2H); 0.85 (d, 3H); 0.86 (t, 3H); 1.13 (m, 2H); 2.21 (t, 2H); 3.64 (m, 1H); 4.16 (m, 1H); 4.36 (m, 1H); 4.94 (s, 1H); 5.28 (s, 1H); 6.00 (d, 1H); 6.35 (d, 1H)

EXAMPLE 23

(5Z,7E,22E)-(1S,3R)-25-(1-Oxooctyl)-26,27-cyclo-24a-homo-9,10-secocholesta-5,7,10(19),22-tetraene-1,3-diol 151

135. 200 mg of aldehyde 2 is reacted with 200 mg of sulfone 122 analogously to 61., and 272 mg of (5Z,7E)-(1S,3R)-1,3-bis[[dimethyl(1,1-dimethylethyl)silyl]oxy]-25-(2-heptyl-1,3-dioxolan-2-yl)-23-phenylsulfonyl-26,27-cyclo-24a-homo-9,10-secocholesta-5,7,10(19)-trien-22-ol 148 is obtained as a colorless foam.

136. 272 mg of 148 is reacted analogously to 62., whereby 78 mg of (5Z,7E,22E)-(1S,3R)-1,3-bis[[dimethyl(1,1-dimethylethyl)silyl]oxy]-25-(2-heptyl-1,3-dioxolan-2-yl)-26,27-cyclo-24a-homo-9,10-secocholesta-5,7,10(19),22-tetraene 149 and 110 mg of (5Z,7E)-(1S,3R,22S)-1,3-bis[[dimethyl(1,1-dimethylethyl)silyl]oxy]-25-(2-heptyl-1,3-dioxolan-2-yl)-26,27-cyclo-24a-homo-9,10-secocholesta-5,7,10(19)trien-22-ol 150 accumulate in succession as colorless foams.

$^1$H-NMR (300 MHz, CDCl$_3$): 149: δ=0.05 ppm (s, 12H); 0.20 (m, 2H); 0.50 (m, 2H); 0.53 (s, 3H); 0.89 (s, 18H); 0.89 (t, 3H); 0.99 (d, 3H); 3.86 (m, 4H); 4.17 (m, 1H); 4.37 (m, 1H); 4.84 (s, 1H); 5.17 (s, 1H); 5.25 (m, 2H); 6.00 (d, 1H); 6.24 (d, 1H)

150: δ=0.03 ppm (s, 12H); 0.18 (m, 2H); 0.52 (s, 3H); 0.52 (m, 2H); 0.88 (t, 3H); 0.88 (d, 3H); 0.89 (s, 18H); 3.60 (m, 1H); 3.83 (m, 4H); 4.17 (m, 1H); 4.37 (m, 1H); 4.82 (s, 1H); 5.17 (s, 1H); 6.00 (d, 1H); 6.24 (d, 1H)

137. 70 mg of 149 is treated analogously to 63., and 27 mg of title compound 151 is obtained as a colorless foam.

$^1$H-NMR (300 MHz, CD$_2$Cl$_2$): δ=0.54 ppm (s, 3H); 0.70 (m, 2H); 0.88 (t, 3H); 0.99 (d, 3H); 1.10 (m, 2H); 2.22 (t, 2H); 4.17 (m, 1H); 4.37 (m, 1H); 4.95 (s, 1H); 5.29 (s, 1H); 5.30 (m, 2H); 5.99 (d, 1H); 6.35 (d, 1H)

EXAMPLE 24

138. (5Z,7E)-(1S,3R,22S)-25-(1-Oxooctyl)-26,27-cyclo-24a-homo-9,10-secocholesta-5,7,10(19)-triene-1,3,22-triol 152

110 mg of 150 is reacted analogously to 63., and 38 mg of the title compound is obtained as a colorless foam.

$^1$H-NMR (300 MHz, CD$_2$Cl$_2$): δ=0.54 ppm (s, 3H); 0.72 (m, 2H); 0.89 (d, 3H); 0.89 (t, 3H); 1.12 (m, 2H); 2.22 (t, 2H); 3.63 (m, 1H); 4.17 (m, 1H); 4.38 (m, 1H); 4.96 (s, 1H); 5.29 (s, 1H); 6.01 (d, 1H); 6.37 (d, 1H)

Starting Materials in the 24-Hydroxymethylene-24a,24b-dihomo Series 139. (E)-4-[1-(2-Methyl-1,3-dioxolan-2-yl)cyclopropyl]-3-buten-2-one 153

13.8 g of lithium chloride (anhydrous) is introduced into 120 ml of acetonitrile under nitrogen, and 49.8 ml of oxopropylphosphonic acid dimethyl ester, 51.3 ml of diisopropylethylamine and 5.4 g of aldehyde 7 are added in succession. It is stirred for 18 hours at room temperature, and then sodium chloride solution is added. It is extracted with ethyl acetate, washed with sodium chloride solution and dried on sodium sulfate. The residue is chromatographed on silica gel with ethyl acetate/hexane, whereby 5.3 g of the title compound accumulates as a colorless oil.

$^1$H-NMR (300 MHz, CDCl$_3$): δ=0.75 ppm (m, 2H); 1.10 (m, 2H); 1.42 (s, 3H); 2.25 (s, 3H); 3.96 (m, 4H); 6.00 (d, 1H); 7.10 (d, 1H)

140. 4-[1-(2-Methyl-1,3-dioxolan-2-yl)cyclopropyl]butan-2-one 154

1.23 g of 153 is dissolved in THF, and 200 mg of platinum(IV) oxide is added in an argon stream. Using a hydrogenating apparatus, it is hydrogenated until no more hydrogen is consumed, flushed with nitrogen, filtered and concentrated by evaporation. The residue is chromatographed on silica gel with ethyl acetate/hexane, whereby 1.19 g of title compound 154 accumulates as a colorless oil.

$^1$H-NMR (300 MHz, CDCl$_3$): δ=0.23 ppm (m, 2H); 0.64 (m, 2H); 1.38 (s, 3H); 1.70 (dd, 2H); 2.15 (s, 3H); 2.64 (dd, 2H); 3.89 (m, 4H)

141. (E)-4-[1-(2-Propyl-1,3-dioxolan-2-yl)cyclopropyl]-3-buten-2-one 155

2.0 g of aldehyde 17 is reacted analogously to 139., and 2.1 g of title compound 155 is obtained as a colorless oil.

$^1$H-NMR (300 MHz, CDCl$_3$): δ=0.70 ppm (m, 2H); 0.90 (t, 3H); 1.09 (m, 2H); 1.40 (m, 2H); 2.27 (s, 3H); 3.97 (m, 4H); 5.92 (d, 1H); 7.18 (d, 1H)

142. 4-[1-(2-Propyl-1,3-dioxolan-2-yl)cyclopropyl]butan-2-one 156

740 mg of 155 is reacted analogously to 140., and 709 mg of title compound 156 is obtained as a colorless oil.

$^1$H-NMR (300 MHz, CDCl$_3$): δ=0.19 ppm (m, 2H); 0.60 (m, 2H); 0.91 (t, 3H); 2.13 (s, 3H); 2.65 (t, 2H); 3.90 (m, 4H)

143. (E)-4-[1-(2-Butyl-1,3-dioxolan-2-yl)cyclopropyl]-3-buten-2-one 157

3.0 g of aldehyde 27 is reacted analogously to 139., and 2.7 g of title compound 157 is obtained as a colorless oil.

$^1$H-NMR (300 MHz, CDCl$_3$): δ=0.72 ppm (m, 2H); 0.90 (t, 3H); 1.08 (m, 2H); 1.31 (m, 4H); 1.78 (m, 2H); 2.26 (s, 3H); 3.97 (m, 4H); 5.91 (d, 1H); 7.17 (d, 1H)

144. 4-[1-(2-Butyl-1,3-dioxolan-2-yl)cyclopropyl]butan-2-one 1.6 g of 157 is reacted analogously to 140., and 1.42 g of title compound 158 is obtained as a colorless oil.

$^1$H-NMR (300 MHz, CDCl$_3$): δ=0.19 ppm (m, 2H); 0.61 (m, 2H); 0.90 (t, 3H); 1.32 (m, 4H); 1.67 (m, 2H); 1.76 (m, 2H); 2.15 (s, 3H); 2.68 (t, 2H); 3.90 (m, 4H)

145. (E)-4-[1-(2-Pentyl-1,3-dioxolan-2-yl)cyclopropyl]-3-buten-2-one 159

2.5 g of aldehyde 37 is reacted analogously to 139., and 2.9 g of title compound 159 is obtained as a colorless oil.

$^1$H-NMR (300 MHz, CDCl$_3$): δ=0.71 ppm (m, 2H); 0.90 (t, 3H); 1.08 (m, 2H); 1.30 (m, 6H); 1.77 (m, 2H); 2.27 (s, 3H); 3.97 (m, 4H); 5.92 (d, 1H); 7.18 (d, 1H)

146. 4-[1-(2-Pentyl-1,3-dioxolan-2-yl)cyclopropyl]butan-2-one 160

1.7 g of 159 is reacted analogously to 140., and 1.51 g of title compound 160 is obtained as a colorless oil.

$^1$H-NMR (300 MHz, CDCl$_3$): δ=0.19 ppm (m, 2H); 0.61 (m, 2H); 0.90 (t, 3H); 1.32 (m, 6H); 1.75 (m, 2H); 2.17 (s, 3H); 2.64 (m, 2H); 3.89 (m, 4H)

147. (E)-4-[1-(2-Hexyl-1,3-dioxolan-2-yl)cyclopropyl]-3-buten-2-one 161

3.44 g of aldehyde 47 is reacted analogously to 139., and 2.3 g of title compound 161 is obtained as a colorless oil.

$^1$H-NMR (300 MHz, CDCl$_3$): δ=0.72 ppm (m, 2H); 0.89 (t, 3H); 1.08 (m, 2H); 1.29 (m, 8H); 1.77 (m, 2H); 2.27 (s, 3H); 3.96 (m, 4H); 5.92 (d, 1H); 7.18 (d, 1H)

148. 4-[1-(2-Hexyl-1,3-dioxolan-2-yl)cyclopropyl]butan-2-one 162

800 mg of 161 is reacted analogously to 140., and 710 g of title compound 162 is obtained as a colorless oil.

$^1$H-NMR (300 MHz, CDCl$_3$): δ=0.18 ppm (m, 2H); 0.59 (m, 2H); 0.89 (t, 3H); 1.29 (m, 8H); 1.63 (m, 2H); 1.74 (m, 2H); 2.13 (s, 3H); 2.65 (m, 2H); 3.90 (m, 4H)

EXAMPLE 25

(5Z,7E,22E)-(1S,3R,24R)-25-Acetyl-26,27-cyclo-24a,24b-dihomo-9,10-secocholesta-5,7,10(19),22-tetraene-1,3,24-triol 168a and (5Z,7E,22E)-(1S,3R,24S)-25-acetyl-26,27-cyclo-24a,24b-dihomo-9,10-secocholesta-5,7,10(19),22-tetraene-1,3,24-triol 168b 149. A solution of 1 mmol of lithium diisopropylamide in 5 ml of THF is produced, cooled to −78° C., and 202 mg of ketone 154 is added in drops to 1 ml of THF. It is stirred for 30 minutes at −78° C., and then 229 mg of aldehyde 2 is added in drops to 1 ml of THF. It is stirred for another 30 minutes at this temperature, then quenched with sodium chloride solution, extracted with ethyl acetate, the organic phase is washed with sodium chloride solution, dried on sodium sulfate and concentrated by evaporation. Chromatography of the residue on silica gel with ethyl acetate/hexane yields 189 mg of (5Z,7E)-(1S,3R)-1,3-bis[[dimethyl(1,1-dimethylethyl)silyl]oxy]-22-hydroxy-25-(2-methyl-1,3-dioxolan-2-yl)-26,27-cyclo-24a,24b-dihomo-9,10-secocholesta-5,7,10(19)-trien-24-one 163 as a colorless foam, which is immediately further reacted.

150. A solution of 60 mg of 163, 0.2 ml of acetic anhydride, 0.11 ml of triethylamine and a spatula-tip full of 4-dimethylaminopyridine (DMAP) is stirred for 2 hours under nitrogen at room temperature. Sodium bicarbonate solution is now added, extracted with ethyl acetate, washed with sodium chloride solution, dried on sodium sulfate and concentrated by evaporation, whereby 172 mg of (5Z,7E)-(1S,3R)-22-acetoxy-1,3-bis[[dimethyl(1,1-dimethylethyl)silyl]oxy]-25-(2-methyl-1,3-dioxolan-2-yl)-26,27-cyclo-24a,24b-dihomo-9,10-secocholesta-5,7,10(19)-trien-24-one 164 is obtained as a colorless foam, which is immediately further reacted.

151. 172 mg of 164 is dissolved in 10 ml of toluene, 1 ml of diazabicycloundecane (DBU) is added under nitrogen, and it is heated for 30 minutes to 40° C. Then, it is concentrated by evaporation, and the residue is chromatographed on silica gel with ethyl acetate/hexane, whereby 129 mg of (5Z,7E,22E)-(1S,3R)-1,3-bis[[dimethyl(1,1-dimethylethyl)silyl]oxy]-25-(2-methyl-1,3-dioxolan-2-yl)-26,27-cyclo-24a,24b-dihomo-9,10-secocholesta-5,7,10(19),22-tetraen-24-one 165 accumulates as a colorless foam.

$^1$H-NMR (300 MHz, CD$_2$Cl$_2$): δ=0.04 ppm (s, 12H); 0.21 (m, 2H); 0.54 (s, 3H); 0.60 (m, 2H); 0.86 (s, 18H); 1.09 (d, 3H); 1.33 (s, 3H); 3.83 (m, 4H); 4.17 (m, 1H); 4.35 (m, 1H); 4.82 (s, 1H); 5.16 (s, 1H); 5.94 (d, 1H); 6.01 (d, 1H); 6.23 (d, 1H); 663 (dd, 1H)

152. 130 mg of 165 is dissolved in 1 ml of THF, and 5 ml of methanol, 75 mg of cerium trichloride (heptahydrate), and, after 10 minutes, 8 mg of sodium borohydride are added at 0° C. under nitrogen. It is stirred for 30 minutes at 0° C., and then quenched with saturated ammonium chloride solution. It is extracted with ethyl acetate, dried on sodium sulfate and concentrated by evaporation. The residue is chromatographed on silica gel with ethyl acetate/hexane, whereby 60 mg of (5Z,7E,22E)-(1S,3R,24R)-1,3-bis[[dimethyl(1,1-dimethylethyl)silyl]oxy]-25-(2-methyl-1,3-dioxolan-2-yl)-26,27-cyclo-24a,24b-dihomo-9,10-secocholesta-,7,10(19),22-tetraen-24-ol 166a and 32 mg of (5Z,7E,22E)-(1S,3R,24S)-1,3-bis[[dimethyl(1,1-dimethylethyl)silyl]oxy]-25-(2-methyl-1,3-dioxolan-2-yl)-26,27-cyclo-24a,24b-dihomo-9,10-secocholesta-5,7,10(19),22-tetraen-24-ol 166b are obtained in succession as colorless foams.

$^1$H-NMR (300 MHz, CD$_2$Cl$_2$): 166a: δ=0.04 ppm (s, 12H); 0.22 (m, 2H); 0.53 (s, 3H); 0.56 (m, 2H); 0.86 (s, 18H); 1.01 (d, 3H); 1.32 (s, 3H); 3.83 (m, 4H); 3.91 (m, 1H); 4.17 (m, 1H); 4.36 (m, 1H); 4.82 (s, 1H); 5.16 (s, 1H); 5.33 (dd, 1H); 5.45 (dd, 1H); 6.00 (d, 1H); 6.23 (d, 1H)

166b: $^1$H-NMR (300 MHz, CD$_2$Cl$_2$): δ=0.03 ppm (s, 12H); 0.22 (m, 2H); 0.53 (s, 3H); 0.56 (m, 2H); 0.86 (s, 18H); 1.01 (d, 3H); 1.32 (s, 3H); 3.82 (m, 4H); 3.85 (m, 1H); 4.17 (m, 1H); 4.36 (m, 1H); 4.82 (s, 1H); 5.16 (s, 1H); 5.30 (dd, 1H); 5.41 (dd, 1H); 6.00 (d, 1H); 6.23 (d, 1H)

153. 300 mg of silica gel is introduced into 10 ml of dichloromethane, and 0.3 ml of aqueous oxalic acid solution (10%) is added under nitrogen. It is stirred for 5 minutes at room temperature, and then 40 mg of 166a is added in drops to 2 ml of dichloromethane. It is stirred for one hour at room temperature, sodium bicarbonate is added, it is filtered off and concentrated by evaporation, whereby 39 mg of (5Z,7E,22E)-(1S,3R,24R)-25-acetyl-1,3-bis[[dimethyl(1,1-dimethylethyl)silyl]oxy]-26,27-cyclo-24a,24b-dihomo-9,10-secocholesta-5,7,10(19),22-tetraen-24-ol 167a accumulates as a colorless foam, which is immediately further reacted.

154. 38 mg of 167a is dissolved in 5 ml of THF, 150 mg of tetrabutylammonium fluoride (hydrate) is added, and it is stirred under nitrogen for 12 more hours at room temperature. Then, sodium chloride solution is added, extracted with ethyl acetate, washed with sodium chloride solution, dried on sodium sulfate and concentrated by evaporation. The residue is chromatographed on silica gel with ethyl acetate/hexane, whereby 9 mg of title compound 168a accumulates as a colorless foam.

$^1$H-NMR (300 MHz, CD$_2$Cl$_2$): δ=0.55 ppm (s, 3H); 0.78 (m, 2H); 1.02 (d, 3H); 1.18 (m, 2H); 1.93 (s, 3H); 3.92 (m, 1H); 4.16 (m, 1H); 4.37 (m, 1H); 4.95 (s, 1H); 5.28 (s, 1H); 5.36 (dd, 1H); 5.58 (dd, 1H); 5.99 (d, 1H); 6.31 (d, 1H)

155. 32 mg of 166b is reacted analogously to 153., whereby 24 mg of (5Z,7E,22E)-(1S,3R,24S)-25-acetyl-1,3-bis[[dimethyl(1,1-dimethylethyl)silyl]oxy]-26,27-cyclo-24a,24b-dihomo-9,10-secocholesta-5,7,10(19),22-tetraen-24-ol 167b is obtained as a colorless foam, which is immediately further reacted.

156. 24 mg of 167b is reacted analogously to 154., whereby 6 mg of title compound 168b accumulates as a colorless foam.

$^1$H-NMR (300 MHz, CD$_2$Cl$_2$) δ=0.55 ppm (s, 3H); 0.77 (m, 2H); 1.03 (d, 3H); 1.20 (m, 2H); 1.93 (s, 3H); 3.91 (m, 1H); 4.16 (m, 1H); 4.37 (m, 1H); 4.95 (s, 1H); 5.28 (s, 1H); 5.32 (dd, 1H); 5.45 (dd, 1H); 5.99 (d, 1H); 6.31 (d, 1H)

EXAMPLE 26

157. (5Z,7E,22E)-(1S,3R,24R)-25-Acetyl-24-methoxy-26,27-cyclo-24a,24b-dihomo-9,10-secocholesta-5,7,10(19),22-tetraene-1,3-diol 169a and (5Z,7E,22E)-(1S,3R,24S)-25-acetyl-24-methoxy-26,27-cyclo-24a,24b-dihomo-9,10-secocholesta-5,7,10(19),22-tetraene-1,3-diol 169b 58 mg of 166a is dissolved in 5 ml of dichloromethane/methanol (1:1), 380 mg of Dowex ion exchanger is added, and it is stirred for 12 hours under nitrogen at room temperature. It is then filtered off, the filtrate is washed with sodium bicarbonate solution, dried on sodium sulfate and concentrated by evaporation. The residue is chromatographed on silica gel with ethyl acetate/hexane, whereby 32 mg of a diastereomer mixture accumulates. By HPLC separation, 11 mg of title compound 169b and 13 mg of title compound 169a are then obtained in succession as colorless foams.

$^1$H-NMR (300 MHz, CD$_2$Cl$_2$): 169a: δ=0.56 ppm (s, 3H); 0.72 (m, 2H); 1.07 (d, 3H); 1.15 (m, 2H); 1.97 (s, 3H); 3.19 (s, 3H); 3.39 (m, 1H); 4.18 (m, 1H); 4.38 (m, 1H); 4.96 (s, 1H); 5.12 (dd, 1H); 5.29 (s, 1H); 5.55 (dd, 1H); 6.00 (d, 1H); 6.35 (d, 1H)

169b: δ=0.56 ppm (s, 3H); 0.72 (m, 2H); 1.07 (d, 3H); 1.15 (m, 2H); 1.96 (s, 3H); 3.18 (s, 3H); 3.39 (m, 1H); 4.17 (m, 1H); 4.37 (m, 1H); 4.96 (s, 1H); 5.13 (dd, 1H); 5.29 (s, 1H); 5.55 (dd, 1H); 6.00 (d, 1H); 6.36 (d, 1H)

EXAMPLE 27

(5Z,7E,22E)-(1S,3R,24R)-25-(1-Oxobutyl)-26,27-cyclo-24a,24b-dihomo-9,10-secocholesta-5,7,10(19),22-tetraene-1,3,24-triol 175a and (5Z,7E,22E)-(1S,3R,24S)-25-(1-oxobutyl)-26,27-cyclo-24a,24b-dihomo-9,10-secocholesta-5,7,10(19),22-tetraene-1,3,24-triol 175b 158. 700 mg of ketone 156 is reacted with 350 mg of aldehyde 2 analogously to 149., and 490 mg of (5Z,7E)-(1S,3R)-1,3-bis[[dimethyl(1,1-dimethylethyl)silyl]oxy]-22-hydroxy-25-(2-propyl-1,3-dioxolan-2-yl)-26,27-cyclo-24a,24b-dihomo-9,10-secocholesta-5,7,10(19)-trien-24-one 170 is obtained as a colorless foam, which is immediately further reacted.

159. A solution of 490 mg of 170 is reacted analogously to 150., whereby 505 mg of (5Z,7E)-(1S,3R)-22-acetoxy-1,3-bis[[dimethyl(1,1-dimethylethyl)silyl]oxy]-25-(2-propyl-1,3-dioxolan-2-yl)-26,27-cyclo-24a,24b-dihomo-9,10-secocholesta-5,7,10(19)-trien-24-one 171 is obtained as a colorless foam, which is immediately further reacted.

160. 505 mg of 171 is reacted analogously to 151., whereby 290 mg of (5Z,7E,22E)-(1S,3R)-1,3-bis[[dimethyl(1,1-dimethylethyl)silyl]oxy]-25-(2-propyl-1,3-dioxolan-2-yl)-26,27-cyclo-24a,24b-dihomo-9,10-secocholesta-5,7,10(19),22-tetraen-24-one 172 accumulates as a colorless foam.

$^1$H-NMR (300 MHz, CD$_2$Cl$_2$): δ=0.06 ppm (s, 12H); 0.19 (m, 2H); 0.54 (s, 3H); 0.58 (m, 2H); 0.86 (s, 18H); 0.92 (t, 3H); 1.08 (d, 3H); 3.84 (m, 4H); 4.17 (m, 1H); 4.36 (m, 1H); 4.83 (s, 1H); 5.16 (s, 1H); 5.96 (d, 1H); 6.02 (d, 1H); 6.24 (d, 1H); 6.64 (dd, 1H)

161. 350 mg of 172 is reacted analogously to 152., and after chromatography on silica gel with ethyl acetate/hexane, 160 mg of (5Z,7E,22E)-(1S,3R,24R)-1,3-bis[[dimethyl(1,1-dimethylethyl)silyl]oxy]-25-(2-propyl-1,3-dioxolan-2-yl)-26,27-cyclo-24a,24b-dihomo-9,10-secocholesta-5,7,10(19),22-tetraen-24-ol 173a and 109 mg of (5Z,7E,22E)-(1S,3R,24S)-1,3-bis[[dimethyl(1,1-dimethylethyl)silyl]oxy]-25-(2-propyl-1,3-dioxolan-2-yl)-26,27-cyclo-24a,24b-dihomo-9,10-secocholesta-5,7,10(19),22-tetraen-24-ol 173b are obtained in succession as colorless foams.

$^1$H-NMR (300 MHz, CD$_2$Cl$_2$): 173a: δ=0.03 ppm (s, 12H); 0.18 (m, 2H); 0.53 (s, 3H); 0.55 (m, 2H); 0.87 (s, 18H); 0.90 (t, 3H); 1.02 (d, 3H); 3.83 (m, 4H); 3.90 (m, 1H); 4.16 (m, 1H); 4.35 (m, 1H); 4.83 (s, 1H); 5.15 (s, 1H); 5.31 (dd, 1H); 5.43 (dd, 1H); 6.00 (d, 1H); 6.23 (d, 1H)

173b: $^1$H-NMR (300 MHz, CD$_2$Cl$_2$): δ=0.03 ppm (s, 12H); 0.17 (m, 2H); 0.54 (s, 3H); 0.55 (m, 2H); 0.87 (s, 18H); 0.90 (t, 3H); 1.02 (d, 3H); 3.84 (m, 4H); 3.85 (m, 1H); 4.16 (m, 1H); 436 (m, 1H); 4.83 (s, 1H); 5.15 (s, 1H); 5.30 (dd, 1H); 5.41 (dd, 1H); 6.00 (d, 1H); 6.23 (d, 1H)

162. 85 mg of 173a is reacted analogously to 153., whereby 59 mg of (5Z,7E,22E)-(1S,3R,24R)-1,3-bis[[dimethyl(1,1-dimethylethyl)silyl]oxy]-25-(1-oxobutyl)-26,27-cyclo-24a,24b-dihomo-9,10-secocholesta-5,7,10(19),22-tetraen-24-ol 174a accumulates as a colorless foam, which is immediately further reacted.

163. 59 mg of 174a is reacted analogously to 154., whereby 19 mg of title compound 175a accumulates as a colorless foam.

$^1$H-NMR (300 MHz, CD$_2$Cl$_2$): δ=0.55 ppm (s, 3H); 0.72 (m, 2H); 0.89 (t, 3H); 1.02 (d, 3H); 1.16 (m, 2H); 2.18 (t, 2H); 3.92 (m, 1H); 4.17 (m, 1H); 4.37 (m, 1H); 4.95 (s, 1H); 5.29 (s, 1H); 5.35 (dd, 1H); 5.51 (dd, 1H); 5.99 (d, 1H); 6.34 (d, 1H)

164. 61 mg of 173b is reacted analogously to 153., whereby 45 mg of (5Z,7E,22E)-(1S,3R,24S)-1,3-bis[[dimethyl(1,1-dimethylethyl)silyl]oxy]-25-(1-oxobutyl)-26,27-cyclo-24a,24b-dihomo-9,10-secocholesta-5,7,10(19),22-tetraen-24-ol 174b is obtained as a colorless foam, which is immediately further reacted.

165. 45 mg of 174b is reacted analogously to 154., whereby 21 mg of title compound 175b accumulates as a colorless foam.

$^1$H-NMR (300 MHz, CD$_2$Cl$_2$): δ=0.56 ppm (s, 3H); 0.72 (m, 2H); 0.88 (t, 3H); 1.02 (d, 3H); 1.15 (m, 2H); 2.20 (t, 2H); 3.92 (m, 1H); 4.18 (m, 1H); 4.38 (m, 1H); 4.95 (s, 1H); 5.28 (s, 1H); 5.33 (dd, 1H); 5.46 (dd, 1H); 6.00 (d, 1H); 6.34 (d, 1H)

EXAMPLE 28

166. (5Z,7E,22E)-(1S,3R,24R)-24-Methoxy-25-(1-oxobutyl)-26,27-cyclo-24a,24b-dihomo-9,10-secocholesta-5,7,10(19,22-tetraene-1,3-diol 176a and (5Z,7E,22E)-(1S,3R,24S)-24-methoxy-25-(1-oxobutyl)-26,27-cyclo-24a, 24b-dihomo-9,10-secocholesta-5,7,10(19),22-tetraene-1,3-diol 176b 71 mg of 173a is reacted analogously to 157., and 21 mg of title compound 176b and 18 mg of title compound 176a are obtained as colorless foams.

$^1$H-NMR (300 MHz, CD$_2$Cl$_2$): 173a: δ=0.54 ppm (s, 3H); 0.70 (m, 2H); 0.86 (t, 3H); 1.06 (d, 3H); 1.13 (m, 2H); 3.15

(s, 3H); 3.38 (m, 1H); 4.16 (m, 1H); 4.36 (m, 1H); 4.96 (s, 1H); 5.14 (dd, 1H); 5.28 (s, 1H); 5.53 (dd, 1H); 5.99 (d, 1H); 6.35 (d, 1H)

173b: δ=0.55 ppm (s, 3H); 0.70 (m, 2H); 0.87 (t, 3H); 1.06 (d, 3H); 1.14 (m, 2H); 3.16 (s, 3H); 3.39 (m, 1H); 4.17 (m, 1H); 4.37 (m, 1H); 4.96 (s, 1H); 5.14 (dd, 1H); 5.29 (s, 1H); 5.52 (dd, 1H); 6.00 (d, 1H); 6.35 (d, 1H)

EXAMPLE 29

(5Z,7E,22E)-(1S,3R,24R)-25-(1-Oxopentyl)-26,27-cyclo-24a,24b-dihomo-9,10-secocholesta-5,7,10(19), 22-tetraene-1,3,24-triol 182a and (5Z,7E,22E)-(1S, 3R,24S)-25-(1-oxopentyl)-26,27-cyclo-24a,24b-dihomo-9,10-secocholesta-5,7,10(19),22-tetraene-1, 3,24-triol 182b 167. 100 mg of ketone 158 is reacted with 200 mg of aldehyde 2 analogously to 149., and 120 mg of (5Z,7E)-(1S,3R)-1,3-bis[[dimethyl(1,1-dimethylethyl)silyl]oxy]-25-(2-butyl-1,3-dioxolan-2-yl)-22-hydroxy-26,27-cyclo-24a, 24b-dihomo-9,10-secocholesta-5,7,10(19)-trien-24-one 177 is obtained as a colorless foam, which is immediately further reacted.

168. A solution of 120 mg of 177 is reacted analogously to 150., whereby 134 mg of (5Z,7E)-(1S,3R)-22-acetoxy-1, 3-bis[[dimethyl(1,1-dimethylethyl)silyl]oxy]-25-(2-butyl-1, 3-dioxolan-2-yl)-26,27-cyclo-24a,24b-dihomo-9,10-secocholesta-5,7,10(19)-trien-24-one 178 is obtained as a colorless foam, which is immediately further reacted.

169. 134 mg of 178 is reacted analogously to 151., whereby 72 mg of (5Z,7E,22E)-(1S,3R)-1,3-bis[[dimethyl(1,1-dimethylethyl)silyl]oxy]-25-(2-butyl-1,3-dioxolan-2-yl)-26,27-cyclo-24a,24b-dihomo-9,10-secocholesta-5,7,10 (19),22-tetraen-24-one 179 accumulates as a colorless foam.
$^1$H-NMR (300 MHz, CD$_2$Cl$_2$): δ=0.03 ppm (s, 12H); 0.18 (m, 2H); 0.56 (s, 3H); 0.57 (m, 2H); 0.89 (s, 18H); 0.90 (t, 3H); 1.09 (d, 3H); 3.85 (m, 4H); 4.17 (m, 1H); 4.36 (m, 1H); 4.85 (s, 1H); 5.16 (s, 1H); 5.96 (d, 1H); 5.98 (d, 1H); 6.24 (d, 1H); 6.65 (dd, 1H)

170. 70 mg of 179 is reacted analogously to 152., and after chromatography on silica gel with ethyl acetate/hexane, 28 mg of (5Z,7E,22E)-(1S,3R,24R)-1,3-bis[[dimethyl(1,1-dimethylethyl)silyl]oxy]-25-(2-butyl-1,3-dioxolan-2-yl)-26, 27-cyclo-24a,24b-dihomo-9,10-secocholesta-5,7,10(19),22-tetraen-24-ol 180a and 29 mg of (5Z,7E,22E)-(1S,3R,24S)-1,3-bis[[dimethyl(1,1-dimethylethyl)silyl]oxy]-25-(2-butyl-1,3-dioxolan-2-yl)-26,27-cyclo-24a,24b-dihomo-9,10-secocholesta-5,7,10(19),22-tetraen-24-ol 180b are obtained in succession as colorless foams.
$^1$H-NMR (300 MHz, CD$_2$Cl$_2$): 180a: δ=0.05 ppm (s, 12H); 0.17 (m, 2H); 0.54 (s, 3H); 0.55 (m, 2H); 0.89 (s, 18H); 0.90 (t, 3H); 1.02 (d, 3H); 3.85 (m, 4H); 3.92 (m, 1H); 4.17 (m, 1H); 4.37 (m, 1H); 4.84 (s, 1H); 5.17 (s, 1H); 5.32 (dd, 1H); 5.46 (dd, 1H); 6.01 (d, 1H); 6.25 (d, 1H)

180b: $^1$H-NMR (300 MHz, CD$_2$Cl$_2$): δ=0.05 ppm (s, 12H); 0.18 (m, 2H); 0.54 (s, 3H); 0.55 (m, 2H); 0.89 (s, 18H); 0.90 (t, 3H); 1.02 (d, 3H); 3.84 (m, 4H); 3.90 (m, 1H); 4.17 (m, 1H); 4.37 (m, 1H); 4.84 (s, 1H); 5.16 (s, 1H); 5.32 (dd, 1H); 5.42 (dd, 1H); 6.01 (d, 1H); 6.25 (d, 1H)

171. 25 mg of 180a is reacted analogously to 153., whereby 19 mg of (5Z,7E,22E)-(1S,3R,24R)-1,3-bis[[dimethyl(1,1-dimethylethyl) silyl] oxy]-25-(1-oxopentyl)-26, 27-cyclo-24a, 24b-dihomo-9,10-secocholesta-5,7,10(19) ,22-tetraen-24-ol 181a accumulates as a colorless foam, which is immediately further reacted.

172. 19 mg of 181a is reacted analogously to 154., whereby 5 mg of title compound 182a accumulates as a colorless foam.
$^1$H-NMR (300 MHz, CD$_2$Cl$_2$): δ=0.54 ppm (s, 3H); 0.73 (m, 2H); 0.86 (t, 3H); 1.01 (d, 3H); 1.14 (m, 2H); 2.19 (t, 2H); 3.93 (m, 1H); 4.16 (m, 1H); 4.36 (m, 1H); 4.94 (s, 1H); 5.28 (s, 1H); 5.34 (dd, 1H); 5.48 (dd, 1H); 6.00 (d, 1H); 6.34 (d, 1H)

173. 23 mg of 180b is reacted analogously to 1534., whereby 20 mg of (5Z,7E,22E)-(1S,3R,24S)-1,3-bis[[dimethyl(1,1-dimethylethyl)silyl]oxy]-25-(1-oxopentyl)-26,27-cyclo-24a,24b-dihomo-9,10-secocholesta-5,7,10(19),22-tetraen-24-ol 181b is obtained as a colorless foam, which is immediately further reacted.

174. 20 mg of 181b is reacted analogously to 1545., whereby 4.5 mg of title compound 182b accumulates as a colorless foam.
$^1$H-NMR (300 MHz, CD$_2$Cl$_2$): δ=0.54 ppm (s, 3H); 0.72 (m, 2H); 0.88 (t, 3H); 1.01 (d, 3H); 1.13 (m, 2H); 2.19 (t, 2H); 3.90 (m, 1H); 4.17 (m, 1H); 4.37 (m, 1H); 4.95 (s, 1H); 5.28 (s, 1H); 5.31 (dd, 1H); 5.45 (dd, 1H); 6.00 (d, 1H); 6.34 (d, 1H)

EXAMPLE 30

(5Z,7E,22E)-(1S,3R,24R)-25-(1-Oxohexyl)-26,27-cyclo-24a,24b-dihomo-9,10-secocholesta-5,7,10(19), 22-tetraene-1,3,24-triol 188a and (5Z,7E,22E)-(1S, 3R,24S)-25-(1-oxohexyl)-26,27-cyclo-24a,24b-dihomo-9,10-secocholesta-5,7,10(19),22-tetraene-1, 3,24-triol 188b 175. 180 mg of ketone 160 is reacted with 406 mg of aldehyde 2 analogously to 149., and 195 mg of (5Z,7E)-(1S,3R)-1,3-bis[[dimethyl(1,1-dimethylethyl)silyl]oxy]-22-hydroxy-25-(2-pentyl-1,3-dioxolan-2-yl)-26,27-cyclo-24a, 24b-dihomo-9,10-secocholesta-5,7,10(19)-trien-24-one 183 is obtained as a colorless foam, which is immediately further reacted.

176. A solution of 195 mg of 183 is reacted analogously to 150., whereby 210 mg of (5Z,7E)-(1S,3R)-22-acetoxy-1, 3-bis[[dimethyl(1,1-dimethylethyl)silyl]oxy]-25-(2-pentyl-1,3-dioxolan-2-yl)-26,27-cyclo-24a,24b-dihomo-9,10-secocholesta-5,7,10(19)-trien-24-one 184 is obtained as a colorless foam, which is immediately further reacted.

177. 210 mg of 184 is reacted analogously to 151., whereby 165 mg of (5Z,7E,22E)-(1S,3R)-1,3-bis[[dimethyl(1,1-dimethylethyl)silyl]oxy]-25-(2-pentyl-1,3-dioxolan-2-yl)-26,27-cyclo-24a,24b-dihomo-9,10-secocholesta-5,7,10 (19),22-tetraen-24-one 185 accumulates as a colorless foam.
$^1$H-NMR (300 MHz, CD$_2$Cl$_2$): δ=0.05 ppm (s, 12H); 0.17 (m, 2H); 0.56 (s, 3H); 0.57 (m, 2H); 0.88 (s, 18H); 0.89 (t, 3H); 1.08 (d, 3H); 3.83 (m, 4H); 4.16 (m, 1H); 4.36 (m, 1H); 4.83 (s, 1H); 5.15 (s, 1H); 5.94 (d, 1H); 6.00 (d, 1H); 6.24 (d, 1H); 6.64 (dd, 1H)

178. 165 mg of 185 is reacted analogously to 152., and after chromatography on silica gel with ethyl acetate/hexane, 46 mg of (5Z,7E,22E)-(1S,3R,24R)-1,3-bis[[dimethyl(1,1-dimethylethyl)silyl]oxy]-25-(2-pentyl-1,3-dioxolan-2-yl)-26,27-cyclo-24a,24b-dihomo-9,10-secocholesta-5,7,10 (19),22-tetraen-24-ol 186a and 35 mg of (5Z,7E,22E)-(1S, 3R,24S)-1,3-bis[[dimethyl(1,1-dimethylethyl)silyl]oxy]-25-(2-pentyl-1,3-dioxolan-2-yl)-26,27-cyclo-24a,24b-dihomo-9,10-secocholesta-5,7,10(19),22-tetraen-24-ol 186b are obtained in succession as colorless foams.
$^1$H-NMR (300 MHz, CD$_2$Cl$_2$): 186a: δ=0.05 ppm (s, 12H); 0.17 (m, 2H); 0.54 (s, 3H); 0.55 (m, 2H); 0.88 (s, 18H); 0.89 (t, 3H); 1.03 (d, 3H); 3.85 (m, 4H); 3.91 (m, 1H); 4.17 (m, 1H); 4.36 (m, 1H); 4.84 (s, 1H); 5.17 (s, 1H); 5.33 (dd, 1H); 5.47 (dd, 1H); 6.01 (d, 1H); 6.25 (d, 1H)

186b: $^1$H-NMR (300 MHz, CD$_2$Cl$_2$): δ=0.05 ppm (s, 12H); 0.17 (m, 2H); 0.54 (s, 3H); 0.55 (m, 2H); 0.88 (s, 18H); 0.89 (t, 3H); 1.02 (d, 3H); 3.85 (m, 4H); 3.88 (m, 1H); 4.16 (m, 1H); 4.36 (m, 1H); 4.84 (s, 1H); 5.16 (s, 1H); 5.30 (dd, 1H); 5.42 (dd, 1H); 6.01 (d, 1H); 6.24 (d, 1H)

179. 46 mg of 186a is reacted analogously to 153., whereby 39 mg of (5Z,7E,22E)-(1S,3R,24R)-1,3-bis[[dimethyl(1,1-dimethylethyl)silyl]oxy]-25-(1-oxohexyl)-26,27-cyclo-24a,24b-dihomo-9,10-secocholesta-5,7,10(19),22-tetraene-24-ol 187a accumulates as a colorless foam, which is immediately further reacted.

180. 39 mg of 187a is reacted analogously to 154., whereby 11 mg of title compound 188a accumulates as a colorless foam.

$^1$H-NMR (300 MHz, CD$_2$Cl$_2$): δ=0.54 ppm (s, 3H); 0.71 (m, 2H); 0.86 (t, 3H); 1.00 (d, 3H); 1.12 (m, 2H); 2.18 (t, 2H); 3.93 (m, 1H); 4.16 (m, 1H); 4.36 (m, 1H); 4.94 (s, 1H); 5.28 (s, 1H); 5.34 (dd, 1H); 5.48 (dd, 1H); 5.99 (d, 1H); 6.33 (d, 1H)

181. 35 mg of 186b is reacted analogously to 153., whereby 27 mg of (5Z,7E,22E)-(1S,3R,24S)-1,3-bis[[dimethyl(1,1-dimethylethyl)silyl]oxy]-25-(1-oxohexyl)-26,27-cyclo-24a,24b-dihomo-9,10-secocholesta-5,7,10(19),22-tetraen-24-ol 187b is obtained as a colorless foam, which is immediately further reacted.

182. 27 mg of 187b is reacted analogously to 154., whereby 8.5 mg of title compound 188b accumulates as a colorless foam.

$^1$H-NMR (300 MHz, CD$_2$Cl$_2$): δ=0.55 ppm (s, 3H); 0.72 (m, 2H); 0.88 (t, 3H); 1.01 (d, 3H); 1.15 (m, 2H); 2.19 (t, 2H); 3.92 (m, 1H); 4.17 (m, 1H); 4.37 (m, 1H); 4.95 (s, 1H); 5.27 (s, 1H); 5.33 (dd, 1H); 5.46 (dd, 1H); 6.00 (d, 1H); 6.34 (d, 1H)

EXAMPLE 31

(5Z,7E,22E)-(1S,3R,24R)-25-(1-Oxoheptyl)-26,27-cyclo-24a,24b-dihomo-9,10-secocholesta-5,7,10(19),22-tetraene-1,3,24-triol 194a and (5Z,7E,22E)-(1S,3R,24S)-25-(1-oxoheptyl)-26,27-cyclo-24a,24b-dihomo-9,10-secocholesta-5,7,10(19),22-tetraene-1,3,24-triol 194b 183. 710 mg of ketone 162 is reacted with 573 mg of aldehyde 2 analogously to 149., and 580 mg of (5Z,7E)-(1S,3R)-1,3-bis[[dimethyl(1,1-dimethylethyl)silyl]oxy]-25-(2-hexyl-1,3-dioxolan-2-yl)-22-hydroxy-26,27-cyclo-24a,24b-dihomo-9,10-secocholesta-5,7,10(19)-trien-24-one 189 is obtained as a colorless foam, which is immediately further reacted.

184. A solution of 580 mg of 189 is reacted analogously to 150., whereby 603 mg of (5Z,7E)-(1S,3R)-22-acetoxy-1,3-bis[[dimethyl(1,1-dimethylethyl)silyl]oxy]-25-(2-hexyl-1,3-dioxolan-2-yl)-26,27-cyclo-24a,24b-dihomo-9,10-secocholesta-5,7,10(19)-trien-24-one 190 is obtained as a colorless foam, which is immediately further reacted.

185. 603 mg of 190 is reacted analogously to 151., whereby 304 mg of (5Z,7E,22E)-(1S,3R)-1,3-bis[[dimethyl(1,1-dimethylethyl)silyl]oxy]-25-(2-hexyl-1,3-dioxolan-2-yl)-26,27-cyclo-24a,24b-dihomo-9,10-secocholesta-5,7,10(19),22-tetraen-24-one 191 accumulates as a colorless foam.

$^1$H-NMR (300 MHz, CD$_2$Cl$_2$): δ=0.05 ppm (s, 12H); 0.19 (m, 2H); 0.57 (s, 3H); 0.59 (m, 2H); 0.89 (s, 18H); 0.90 (t, 3H); 1.09 (d, 3H); 3.85 (m, 4H); 4.17 (m, 1H); 4.37 (m, 1H); 4.85 (s, 1H); 5.16 (s, 1H); 5.96 (d, 1H); 6.01 (d, 1H); 6.24 (d, 1H); 6.66 (dd, 1H)

186. 295 mg of 191 is reacted analogously to 152., and after chromatography on silica gel with ethyl acetate/hexane, 130 mg of (5Z,7E,22E)-(1S,3R,24R)-1,3-bis[[dimethyl(1,1-dimethylethyl)silyl]oxy]-25-(2-hexyl-1,3-dioxolan-2-yl)-26,27-cyclo-24a,24b-dihomo-9,10-secocholesta-5,7,10(19),22-tetraen-24-ol 192a and 80 mg of (5Z,7E,22E)-(1S,3R,24S)-1,3-bis[[dimethyl(1,1-dimethylethyl)silyl]oxy]-25-(2-hexyl-1,3-dioxolan-2-yl)-26,27-cyclo-24a,24b-dihomo-9,10-secocholesta-5,7,10(19),22-tetraen-24-ol 192b are obtained as colorless foams.

$^1$H-NMR (300 MHz, CD$_2$Cl$_2$): 192a: δ=0.03 ppm (s, 12H); 0.18 (m, 2H); 0.56 (s, 3H); 0.56 (m, 2H); 0.89 (s, 18H); 0.90 (t, 3H); 1.04 (d, 3H); 3.86 (m, 4H); 3.93 (m, 1H); 4.18 (m, 1H); 4.38 (m, 1H); 4.86 (s, 1H); 5.19 (s, 1H); 5.35 (dd, 1H); 5.48 (dd, 1H); 6.01 (d, 1H); 6.26 (d, 1H)

192b: $^1$H-NMR (300 MHz, CD$_2$Cl$_2$): δ=0.03 ppm (s, 12H); 0.18 (m, 2H); 0.55 (s, 3H); 0.55 (m, 2H); 0.88 (s, 18H); 0.89 (t, 3H); 1.03 (d, 3H); 3.84 (m, 4H); 3.89 (m, 1H); 4.16 (m, 1H); 4.36 (m, 1H); 4.85 (s, 1H); 5.17 (s, 1H); 5.31 (dd, 1H); 5.43 (dd, 1H); 6.01 (d, 1H); 6.24 (d, 1H)

187. 80 mg of 192a is reacted analogously to 153., whereby 64 mg of (5Z,7E,22E)-(1S,3R,24R)-1,3-bis[[dimethyl(1,1-dimethylethyl)silyl]oxy]-25-(1-oxoheptyl)-26,27-cyclo-24a,24b-dihomo-9,10-secocholesta-5,7,10(19),22-tetraen-24-ol 193a accumulates as a colorless foam, which is immediately further reacted.

188. 64 mg of 193a is reacted analogously to 154., whereby 21 mg of title compound 194a accumulates as a colorless foam.

$^1$H-NMR (300 MHz, CD$_2$Cl$_2$): δ=0.56 ppm (s, 3H); 0.71 (m, 2H); 0.87 (t, 3H); 1.01 (d, 3H); 1.14 (m, 2H); 2.20 (t, 2H); 3.93 (m, 1H); 4.16 (m, 1H); 4.36 (m, 1H); 4.95 (s, 1H); 5.27 (s, 1H); 5.35 (dd, 1H); 5.48 (dd, 1H); 5.99 (d, 1H); 6.34 (d, 1H)

189. 76 mg of 192b is reacted analogously to 153., whereby 57 mg of (5Z,7E,22E)-(1S,3R,24S)-1,3-bis[[dimethyl(1,1-dimethylethyl)silyl]oxy]-25-(1-oxoheptyl)-26,27-cyclo-24a,24b-dihomo-9,10-secocholesta-5,7,10(19),22-tetraen-24-ol 193b is obtained as a colorless foam, which is immediately further reacted.

190. 57 mg of 193b is reacted analogously to 154., whereby 17 mg of title compound 194b accumulates as a colorless foam.

$^1$H-NMR (300 MHz, CD$_2$Cl$_2$): δ=0.56 ppm (s, 3H); 0.73 (m, 2H); 0.88 (t, 3H); 1.01 (d, 3H); 1.15 (m, 2H); 2.19 (t, 2H); 3.91 (m, 1H); 4.17 (m, 1H); 4.37 (m, 1H); 4.95 (s, 1H); 5.28 (s, 1H); 5.32 (dd, 1H); 5.47 (dd, 1H); 6.00 (d, 1H); 6.35 (d, 1H)

Synthesis of the Starting Materials in the 25-Alkyl Series 191. 2-(1-Ethylcyclopropyl)-2-methyl-1,3-dioxolan 195

500 mg of olefin 8 is dissolved in 15 ml of ethyl acetate, 150 mg of platinum(IV) oxide is added and hydrogenated in a hydrogenating apparatus until no more hydrogen is taken up. After filtration, it is concentrated by evaporation, whereby 398 mg of title compound 195 is obtained as a colorless oil, which is immediately further reacted.

192. 1-(1-Ethylcyclopropyl)-1-ethanone 196

370 mg of 195 is dissolved in 15 ml of acetone, and 1 ml of 4N hydrochloric acid is added at room temperature under nitrogen. It is stirred for 1 hour, and then diluted with sodium bicarbonate solution. After extraction with ether, drying on sodium sulfate, removal of the solvent and chromatography on silica gel with ethyl acetate/hexane, 178 mg of title compound 196 accumulates as a colorless oil.

$^1$H-NMR (300 MHz, CDCl$_3$): δ=0.77 ppm (m, 2H); 0.90 (t, 3H); 1.18 (m, 2H); 1.64 (q, 2H); 2.03 (s, 3H)

193. 2-[1-(1-Butenyl)cyclopropyl]-2-methyl-1,3-dioxolan 197

7.2 g of propyltriphenylphosphonium bromide is dissolved in 100 ml of diethyl ether, and 7.5 ml of n-butyl-lithium solution (2.5 M in hexane) is added in drops under nitrogen at room temperature. It is stirred for 1 hour, and then 2.34 g of aldehyde 7 is added to 10 ml of diethyl ether. It is stirred for 1 more hour, quenched with sodium chloride solution, extracted with ethyl acetate, washed with sodium chloride solution, dried on sodium sulfate and concentrated by evaporation. The residue is chromatographed on silica gel with ethyl acetate/hexane, whereby 1.8 g of title substance 197 is obtained as a colorless oil (1:3 E,Z-mixture that cannot be separated).

$^1$H-NMR (300 MHz, CDCl$_3$): E-Isomer: δ=0.50 ppm (m, 2H); 0.78 (m, 2H); 0.97 (t, 3H); 1.38 (s, 3H); 2.02 (q, 2H); 3.89 (m, 4H); 5.48 (dt, 1H); 5.80 (d, 1H)

Z-Isomer: δ=0.47 ppm (m, 2H); 0.81 (m, 2H); 0.97 (t, 3H); 1.38 (s, 3H); 2.22 (q, 2H); 390 (m, 4H); 5.46 (dt, 1H); 5.60 (d, 1H)

194. 1-[1-(1-Butenyl)cyclopropyl]-1-ethanone 198

1.1 g of 197 is reacted analogously to 192., and 740 mg of title compound 198 is obtained as a colorless oil (1:3 E,Z-mixture that cannot be separated).

$^1$H-NMR (300 MHz, CDCl$_3$): E-Isomer: δ=0.98 ppm (t, 3H); 1.01 (m, 2H); 1.33 (m, 2H); 2.11 (q, 2H); 2.20 (s, 3H); 5.54 (dt, 1H); 6.01 (d, 1H)

Z-Isomer: δ=0.88 ppm (m, 2H); 0.99 (t, 3H); 1.42 (m, 2H); 2.15 (q, 2H); 2.21 (s, 3H); 5.62 (dt, 1H); 5.71 (d, 1H)

195. 1-(1-Butylcyclopropyl)-1-ethanone 199

250 mg of 198 is reacted analogously to 191, and 195 mg of title compound 199 is obtained as a colorless oil.

$^1$H-NMR (300 MHz, CDCl$_3$): δ=0.75 ppm (m, 2H); 0.90 (t, 3H); 1.18 (m, 2H); 1.32 (m, 2H); 1.59 (m, 2H); 2.02 (s, 3H)

196. 2-[1-(1-Hexenyl)cyclopropyl]-2-methyl-1,3-dioxolan 200

2.07 g of pentyltriphenylphosphonium bromide and 600 mg of aldehyde 7 are reacted analogously to 193., and 567 g of title substance 200 is obtained as a colorless oil (8:1 E,Z-mixture that cannot be separated).

1H-NMR (300 MHz, CDCl$_3$): E-Isomer (Main diastereomer): δ=0.52 ppm (m, 2H); 0.78 (m, 2H); 0.90 (t, 3H); 1.40 (s, 3H); 2.00 (q, 2H); 3.90 (m, 4H); 5.42 (dt, 1H); 5.82 (d, 1H)

197. 1-(1-Hexylcyclopropyl)-2-methyl-1,3-dioxolan 201

250 mg of 200 is reacted analogously to 191., and 243 mg of title compound 201 is obtained as a colorless oil.

$^1$H-NMR (300 MHz, CDCl$_3$): δ=0.25 ppm (m, 2H); 0.58 (m, 2H); 0.87 (t, 3H); 1.28 (m, 8H); 1.39 (s, 3H); 1.48 (m, 2H); 3.88 (m, 4H)

198. 1-(1-Hexylcyclopropyl)-1-ethanone 202

330 mg of 201 is reacted analogously to 192., and 181 mg of title compound 202 is obtained as a colorless oil.

$^1$H-NMR (300 MHz, CDCl$_3$): δ=0.75 ppm (m, 2H); 0.89 (t, 3H); 1.18 (m, 2H); 1.28 (m, 8H); 1.58 (m, 2H); 2.02 (s, 3H)

199. 2-[1-(1-Heptenyl)cyclopropyl]-2-methyl-1,3-dioxolan 203

1.93 g of hexyltriphenylphosphonium bromide and 900 mg of aldehyde 7 are reacted analogously to 193., and 879 mg of title substance 203 is obtained as a colorless oil (1:3 E,Z mixture that cannot be separated).

$^1$H-NMR (300 MHz, CDCl$_3$): E-Isomer: δ=0.52 ppm (m, 2H); 0.78 (m, 2H); 0.90 (t, 3H); 1.40 (6H); 1.41 (s, 3H); 2.02 (q, 2H); 3.90 (m, 4H); 5.43 (dt, 1H); 5.80 (d, 1H)

Z-Isomer: δ=0.47 ppm (m, 2H); 0.82 (m, 2H); 0.90 (t, 3H); 1.40 (m, 6H); 2.20 (q, 2H); 3.91 (m, 4H); 5.47 (dt, 1H); 5.61 (d, 1H)

200. 1-(1-Heptylcyclopropyl)-2-methyl-1,3-dioxolan 204

550 mg of 203 is reacted analogously to 191., and 450 mg of title compound 204 is obtained as a colorless oil.

$^1$H-NMR (300 MHz, CDCl$_3$): δ=0.28 ppm (m, 2H); 0.59 (m, 2H); 0.89 (t, 3H); 1.28 (m, 10H); 1.40 (s, 3H); 1.48 (m, 2H); 3.90 (m, 4H)

201. 1-(1-Heptylcyclopropyl)-1-ethanone 205

445 mg of 204 is reacted analogously to 192., and 307 mg of title compound 205 is obtained as a colorless oil.

$^1$H-NMR (300 MHz, CDCl$_3$): δ=0.75 ppm (m, 2H); 0.89 (t, 3H); 1.18 (m, 2H); 1.28 (m, 10H); 1.58 (m, 2H); 2.02 (s, 3H)

202. (Z)-2-Methyl-2-[1-(1-octenyl)cyclopropyl]-1,3-dioxolan 206

4.87 g of heptyltriphenylphosphonium bromide and 1.25 g of aldehyde 7 are reacted analogously to 193., and 978 mg of title substance 206 is obtained as a colorless oil (only Z-isomer).

$^1$H-NMR (300 MHz, CDCl$_3$): δ=0.48 ppm (m, 2H); 0.81 (m, 2H); 0.89 (t, 3H); 1.29 (8H); 1.40 (s, 3H); 2.02 (m, 2H); 3.92 (m, 4H); 5.48 (dt, 1H); 5.62 (d, 1H)

203. 2-Methyl-1-(1-octylcyclopropyl)-1,3-dioxolan 207

400 mg of 206 is reacted analogously to 191., and 390 mg of pound 207 is obtained as a colorless oil.

$^1$H-NMR (300 MHz, CDCl$_3$): δ=0.28 ppm (m, 2H); 0.59 (m, 2H); 0.90 (t, 3H); 1.28 (m, 12H); 1.39 (s, 3H); 1.48 (m, 2H); 3.90 (m, 4H)

204. 1-(1-Octylcyclopropyl)-1-ethanone 208

390 mg of 207 is reacted analogously to 192., and 250 mg of title compound 208 is obtained as a colorless oil.

$^1$H-NMR (300 MHz, CDCl$_3$): δ=0.77 ppm (m, 2H); 0.90 (t, 3H); 1.18 (m, 2H); 1.28 (m, 12H); 1.58 (m, 2H); 2.02 (s, 3H)

205. 1-[1-(1-Octenyl) cyclopropyl]-1-ethanone 209

330 mg of 206 is reacted analogously to 192., and 270 mg of title compound 209 is obtained as a colorless oil.

$^1$H-NMR (300 MHz, CDCl$_3$) δ=0.90 ppm (m, 2H); 0.90 (t, 3H); 1.18 (m, 2H); 1.30 (m, 8H); 1.44 (m, 2H); 2.10 (q, 2H); 2.22 (s, 3H); 5.64 (dt, 1H); 5.74 (d, 1H)

EXAMPLE 32

(5Z,7E,22E)-(1S,3R,24S)-25-Ethyl-26,27-cyclo-9, 10-secocholesta-5,7,10(19),22-tetraene-1,3,24-triol 214a and (5Z,7E,22E)-(1S,3R,24R)-25-ethyl-26,27-cyclo-9,10-secocholesta-5,7,10(19),22-tetraene-1,3, 24-triol 214b 206. 129 mg of 196 is reacted with 286 mg of aldehyde 2 analogously to 149., and 187 mg of (5Z,7E)-(1S,3R)-1,3-bis[[dimethyl(1,1-dimethylethyl)silyl]oxy]-25-ethyl-22-hydroxy-26,27-cyclo-9,10-secocholesta-5,7,10(19)-trien-24-one 210 is obtained as a colorless foam, which is immediately further reacted.

207. 170 mg of 210 is reacted analogously to 150., and 151 mg of (5Z,7E)-(1S,3R)-22-acetoxy-1,3-bis[[dimethyl(1, 1-dimethylethyl)silyl]oxy]-25-ethyl-26,27-cyclo-9,10-secocholesta-5,7,10(19)-trien-24-one 211 is obtained as a colorless foam, which is immediately further reacted.

208. 151 mg of 211 is reacted analogously to 151., and 110 mg of (5Z,7E,22E)-(1S,3R)-1,3-bis[[dimethyl(1,1-dimethylethyl)silyl]oxy]-25-ethyl-26,27-cyclo-9,10-secocholesta-5,7,10(19),22-tetraen-24-one 212 is obtained as a colorless foam.

$^1$H-NMR (300 MHz, CD$_2$Cl$_2$): δ=0.04 ppm (s, 12H); 0.54 (s, 3H); 0.73 (m, 2H); 0.87 (s, 18H); 0.92 (m, 2H); 0.93 (t, 3H); 1.05 (d, 3H); 4.17 (m, 1H); 4.37 (m, 1H); 4.83 (s, 1H); 5.17 (s, 1H); 6.01 (d, 1H); 6.11 (d, 1H); 6.23 (d, 1H); 6.70 (dd, 1H)

209. 110 mg of 212 is reacted analogously to 152., and after chromatography on silica gel with ethyl acetate/hexane, 42 mg of (5Z,7E,22E)-(1S,3R,24S)-1,3-bis[[dimethyl (1,1-dimethylethyl)silyl]oxy]-25-ethyl-26,27-cyclo-9,10-secocholesta-5,7,10(19),22-tetraen-24-ol 213a and 25 mg of (5Z,7E,22E)-(1S,3R,24R)-1,3-bis[[dimethyl(1,1-dimethylethyl)silyl]oxy]-25-ethyl-26,27-cyclo-9,10-secocholesta-5, 7,10(19),22-tetraen-24-ol 213b are obtained in succession as colorless foams.

$^1$H-NMR (300 MHz, CD$_2$Cl$_2$): 213a: δ=0.03 ppm (s, 12H); 0.25 (m, 2H); 0.42 (m, 2H); 0.53 (s, 3H); 0.85 (t, 3H); 0.86 (s, 18H); 1.02 (d, 3H); 3.80 (m, 1H); 4.16 (m, 1H); 4.36 (m, 1H); 4.83 (s, 1H); 5.16 (s, 1H); 5.33 (dd, 1H); 5.50 (dd, 1H); 6.01 (d, 1H); 6.23 (d, 1H)

213b: δ=0.03 ppm (s, 12H); 0.25 (m, 2H); 0.43 (m, 2H); 0.53 (s, 3H); 0.85 (t, 3H); 0.85 (s, 18H); 1.03 (d, 3H); 3.78 (m, 1H); 4.17 (m, 1H); 4.36 (m, 1H); 4.83 (s, 1H); 5.16 (s, 1H); 5.33 (dd, 1H); 5.45 (dd, 1H); 6.01 (d, 1H); 6.23 (d, 1H)

210. 42 mg of 213a is reacted analogously to 154., and 18 mg of title compound 214a is obtained as a colorless foam.

$^1$H-NMR (300 MHz, CD$_2$Cl$_2$): δ=0.29 ppm (m, 2H); 0.42 (m, 2H); 0.57 (s, 3H); 0.88 (t, 3H); 1.03 (d, 3H); 3.81 (d, 1H); 4.17 (m, 1H); 4.38 (m, 1H); 4.95 (s, 1H); 5.29 (s, 1H); 5.35 (dd, 1H); 5.51 (dd, 1H); 6.00 (d, 1H); 6.35 (d, 1H)

211. 25 mg of 213b is reacted analogously to 154., and 9.5 mg of title compound 214b is obtained as a colorless foam.

$^1$H-NMR (300 MHz, CD$_2$Cl$_2$): δ=0.27 ppm (m, 2H); 0.44 (m, 2H); 0.57 (s, 3H); 0.89 (t, 3H); 1.02 (d, 3H); 3.79 (d, 1H); 4.17 (m, 1H); 4.38 (m, 1H); 4.96 (s, 1H); 5.29 (s, 1H); 5.34 (dd, 1H); 5.48 (dd, 1H); 6.00 (d, 1H); 6.36 (d, 1H)

EXAMPLE 33

[5Z,7E,22E,25(Z)]-(1S,3R,24S)-25-(1-Butenyl)-26, 27-cyclo-9,10-secocholesta-5,7,10(19),22-tetraene-1, 3,24-triol 220b, [5Z,7E,22E,25(E)]-(1S,3R,24S)-25-(1-butenyl)-26,27-cyclo-9,10-secocholesta-5,7,10 (19),22-tetraene-1,3,24-triol 221a and [5Z,7E,22E, 25(E)]-(1S,3R,24R)-25-(1-butenyl)-26,27-cyclo-9, 10-secocholesta-5,7,10(19),22-tetraene-1,3,24-triol 221b 212. 460 mg of 198 is reacted with 573 mg of aldehyde 2 analogously to 149., and 546 mg of (5Z,7E)-(1S,3R)-1,3-bis[[dimethyl(1,1-dimethylethyl)silyl]oxy]-25-(1-butenyl)-22-hydroxy-26,27-cyclo-9,10-secocholesta-5,7,10(19)-trien-24-one 215 is obtained as a colorless foam, which is immediately further reacted.

213. 275 mg of 215 is reacted analogously to 150., and 265 mg of (5Z,7E)-(1S,3R)-22-acetoxy-1,3-bis[[dimethyl(1, 1-dimethylethyl)silyl]oxy]-25-(1-butenyl)-26,27-cyclo-9, 10-secocholesta-5,7,10(19)-trien-24-one 216 is obtained as a colorless foam, which is immediately further reacted.

214. 265 mg of 216 is reacted analogously to 151., and 214 mg of (5Z,7E,22E)-(1S,3R)-1,3-bis[[dimethyl(1,1-dimethylethyl)silyl]oxy]-25-(1-butenyl)-26,27-cyclo-9,10-secocholesta-5,7,10(19),22-tetraen-24-one 217 is obtained as a colorless foam (1:3 E:Z-mixture).

215. 214 mg of 217 is reacted analogously to 152., and after chromatography on silica gel with ethyl acetate/hexane, 31 mg of [5Z,7E,22E,25(Z)]-(1S,3R,24R)-1,3-bis [[dimethyl(1,1-dimethylethyl)silyl]oxy]-25-(1-butenyl)-26, 27-cyclo-9,10-secocholesta-5,7,10(19),22-tetraen-24-ol 218b, 27 mg of [5Z,7E,22E,25(E)]-(1S,3R,24S)-1,3-bis [[dimethyl(1,1-dimethylethyl)silyl]oxy]-25-(1-butenyl)-26, 27-cyclo-9,10-secocholesta-5,7,10(19),22-tetraen-24-ol 219a and 22 mg of [5Z,7E,22E,25(E)]-(1S,3R,24R)-1,3-bis [[dimethyl(1,1-dimethylethyl)silyl]oxy]-25-(1-butenyl)-26, 27-cyclo-9,10-secocholesta-5,7,10(19),22-tetraen-24-ol 219b are obtained in succession as colorless foams.

$^1$H-NMR (300 MHz, CD$_2$Cl$_2$): 218b: δ=0.03 ppm (s, 12H); 0.53 (s, 3H); 0.86 (s, 18H); 0.93 (t, 3H); 1.01 (d, 3H); 3.49 (d, 1H); 4.17 (m, 1H); 4.37 (m, 1H); 4.84 (s, 1H); 5.17 (s, 1H); 5.42 (m, 2H); 5.49 (m, 2H); 6.01 (d, 1H); 6.23 (d, 1H)

219a: δ=0.03 ppm (s, 12H); 0.53 (s, 3H); 0.87 (s, 18H); 0.94 (t, 3H); 1.03 (d, 3H); 3.60 (d, 1H); 4.17 (m, 1H); 4.37 (m, 1H); 4.83 (s, 1H); 5.17 (s, 1H); 5.40 (dt, 1H); 5.46 (m, 2H); 5.59 (d, 1H); 6.01 (d, 1H); 6.23 (d, 1H)

219b: δ=0.04 ppm (s, 12H); 0.53 (s, 3H); 0.87 (s, 18H); 0.95 (t, 3H); 1.01 (d, 3H); 3.48 (d, 1H); 4.17 (m, 1H); 4.37 (m, 1H); 4.84 (s, 1H); 5.18 (s, 1H); 5.41 (m, 2H); 5.50 (m, 2H); 6.01 (d, 1H); 6.24 (d, 1H)

216. 17 mg of 218b is reacted analogously to 154., and 7 mg of title compound 220b is obtained as a colorless foam.

$^1$H-NMR (300 MHz, CD$_2$Cl$_2$): δ=0.42 ppm (m, 2H); 0.53 (s, 3H); 0.56 (m, 2H); 0.94 (t, 3H); 1.02 (d, 3H); 3.49 (m, 1H); 4.16 (m, 1H); 4.36 (m, 1H); 4.93 (s, 1H); 5.29 (s, 1H); 5.41 (m, 2H); 5.45 (m, 1H); 6.00 (d, 1H); 6.33 (d, 1H)

217. 27 mg of 219a is reacted analogously to 154., and 11 mg of title compound 221a is obtained as a colorless foam.

$^1$H-NMR (300 MHz, CD$_2$Cl$_2$): δ=0.44 ppm (m, 2H); 0.54 (s, 3H); 0.57 (m, 2H); 0.97 (t, 3H); 1.03 (d, 3H); 3.59 (d, 1H); 4.17 (m, 1H); 4.38 (m, 1H); 4.95 (s, 1H); 5.29 (s, 1H); 5.45 (m, 3H); 5.58 (d, 1H); 6.00 (d, 1H); 6.36 (d, 1H)

218. 22 mg of 219b is reacted analogously to 154., and 8 mg of title compound 221b is obtained as a colorless foam.

$^1$H-NMR (300 MHz, CD$_2$Cl$_2$): δ=0.45 ppm (m, 2H); 0.55 (s, 3H); 0.58 (m, 2H); 0.97 (t, 3H); 1.02 (d, 3H); 3.49 (d, 1H); 4.18 (m, 1H); 4.38 (m, 1H); 4.96 (s, 1H); 5.29 (s, 1H); 5.42 (m, 2H); 5.50 (m, 2H); 6.01 (d, 1H); 6.36 (d, 1H)

EXAMPLE 34

(5Z,7E,22E)-(1S,3R,24S)-25-Butyl-26,27-cyclo-9,10-secocholesta-5,7,10(19),22-tetraene-1,3,24-triol 226a and (5Z,7E,22E)-(1S,3R,24R)-25-butyl-26,27-cyclo-9,10-secocholesta-5,7,10(19),22-tetraene-1,3,24-triol 226b 219. 195 mg of 199 is reacted with 400 mg of aldehyde 2 analogously to 149., and 275 mg of (5Z,7E)-(1S,3R)-1,3-bis[[(dimethyl(1,1-dimethylethyl)silyl]oxy]-25-butyl-22-hydroxy-26,27-cyclo-9,10-secocholesta-5,7,10(19)-trien-24-one 222 is obtained as a colorless foam, which is immediately further reacted.

220. 275 mg of 222 is reacted analogously to 150., and 245 mg of (5Z,7E)-(1S,3R)-22-acetoxy-1,3-bis[[dimethyl(1,1-dimethylethyl)silyl]oxy]-25-butyl-26,27-cyclo-9,10-secocholesta-5,7,10(19)-trien-24-one 223 is obtained as a colorless foam, which is immediately further reacted.

221. 245 mg of 233 is reacted analogously to 151., and 214 mg of (5Z,7E,22E)-(1S,3R)-1,3-bis[[dimethyl(1,1-dimethylethyl)silyl]oxy]-25-butyl-26,27-cyclo-9,10-secocholesta-5,7,10(19),22-tetraen-24-one 224 is obtained as a colorless foam.

$^1$H-NMR (300 MHz, CD$_2$Cl$_2$): δ=0.04 ppm (s, 12H); 0.54 (s, 3H); 0.74 (m, 2H); 0.87 (s, 18H); 0.88 (t, 3H); 0.92 (m, 2H); 1.06 (d, 3H); 4.17 (m, 1H); 4.36 (m, 1H); 4.83 (s, 1H); 5.15 (s, 1H); 6.01 (d, 1H); 6.14 (d, 1H); 6.23 (d, 1H); 6.66 (dd, 1H)

222. 214 mg of 224 is reacted analogously to 152., and after chromatography on silica gel with ethyl acetate/hexane, 80 mg of (5Z,7E,22E)-(1S,3R,24S)-1,3-bis[[dimethyl(1,1-dimethylethyl)silyl]oxy]-25-butyl-26,27-cyclo-9,10-secocholesta-5,7,10(19),22-tetraen-24-ol 225a and 41 mg of (5Z,7E,22E)-(1S,3R,24R)-1,3-bis[[dimethyl(1,1-dimethylethyl)silyl]oxy]-25-butyl-26,27-cyclo-9,10-secocholesta-5,7,10(19),22-tetraen-24-ol 225b are obtained in succession as colorless foams.

$^1$H-NMR (300 MHz, CD$_2$Cl$_2$): 225a: δ=0.03 ppm (s, 12H); 0.25 (m, 2H); 0.43 (m, 2H); 0.53 (s, 3H); 0.86 (t, 3H); 0.86 (s, 18H); 1.03 (d, 3H); 3.79 (m, 1H); 4.17 (m, 1H); 4.36 (m, 1H); 4.83 (s, 1H); 5.16 (s, 1H); 5.35 (dd, 1H); 5.50 (dd, 1H); 6.01 (d, 1H); 6.23 (d, 1H)

225b: δ 0.03 ppm (s, 12H); 0.24 (m, 2H); 0.43 (m, 2H); 0.53 (s, 3H); 0.86 (t, 3H); 0.87 (s, 18H); 1.03 (d, 3H); 3.77 (m, 1H); 4.17 (m, 1H); 4.36 (m, 1H); 4.83 (s, 1H); 5.16 (s, 1H); 5.33 (dd, 1H); 5.45 (dd, 1H); 6.01 (d, 1H); 6.23 (d, 1H)

223. 80 mg of 225a is reacted analogously to 154., and 37 mg of title compound 226a is obtained as a colorless foam.

$^1$H-NMR (300 MHz, CD$_2$Cl$_2$): δ=0.28 ppm (m, 2H); 0.44 (m, 2H); 0.58 (s, 3H); 0.89 (t, 3H); 1.03 (d, 3H); 3.79 (d, 1H); 4.18 (m, 1H); 4.38 (m, 1H); 4.96 (s, 1H); 5.29 (s, 1H); 5.37 (dd, 1H); 5.51 (dd, 1H); 6.00 (d, 1H); 6.36 (d, 1H)

224. 41 mg of 225b is reacted analogously to 154., and 17 mg of title compound 226b is obtained as a colorless foam.

$^1$H-NMR (300 MHz, CD$_2$Cl$_2$): δ=0.26 ppm (m, 2H); 0.44 (m, 2H); 0.58 (s, 3H); 0.88 (t, 3H); 1.02 (d, 3H); 3.78 (d, 1H); 4.18 (m, 1H); 4.38 (m, 1H); 4.97 (s, 1H); 5.29 (s, 1H); 5.34 (dd, 1H); 5.48 (dd, 1H); 6.00 (d, 1H); 6.36 (d, 1H)

EXAMPLE 35

(5Z,7E,22E)-(1S,3R,24S)-25-Hexyl-26,27-cyclo-9,10-secocholesta-5,7,10(19),22-tetraene-1,3,24-triol 231a and (5Z,7E,22E)-(1S,3R,24R)-25-hexyl-26,27-cyclo-9,10-secocholesta-5,7,10(19),22-tetraene-1,3,24-triol 231b 225. 120 mg of 202 is reacted with 287 mg of aldehyde 2 analogously to 149., and 256 mg of (5Z,7E)-(1S,3R)-1,3-bis[[dimethyl(1,1-dimethylethyl)silyl]oxy]-25-hexyl-22-hydroxy-26,27-cyclo-9,10-sechocholesta-5,7,10(19)-trien-24-one 227 is obtained as a colorless foam, which is immediately further reacted.

226. 256 mg of 227 is reacted analogously to 150., and 234 mg of (5Z,7E)-(1S,3R)-22-acetoxy-1,3-bis[[dimethyl(1,1-dimethylethyl)silyl]oxy]-25-hexyl-26,27-cyclo-9,10-secocholesta-5,7,10(19)-trien-24-one 228 is obtained as a colorless foam, which is immediately further reacted.

227. 234 mg of 228 is reacted analogously to 151., and 104 mg of (5Z,7E,22E)-(1S,3R)-1,3-bis[[dimethyl(1,1-dimethylethyl)-silyl]oxy]-25-hexyl-26,27-cyclo-9,10-secocholesta-5,7,10(19),22-tetraen-24-one 229 is obtained as a colorless foam.

$^1$H-NMR (300 MHz, CD$_2$Cl$_2$): δ=0.05 ppm (s, 12H); 0.56 (s, 3H); 0.74 (m, 2H); 0.88 (s, 18H); 0.89 (t, 3H); 0.93 (m, 2H); 1.08 (d, 3H); 4.18 (m, 1H); 4.38 (m, 1H); 4.85 (s, 1H); 5.17 (s, 1H); 6.01 (d, 1H); 6.15 (d, 1H); 6.23 (d, 1H); 6.73 (dd, 1H)

228. 104 mg of 229 is reacted analogously to 1523., and after chromatography on silica gel with ethyl acetate/hexane, 37 mg of (5Z,7E,22E)-(1S,3R,24S)-1,3-bis[[dimethyl(1,1-dimethylethyl)silyl]oxy]-25-hexyl-26,27-cyclo-9,10-secocholesta-5,7,10(19),22-tetraen-24-ol 230a and 35 mg of (5Z,7E,22E)-(1S,3R,24R)-1,3-bis[[dimethyl(1,1-dimethylethyl)silyl]oxy]-25-hexyl-26,27-cyclo-9,10-secocholesta-5,7,10(19),22-tetraen-24-ol 230b are obtained in succession as colorless foams.

$^1$H-NMR (300 MHz, CD$_2$Cl$_2$): 230a: δ=0.04 ppm (s, 12H); 0.24 (m, 2H); 0.43 (m, 2H); 0.54 (s, 3H); 0.87 (t, 3H); 0.87 (s, 18H); 1.02 (d, 3H); 3.77 (m, 1H); 4.17 (m, 1H); 4.36 (m, 1H); 4.84 (s, 1H); 5.16 (s, 1H); 5.34 (dd, 1H); 5.50 (dd, 1H); 6.01 (d, 1H); 6.24 (d, 1H)

230b: δ=0.04 ppm (s, 12H); 0.23 (m, 2H); 0.43 (m, 2H); 0.54 (s, 3H); 0.87 (t, 3H); 0.87 (s, 18H); 1.03 (d, 3H); 3.75 (d, 1H); 4.17 (m, 1H); 4.37 (m, 1H); 4.84 (s, 1H); 5.16 (s, 1H); 5.33 (dd, 1H); 5.46 (dd, 1H); 6.01 (d, 1H); 6.24 (d, 1H)

229. 37 mg of 230a is reacted analogously to 154., and 17 mg of title compound 231a is obtained as a colorless foam.

$^1$H-NMR (300 MHz, CD$_2$Cl$_2$): =0.28 ppm (m, 2H); 0.43 (m, 2H); 0.58 (s, 3H); 0.90 (t, 3H); 1.04 (d, 3H); 3.80 (d, 1H); 4.18 (m, 1H); 4.38 (m, 1H); 4.96 (s, 1H); 5.28 (s, 1H); 5.35 (dd, 1H); 5.51 (dd, 1H); 6.01 (d, 1H); 6.36 (d, 1H)

230. 31 mg of 230b is reacted analogously to 154., and 10 mg of title compound 231b is obtained as a colorless foam.

$^1$H-NMR (300 MHz, CD$_2$Cl$_2$): δ=0.28 ppm (m, 2H); 0.46 (m, 2H); 0.59 (s, 3H); 0.89 (t, 3H); 1.04 (d, 3H); 3.79 (d, 1H); 4.18 (m, 1H); 4.38 (m, 1H); 4.97 (s, 1H); 5.29 (s, 1H); 5.35 (dd, 1H); 5.48 (dd, 1H); 6.00 (d, 1H); 6.37 (d, 1H)

EXAMPLE 36

(5Z,7E,22E)-(1S,3R,24S)-25-Heptyl-26,27-cyclo-9,10-secocholesta-5,7,10(19),22-tetraene-1,3,24-triol 236a and (5Z,7E,22E)-(1S,3R,24R)-25-heptyl-26,27-cyclo-9,10-secocholesta-5,7,10(19),22-tetraene-1,3,24-triol 236b 231. 300 mg of 205 is reacted with 573 mg of aldehyde 2 analogously to 149., and 556 mg of (5Z,7E)-(1S,3R)-1,3-bis[[dimethyl(1,1-dimethylethyl)silyl]oxy]-25-heptyl-22-hydroxy-26,27-cyclo-9,10-secocholesta-5,7,10(19)-trien-24-one 232 is obtained as a colorless foam, which is immediately further reacted.

232. 305 mg of 232 is reacted analogously to 150., and 278 mg of (5Z,7E)-(1S,3R)-22-acetoxy-1,3-bis[[dimethyl(1,1-dimethylethyl)silyl]oxy]-25-heptyl-26,27-cyclo-9,10-secocholesta-5,7,10(19)-trien-24-one 233 is obtained as a colorless foam, which is immediately further reacted.

233. 278 mg of 233 is reacted analogously to 151., and 203 mg of (5Z,7E,22E)-(1S,3R)-1,3-bis[[dimethyl(1,1-dimethylethyl)silyl]oxy]-25-heptyl-26,27-cyclo-9,10-secocholesta-5,7,10(19),22-tetraen-24-one 234 is obtained as a colorless foam.

$^1$H-NMR (300 MHz, CD$_2$Cl$_2$): δ=0.05 ppm (s, 12H); 0.57 (s, 3H); 0.74 (m, 2H); 0.89 (s, 18H); 0.89 (t, 3H); 0.94 (m, 2H); 1.09 (d, 3H); 4.18 (m, 1H); 4.38 (m, 1H); 4.87 (s, 1H); 5.18 (s, 1H); 6.01 (d, 1H); 6.14 (d, 1H); 6.22 (d, 1H); 6.75 (dd, 1H)

234. 200 mg of 234 is reacted analogously to 152., and after chromatography on silica gel with ethyl acetate/hexane, 80 mg of (5Z,7E,22E)-(1S,3R,24S)-1,3-bis[[dimethyl(1,1-dimethylethyl)silyl]oxy]-25-heptyl-26,27-cyclo-9,10-secocholesta-5,7,10(19),22-tetraen-24-ol 235a and 38 mg of (5Z,7E,22E)-(1S,3R,24R)-1,3-bis[[dimethyl(1,1-dimethylethyl)silyl]oxy]-25-heptyl-26,27-cyclo-9,10-secocholesta-5,7,10(19),22-tetraen-24-ol 235b are obtained in succession as colorless foams.

$^1$H-NMR (300 MHz, CD$_2$Cl$_2$): 235a: δ=0.04 ppm (s, 12H); 0.24 (m, 2H); 0.43 (m, 2H); 0.53 (s, 3H); 0.86 (t, 3H); 0.86 (s, 18H); 1.02 (d, 3H); 3.75 (m, 1H); 4.17 (m, 1H); 4.36 (m, 1H); 4.84 (s, 1H); 5.16 (s, 1H); 5.33 (dd, 1H); 5.50 (dd, 1H); 6.00 (d, 1H); 6.23 (d, 1H)

235b: δ=0.04 ppm (s, 12H); 0.24 (m, 2H); 0.43 (m, 2H); 0.53 (s, 3H); 0.87 (t, 3H); 0.87 (s, 18H); 1.03 (d, 3H); 3.76 (d, 1H); 4.17 (m, 1H); 4.36 (m, 1H); 4.83 (s, 1H); 5.15 (s, 1H); 5.33 (dd, 1H); 5.45 (dd, 1H); 6.00 (d, 1H); 6.23 (d, 1H)

235. 75 mg of 235a is reacted analogously to 154., and 51 mg of title compound 236a is obtained as a colorless foam.

$^1$H-NMR (300 MHz, CD$_2$Cl$_2$): δ=0.26 ppm (m, 2H); 0.43 (m, 2H); 0.56 (s, 3H); 0.88 (t, 3H); 1.02 (d, 3H); 3.78 (d, 1H); 4.17 (m, 1H); 4.37 (m, 1H); 4.95 (s, 1H); 5.28 (s, 1H); 5.34 (dd, 1H); 5.50 (dd, 1H); 6.00 (d, 1H); 6.35 (d, 1H)

236. 33 mg of 235b is reacted analogously to 154., and 17 mg of title compound 236b is obtained as a colorless foam.

$^1$H-NMR (300 MHz, CD$_2$Cl$_2$): δ=0.26 ppm (m, 2H); 0.44 (m, 2H): 0.56 (s, 3H); 0.87 (t, 3H); 1.03 (d, 3H); 3.76 (d, 1H); 4.16 (m, 1H); 4.36 (m, 1H); 4.95 (s, 1H); 5.28 (s, 1H); 5.33 (dd, 1H); 5.45 (dd, 1H); 6.00 (d, 1H); 6.35 (d, 1H)

EXAMPLE 37

(5Z,7E,22E)-(1S,3R,24S)-25-Octyl-26,27-cyclo-9,10-secocholesta-5,7,10(19),22-tetraene-1,3,24-triol 241a and (5Z,7E,22E)-(1S,3R,24R)-25-octyl-26,27-cyclo-9,10-secocholesta-5,7,10(19),22-tetraene-1,3,24-triol 241b 237. 250 mg of 208 is reacted with 500 mg of aldehyde 2 analogously to 149., and 432 mg of (5Z,7E)-(1S,3R)-1,3-bis[[dimethyl(1,1-dimethylethyl)silyl]oxy]-22-hydroxy-25-octyl 26,27-cyclo-9,10-secocholesta-5,7,10(19)-trien-24-one 237 is obtained as a colorless foam, which is immediately further reacted.

238. 380 mg of 237 is reacted analogously to 150., and 356 mg of (5Z,7E)-(1S,3R)-22-acetoxy-1,3-bis[[dimethyl(1,1-dimethylethyl)silyl]-oxy]-25-octyl-26,27-cyclo-9,10-secocholesta-5,7,10(19)-trien-24-one 238 is obtained as a colorless foam, which is immediately further reacted.

239. 356 mg of 238 is reacted analogously to 151., and 310 mg of (5Z,7E,22E)-(1S,3R)-1,3-bis[[dimethyl(1,1-dimethylethyl)silyl]oxy]-25-octyl-26,27-cyclo-9,10-secocholesta-5,7,10(19),22-tetraen-24-one 239 is obtained as a colorless foam.

$^1$H-NMR (300 MHz, CD$_2$Cl$_2$): δ=0.04 ppm (s, 12H); 0.57 (s, 3H); 0.74 (m, 2H); 0.88 (s, 18H); 0.89 (t, 3H); 0.93 (m, 2H); 1.09 (d, 3H); 4.18 (m, 1H); 4.38 (m, 1H); 4.87 (s, 1H); 5.18 (s, 1H); 6.01 (d, 1H); 6.14 (d, 1H); 6.23 (d, 1H); 6.76 (dd, 1H) 240. 310 mg of 239 is reacted analogously to 152., and after chromatography on silica gel with ethyl acetate/hexane, 130 mg of (5Z,7E,22E)-(1S,3R,24S)-1,3-bis[[dimethyl(1,1-dimethylethyl)silyl]oxy]-25-octyl-26,27-cyclo-9,10-secocholesta-5,7,10(19),22-tetraen-24-ol 240a and 53 mg of (5Z,7E,22E)-(1S,3R,24R)-1,3-bis[[dimethyl(1,1-dimethylethyl)silyl]oxy]-25-octyl-26,27-cyclo-9,10-secocholesta-5,7,10(19),22-tetraen-24-ol 240b are obtained in succession as colorless foams.

$^1$H-NMR (300 MHz, CD$_2$Cl$_2$): 240a: δ=0.04 ppm (s, 12H); 0.24 (m, 2H); 0.43 (m, 2H); 0.55 (s, 3H); 0.88 (t, 3H); 0.88 (s, 18H); 1.04 (d, 3H); 3.79 (m, 1H); 4.18 (m, 1H): 4.38 (m, 1H); 4.86 (s, 1H); 5.18 (s, 1H); 5.36 (dd, 1H); 5.51 (dd, 1H); 6.01 (d, 1H); 6.25 (d, 1H)

240b: δ=0.04 ppm (s, 12H); 0.24 (m, 2H); 0.43 (m, 2H); 0.56 (s, 3H); 0.88 (t, 3H); 0.89 (s, 18H); 1.05 (d, 3H); 3.78 (d, 1H); 4.18 (m, 1H); 4.38 (m, 1H); 4.84 (s, 1H); 5.18 (s, 1H); 5.35 (dd, 1H); 5.48 (dd, 1H); 6.01 (d, 1H); 6.25 (d, 1H)

241. 130 mg of 240a is reacted analogously to 154., and 67 mg of title compound 241a is obtained as a colorless foam.

$^1$H-NMR (300 MHz, CD$_2$Cl$_2$): δ=0.28 ppm (m, 2H); 0.45 (m, 2H); 0.57 (s, 3H); 0.89 (t, 3H); 1.04 (d, 3H); 3.79 (d, 1H); 4.18 (m, 1H); 4.38 (m, 1H); 4.97 (s, 1H); 5.29 (s, 1H); 5.36 (dd, 1H); 5.51 (dd, 1H); 6.01 (d, 1H); 6.36 (d, 1H)

242. 53 mg of 240b is reacted analogously to 154., and 16 mg of title compound 241b is obtained as a colorless foam.

$^1$H-NMR (300 MHz, CD$_2$Cl$_2$): δ=0.28 ppm (m, 2H); 0.47 (m, 2H); 0.57 (s, 3H); 0.89 (t, 3H); 1.05 (d, 3H); 3.79 (d, 1H); 4.17 (m, 1H); 4.38 (m, 1H); 4.96 (s, 1H); 5.29 (s, 1H); 5.35 (dd, 1H); 6.01 (d, 1H); 6.37 (d, 1H)

EXAMPLE 38

[5Z,7E,22E,25(Z)]-(1S,3R,24S)-25-(1-Octenyl)-26,
27-cyclo-9,10-secocholesta-5,7,10(19),22-tetraene-1,
3,24-triol 246a and [5Z,7E,22E,25(Z)]-(1S,3R,24S)-
25-(1-octenyl)-26,27-cyclo-9,10-secocholesta-5,7,10
(19),22-tetraene-1,3,24-triol 246b 243. 250 mg of 209 is reacted with 573 mg of aldehyde 2 analogously to 149., and 550 mg of [5Z,7E,25(Z)]-(1S,3R)-1,3-bis[[dimethyl(1,1-dimethylethyl)silyl]oxy]-22-hydroxy-25-(1-octenyl)-26,27-cyclo-9,10-secocholesta-5,7,10(19)-trien-24-one 242 is obtained as a colorless foam, which is immediately further reacted.

244. 540 mg of 242 is reacted analogously to 150., and 476 mg of [5Z,7E,25(Z)]-(1S,3R)-22-acetoxy-1,3-bis[[dimethyl(1,1-dimethylethyl)silyl]oxy]-25-(1-octenyl)-26,27-cyclo-9,10-secocholesta-5,7,10(19)-trien-24-one 243 is obtained as a colorless foam, which is immediately further reacted.

245. 476 mg of 243 is reacted analogously to 151., and 323 mg of [5Z,7E,22E,25(Z)]-(1S,3R)-1,3-bis[[dimethyl(1,1-dimethylethyl)silyl]oxy]-25-(1-octenyl)-26,27-cyclo-9,10-secocholesta-5,7,10(19),22-tetraen-24-one 244 is obtained as a colorless foam.

$^1$H-NMR (300 MHz, $CD_2Cl_2$): δ=0.06 ppm (s, 12H); 0.57 (s, 3H); 0.74 (m, 2H); 0.89 (s, 18H); 0.89 (t, 3H); 0.93 (m, 2H); 1.09 (d, 3H); 4.18 (m, 1H); 4.38 (m, 1H); 4.88 (s, 1H); 5.19 (s, 1H); 6.01 (d, 1H); 6.23 (d, 1H); 6.54 (d, 1H); 6.72 (dd, 1H)

246. 320 mg of 244 is reacted analogously to 152., and after chromatography on silica gel with ethyl acetate/hexane, 128 mg of 245a and 68 mg of [5Z,7E,22E,25(E)]-(1S,3R,24S)-1,3-bis[[dimethyl(1,1-dimethylethyl)silyl]oxy]-25-(1-octenyl)-26,27-cyclo-9,10-secocholesta-5,7,10(19),22-tetraen-24-ol 245b are obtained in succession as colorless foams.

$^1$H-NMR (300 MHz, $CD_2Cl_2$): 245a: δ=0.03 ppm (s, 12H); 0.24 (m, 2H); 0.43 (m, 2H); 0.54 (s, 3H); 0.86 (t, 3H); 0.87 (s, 18H); 1.02 (d, 3H); 3.50 (m, 1H); 4.18 (m, 1H); 4.37 (m, 1H); 4.85 (s, 1H); 5.16 (s, 1H); 5.42 (m, 2H); 5.50 (m, 2H); 6.00 (d, 1H); 6.23 (d, 1H)

245b: δ=0.03 ppm (s, 12H); 0.24 (m, 2H); 0.43 (m, 2H); 0.54 (s, 3H); 0.87 (t, 3H); 0.87 (s, 18H); 1.03 (d, 3H); 3.48 (d, 1H); 4.17 (m, 1H); 4.37 (m, 1H); 4.83 (s, 1H); 5.17 (s, 1H); 5.39 (m, 2H); 5.51 (m, 2H); 6.01 (d, 1H); 6.24 (d, 1H)

247. 48 mg of 245a is reacted analogously to 154., and 26 mg of title compound 246a is obtained as a colorless foam.

$^1$H-NMR (300 MHz, $CD_2Cl_2$): δ=0.55 ppm (m, 2H); 0.58 (s, 3H); 0.69 (m, 2H); 0.90 (t, 3H); 1.04 (d, 3H); 3.53 (d, 1H); 4.18 (m, 1H); 4.38 (m, 1H); 4.98 (s, 1H); 5.29 (s, 1H); 5.47 (m, 2H);

5.52 (m, 2H); 6.01 (d, 1H); 6.37 (d, 1H) 248. 40 mg of 245b is reacted analogously to 154., and 16 mg of title compound 246b is obtained as a colorless foam.

$^1$H-NMR (300 MHz, $CD_2Cl_2$): δ=0.54 ppm (m, 2H); 0.59 (s, 3H); 0.68 (s, 3H); 0.89 (t, 3H); 1.04 (d, 3H); 3.50 (d, 1H); 4.17 (m, 1H); 4.38 (m, 1H); 4.97 (s, 1H); 5.29 (s, 1H); 5.40 (m, 2H); 5.51 (m, 2H); 6.01 (d, 1H); 6.38 (d, 1H)

What is claimed is:
1. A vitamin D compound of formula I, in which
$Y_1$ means a hydrogen atom, a hydroxyl group, a fluorine, chlorine or bromine atom or a group —$OCOR_8$, in which
$R_8$ is an aliphatic or aromatic radical with 1 to 12 C atoms,
$Y_2$ means a hydrogen atom or a group —(CO)$R_9$, in which
$R_9$ is an aliphatic or aromatic radical with 1 to 12 C atoms,
$R_1$ and $R_2$ are together an exocyclic methylene group,
$R_3$ and $R_4$, independently of one another, mean a hydrogen atom or an alkyl group with 1 to 4 carbon atoms,
V and W together mean an E-double bond,
Q means a straight-chain or branched carbon unit with up to 10 carbon atoms, which at any position can have α- or β-hydroxyl groups, which in turn can be etherified or esterified, keto groups, amino groups or halogen atoms,
Z means a straight-chain or branched-chain, saturated or unsaturated hydrocarbon radical with up to 12 carbon atoms, which at any positions can have keto groups, α- or β-hydroxyl groups, which in turn can be etherified or esterified, amino groups, chlorine, or bromine atoms
wherein Q is not —CHOH—.

2. A compound according to claim 1, wherein Q means an unsubstituted, unbranched alkylene unit with 1 or 2 carbon atoms, and Z means a straight-chain 1-oxoalkyl radical.

3. A compound according to claim 1, wherein Q means a —CH(OH)—CH$_2$—CH$_2$— radical, and Z means a straight-chain 1-oxoalkyl radical.

4. A compound selected from:
(5Z,7E,22E)-(1S,3R)-25-Acetyl-26,27-cyclo-9,10-secocholesta-5,7,10(19),22-tetraene-1,3-diol,
(5Z,7E,22E)-(1S,3R)-25-(1-oxopropyl)-26,27-cyclo-9,10-secocholesta-5,7,10(19),22-tetraene-1,3-diol,
(5Z,7E,22E)-(1S,3R)-25-(1-oxobutyl)-26,27-cyclo-9,10-secocholesta-5,7,10(19),22-tetraene-1,3-diol,
(5Z,7E,22E)-(1S,3R)-25-(1-oxopentyl)-26,27-cyclo-9,10-secocholesta-5,7,10(19),22-tetraene-1,3-diol,
(5Z,7E,22E)-(1S,3R)-25-(1-oxohexyl)-26,27-cyclo-9,10-secocholesta-5,7,10(19),22-tetraene-1,3-diol,
(5Z,7E,22E)-(1S,3R)-25-(1-oxoheptyl)-26,27-cyclo-9,10-secocholesta-5,7,10(19),22-tetraene-1,3-diol,
(5Z,7E,22E)-(1S,3R)-25-(1-oxooctyl)-26,27-cyclo-9,10-secocholesta-5,7,10(19),22-tetraene-1,3-diol, (5Z,7E,22E)-(1S,3R)-25-(1-oxononyl)-26,27-cyclo-9,10-secocholesta-5,7,10(19),22-tetraene-1,3-diol,
(5Z,7E,22E)-(1S,3R)-25-(1-oxodecyl)-26,27-cyclo-9,10-secocholesta-5,7,10(19),22-tetraene-1,3-diol,
(5Z,7E,22E)-(1S,3R)-25-acetyl-26,27-cyclo-24a-homo-9,10-secocholesta-5,7,10(19),22-tetraene-1,3-diol,
(5Z,7E,22E)-(1S,3R)-25-(1-oxopropyl)-26,27-cyclo-24a-homo-9,10-secocholesta-5,7,10(19),22-tetraene-1,3-diol,
(5Z,7E,22E)-(1S,3R)-25-(1-oxobutyl)-26,27-cyclo-24a-homo-9,10-secocholesta-5,7,10(19),22-tetraene-1,3-diol,
(5Z,7E,22E)-(1S,3R)-25-(1-oxopentyl)-26,27-cyclo-24a-homo-9,10-secocholesta-5,7,10(19),22-tetraene-1,3-diol,
(5Z,7E,22E)-(1S,3R)-25-(1-oxohexyl)-26,27-cyclo-24a-homo-9,10-secocholesta-5,7,10(19),22-tetraene-1,3-diol,
(5Z,7E,22E)-(1S,3R)-25-(1-oxoheptyl)-26,27-cyclo-24a-homo-9,10-secocholesta-5,7,10(19),22-tetraene-1,3-diol,
(5Z,7E,22E)-(1S,3R)-25-(1-oxooctyl)-26,27-cyclo-24a-homo-9,10-secocholesta-5,7,10(19),22-tetraene-1,3-diol,
(5Z,7E,22E)-(1S,3R)-25-(1-oxononyl)-26,27-cyclo-24a-homo-9,10-secocholesta-5,7,10(19),22-tetraene-1,3-diol,
(5Z,7E,22E)-(1S,3R)-25-(1-oxodecyl)-26,27-cyclo-24a-homo-9,10-secocholesta-5,7,10(19),22-tetraene-1,3-diol,
(5Z,7E,22E)-(1S,3R,24R)-25-acetyl-26,27-cyclo-24a,24b-dihomo-9,10-secocholesta-5,7,10(19),22-tetraene-1,3,24-triol,
(5Z,7E,22E)-(1S,3R,24S)-25-acetyl-26,27-cyclo-24a,24b-dihomo-9,10-secocholesta-5,7,10(19),22-tetraene-1,3,24-triol,
(5Z,7E,22E)-(1S,3R,24R)-25-(1-oxopropyl)-26,27-cyclo-24a,24b-dihomo-9, 10-secocholesta-5,7,10(19),22-tetraene-1,3,24-triol,
(5Z,7E,22E)-(1S,3R,24S)-25-(1-oxopropyl)-26,27-cyclo-24a,24b-dihomo-9, 10-secocholesta-5,7,10(19),22-tetraene-1,3,24-triol,
(5Z,7E,22E)-(1S,3R,24R)-25-(1-oxobutyl)-26,27-cyclo-24a,24b-dihomo-9,10-secocholesta-5,7,10(19),22-tetraene-1,3,24-triol,
(5Z,7E,22E)-(1S,3R,24S)-25-(1-oxobutyl)-26,27-cyclo-24a,24b-dihomo-9,10-secocholesta-5,7,10(19),22-tetraene-1,3,24-triol,
(5Z,7E,22E)-(1S,3R,24R)-25-(1-oxopentyl)-26,27-cyclo-24a,24b-dihomo-9,10-secocholesta-5,7,10(19),22-tetraene-1,3,24-triol,
(5Z,7E,22E)-(1S,3R,24S)-25-(1-oxopentyl)-26,27-cyclo-24a,24b-dihomo-9,10-secocholesta-5,7,10(19),22-tetraene-1,3,24-triol,
(5Z,7E,22E)-(1S,3R,24R)-25-(1-oxohexyl)-26,27-cyclo-24a,24b-dihomo-9,10-secocholesta-5,7,10(19),22-tetraene-1,3,24-triol,
(5Z,7E,22E)-(1S,3R,24S)-25-(1-oxohexyl)-26,27-cyclo-24a,24b-dihomo-9,10-secocholesta-5,7,10(19),22-tetraene-1,3,24-triol,
(5Z,7E,22E)-(1S,3R,24R)-25-(1-oxoheptyl)-26,27-cyclo-24a,24b-dihomo-9,10-secocholesta-5,7,10(19),22-tetraene-1,3,24-triol,
(5Z,7E,22E)-(1S,3R,24S)-25-(1-oxoheptyl)-26,27-cyclo-24a,24b-dihomo-9,10-secocholesta-5,7,10(19),22-tetraene-1,3,24-triol,
(5Z,7E,22E)-(1S,3R,24R)-25-(1-oxooctyl)-26,27-cyclo-24a,24b-dihomo-9,10-secocholesta-5,7,10(19),22-tetraene-1,3,24-triol,
(5Z,7E,22E)-(1S,3R,24S)-25-(1-oxooctyl)-26,27-cyclo-24a,24b-dihomo-9,10-secocholesta-5,7,10(19),22-tetraene-1,3,24-triol,
(5Z,7E,22E)-(1S,3R,24R)-25-(1-oxononyl)-26,27-cyclo-24a,24b-dihomo-9,10-secocholesta-5,7,10(19),22-tetraene-1,3,24-triol,
(5Z,7E,22E)-(1S,3R,24S)-25-(1-oxononyl)-26,27-cyclo-24a,24b-dihomo-9,10-secocholesta-5,7,10(19),22-tetraene-1,3,24-triol,
(5Z,7E,22E)-(1S,3R,24R)-25-(1-oxodecyl)-26,27-cyclo-24a,24b-dihomo-9,10-secocholesta-5,7,10(19),22-tetraene-1,3,24-triol,
(5Z,7E,22E)-(1S,3R,24S)-25-(1-oxodecyl)-26,27-cyclo-24a,24b-dihomo-9,10-secocholesta-5,7,10(19),22-tetraene-1,3,24-triol,
(5Z,7E,22E)-(1S,3R,24R)-25-acetyl-24-methoxy-26,27-cyclo-24a,24b-dihomo-9,10-secocholesta-5,7,10(19),22-tetraene-1,3-diol,
(5Z,7E,22E)-(1S,3R,24S)-25-acetyl-24-methoxy-26,27-cyclo-24a,24b-dihomo-9,10-secocholesta-5,7,10(19),22-tetraene-1,3-diol,
(5Z,7E,22E)-(1S,3R,24R)-24-methoxy-25-(1-oxopropyl)-26,27-cyclo-24a,24b-dihomo-9,10-secocholesta-5,7,10(19),22-tetraene-1,3-diol,
(5Z,7E,22E)-(1S,3R,24S)-24-methoxy-25-(1-oxopropyl)-26,27-cyclo-24a,24b-dihomo-9,10-secocholesta-5,7,10(19),22-tetraene-1,3-diol,
(5Z,7E,22E)-(1S,3R,24R)-24-methoxy-25-(1-oxobutyl)-26,27-cyclo-24a,24b-dihomo-9,10-secocholesta-5,7,10(19),22-tetraene-1,3-diol,
(5Z,7E,22E)-(1S,3R,24S)-24-methoxy-25-(1-oxobutyl)-26,27-cyclo-24a,24b-dihomo-9,10-secocholesta-5,7,10(19),22-tetraene-1,3-diol,
(5Z,7E,22E)-(1S,3R,24R)-24-methoxy-25-(1-oxopentyl)-26,27-cyclo-24a,24b-dihomo-9,10-secocholesta-5,7,10(19),22-tetraene-1,3-diol,
(5Z,7E,22E)-(1S,3R,24S)-24-methoxy-25-(1-oxopentyl)-26,27-cyclo-24a,24b-dihomo-9,10-secocholesta-5,7,10(19),22-tetraene-1,3-diol,
(5Z,7E,22E)-(1S,3R,24R)-24-methoxy-25-(1-oxohexyl)-26,27-cyclo-24a,24b-dihomo-9,10-secocholesta-5,7,10(19),22-tetraene-1,3-diol,
(5Z,7E,22E)-(1S,3R,24S)-24-methoxy-25-(1-oxohexyl)-26,27-cyclo-24a,24b-dihomo-9,10-secocholesta-5,7,10(19),22-tetraene-1,3-diol,
(5Z,7E,22E)-(1S,3R,24R)-24-methoxy-25-(1-oxoheptyl)-26,27-cyclo-24a,24b-dihomo-9,10-secocholesta-5,7,10(19),22-tetraene-1,3-diol,
(5Z,7E,22E)-(1S,3R,24S)-24-methoxy-25-(1-oxoheptyl)-26,27-cyclo-24a,24b-dihomo-9,10-secocholesta-5,7,10(19),22-tetraene-1,3-diol,
(5Z,7E,22E)-(1S,3R,24R)-24-methoxy-25-(1-oxooctyl)-26,27-cyclo-24a,24b-dihomo-9,10-secocholesta-5,7,10(19),22-tetraene-1,3-diol,
(5Z,7E,22E)-(1S,3R,24S)-24-methoxy-25-(1-oxooctyl)-26,27-cyclo-24a,24b-dihomo-9,10-secocholesta-5,7,10(19),22-tetraene-1,3-diol,
(5Z,7E,22E)-(1S,3R,24R)-24-methoxy-25-(1-oxononyl)-26,27-cyclo-24a,24b-dihomo-9,10-secocholesta-5,7,10(19),22-tetraene-1,3-diol,
(5Z,7E,22E)-(1S,3R,24S)-24-methoxy-25-(1-oxononyl)-26,27-cyclo-24a,24b-dihomo-9,10-secocholesta-5,7,10(19),22-tetraene-1,3-diol,
(5Z,7E,22E)-(1S,3R,24R)-24-methoxy-25-(1-oxodecyl)-26,27-cyclo-24a,24b-dihomo-9,10-secocholesta-5,7,10(19),22-tetraene-1,3-diol,
(5Z,7E,22E)-(1S,3R,24S)-24-methoxy-25-(1-oxodecyl)-26,27-cyclo-24a,24b-dihomo-9,10-secocholesta-5,7,10(19),22-tetraene-1,3-diol,
(5Z,7E,22E)-(1S,3R,24S)-25-methyl-26,27-cyclo-9,10-secocholesta-5,7,10(19),22-tetraene-1,3,24-triol,
(5Z,7E,22E)-(1S,3R,24R)-25-methyl-26,27-cyclo-9,10-secocholesta-5,7,10(19),22-tetraene-1,3,24-triol, (5Z,7E,22E)-(1S,3R,24S)-25-ethyl-26,27-cyclo-9,10-secocholesta-5,7,10(19),22-tetraene-1,3,24-triol,
(5Z,7E,22E)-(1S,3R,24R)-25-ethyl-26,27-cyclo-9,10-secocholesta-5,7,10(19),22-tetraene-1,3,24-triol,
(5Z,7E,22E)-(1S,3R,24S)-25-propyl-26,27-cyclo-9,10-secocholesta-5,7,10(19),22-tetraene-1,3,24-triol,
(5Z,7E,22E)-(1S,3R,24R)-25-propyl-26,27-cyclo-9,10-secocholesta-5,7,10(19),22-tetraene-1,3,24-triol,
(5Z,7E,22E)-(1S,3R,24S)-25-butyl-26,27-cyclo-9,10-secocholesta-5,7,10(19),22-tetraene-1,3,24-triol,
(5Z,7E,22E)-(1S,3R,24R)-25-butyl-26,27-cyclo-9,10-secocholesta-5,7,10(19),22-tetraene-1,3,24-triol,
(5Z,7E,22E)-(1S,3R,24S)-25-pentyl-26,27-cyclo-9,10-secocholesta-5,7,10(19),22-tetraene-1,3,24-triol,
(5Z,7E,22E)-(1S,3R,24R)-25-pentyl-26,27-cyclo-9,10-secocholesta-5,7,10(19),22-tetraene-1,3,24-triol,
(5Z,7E,22E)-(1S,3R,24S)-25-hexyl-26,27-cyclo-9,10-secocholesta-5,7,10(19),22-tetraene-1,3,24-triol,
(5Z,7E,22E)-(1S,3R,24R)-25-hexyl-26,27-cyclo-9,10-secocholesta-5,7,10(19),22-tetraene-1,3,24-triol,
(5Z,7E,22E)-(1S,3R,24S)-25-heptyl-26,27-cyclo-9,10-secocholesta-5,7,10(19),22-tetraene-1,3,24-triol,
(5Z,7E,22E)-(1S,3R,24R)-25-heptyl-26,27-cyclo-9,10-secocholesta-5,7,10(19),22-tetraene-1,3,24-triol,
(5Z,7E,22E)-(1S,3R,24S)-25-octyl-26,27-cyclo-9,10-secocholesta-5,7,10(19),22-tetraene-1,3,24-triol,
(5Z,7E,22E)-(1S,3R,24R)-25-octyl-26,27-cyclo-9,10-secocholesta-5,7,10(19),22-tetraene-1,3,24-triol,
(5Z,7E,22E)-(1S,3R,24S)-25-nonyl-26,27-cyclo-9,10-secocholesta-5,7,10(19),22-tetraene-1,3,24-triol,
(5Z,7E,22E)-(1S,3R,24R)-25-nonyl-26,27-cyclo-9,10-secocholesta-5,7,10(19),22-tetraene-1,3,24-triol,
(5Z,7E,22E)-(1S,3R,24S)-25-decyl-26,27-cyclo-9,10-secocholesta-5,7,10(19),22-tetraene-1,3,24-triol,
(5Z,7E,22E)-(1S,3R,24R)-25-decyl-26,27-cyclo-9,10-secocholesta-5,7,10(19),22-tetraene-1,3,24-triol,
(5Z,7E,22E)-(1S,3R,24S)-25-ethylene-26,27-cyclo-9,10-secocholesta-5,7,10(19),22-tetraene-1,3,24-triol,
(5Z,7E,22E)-(1S,3R,24R)-25-ethylene-26,27-cyclo-9,10-secocholesta-5,7,10(19),22-tetraene-1,3,24-triol,
[5Z,7E,22E,25(E)]-(1S,3R,24S)-25-(1-propenyl)-26,27-cyclo-9,10-secocholesta-5,7,10(19),22-tetraene-1,3,24-triol,
[5Z,7E,22E,25(E)]-(1S,3R,24R)-25-(1-propenyl)-26,27-cyclo-9,10-secocholesta-5,7,10(19),22-tetraene-1,3,24-triol,
[5Z,7E,22E,25(E)]-(1S,3R,24S)-25-(1-butenyl)-26,27-cyclo-9,10-secocholesta-5,7,10(19),22-tetraene-1,3,24-triol,
[5Z,7E,22E,25(E)]-(1S,3R,24R)-25-(1-butenyl)-26,27-cyclo-9,10-secocholesta-5,7,10(19),22-tetraene-1,3,24-triol,
[5Z,7E,22E,25(E)]-(1S,3R,24S)-25-(1-pentenyl)-26,27-cyclo-9,10-secocholesta-5,7,10(19),22-tetraene-1,3,24-triol,
[5Z,7E,22E,25(E)]-(1S,3R,24R)-25-(1-pentenyl)-26,27-cyclo-9,10-secocholesta-5,7,10(19),22-tetraene-1,3,24-triol,
[5Z,7E,22E,25(E)]-(1S,3R,24S)-25-(1-hexenyl)-26,27-cyclo-9,10-secocholesta-5,7,10(19),22-tetraene-1,3,24-triol,
[5Z,7E,22E,25(E)]-(1S,3R,24R)-25-(1-hexenyl)-26,27-cyclo-9,10-secocholesta-5,7,10(19),22-tetraene-1,3,24-triol,
[5Z,7E,22E,25(E)]-(1S,3R,24S)-25-(1-heptenyl)-26,27-cyclo-9,10-secocholesta-5,7,10(19),22-tetraene-1,3,24-triol,
[5Z,7E,22E,25(E)]-(1S,3R,24R)-25-(1-heptenyl)-26,27-cyclo-9,10-secocholesta-5,7,10(19),22-tetraene-1,3,24-triol,
[5Z,7E,22E,25(E)]-(1S,3R,24S)-25-(1-octenyl)-26,27-cyclo-9,10-secocholesta-5,7,10(19),22-tetraene-1,3,24-triol,
[5Z,7E,22E,25(E)]-(1S,3R,24R)-25-(1-octenyl)-26,27-cyclo-9,10-secocholesta-5,7,10(19),22-tetraene-1,3,24-triol,
[5Z,7E,22E,25(E)]-(1S,3R,24S)-25-(1-nonenyl)-26,27-cyclo-9,10-secocholesta-5,7,10(19),22-tetraene-1,3,24-triol,
[5Z,7E,22E,25(E)]-(1S,3R,24R)-25-(1-nonenyl)-26,27-cyclo-9,10-secocholesta-5,7,10(19),22-tetraene-1,3,24-triol,
[5Z,7E,22E,25(E)]-(1S,3R,24S)-25-(1-decenyl)-26,27-cyclo-9,10-secocholesta-5,7,10(19),22-tetraene-1,3,24-triol,
[5Z,7E,22E,25(E)]-(1S,3R,24R)-25-(1-decenyl)-26,27-cyclo-9,10-secocholesta-5,7,10(19),22-tetraene-1,3,24-triol,
[5Z,7E,22E,25(Z)]-(1S,3R,24S)-25-(1-propenyl)-26,27-cyclo-9,10-secocholesta-5,7,10(19),22-tetraene-1,3,24-triol,
[5Z,7E,22E,25(Z)]-(1S,3R,24R)-25-(1-propenyl)-26,27-cyclo-9,10-secocholesta-5,7,10(19),22-tetraene-1,3,24-triol,
[5Z,7E,22E,25(Z)]-(1S,3R,24S)-25-(1-butenyl)-26,27-cyclo-9,10-secocholesta-5,7,10(19),22-tetraene-1,3,24-triol,
[5Z,7E,22E,25(Z)]-(1S,3R,24R)-25-(1-butenyl)-26,27-cyclo-9,10-secocholesta-5,7,10(19),22-tetraene-1,3,24-triol,
[5Z,7E,22E,25(Z)]-(1S,3R,24S)-25-(1-pentenyl)-26,27-cyclo-9,10-secocholesta-5,7,10(19),22-tetraene-1,3,24-triol,
[5Z,7E,22E,25(Z)]-(1S,3R,24R)-25-(1-pentenyl)-26,27-cyclo-9,10-secocholesta-5,7,10(19),22-tetraene-1,3,24-triol,
[5Z,7E,22E,25(Z)]-(1S,3R,24S)-25-(1-hexenyl)-26,27-cyclo-9,10-secocholesta-5,7,10(19),22-tetraene-1,3,24-triol,
[5Z,7E,22E,25(Z)]-(1S,3R,24R)-25-(1-hexenyl)-26,27-cyclo-9,10-secocholesta-5,7,10(19),22-tetraene-1,3,24-triol,
[5Z,7E,22E,25(Z)]-(1S,3R,24S)-25-(1-heptenyl)-26,27-cyclo-9,10-secocholesta-5,7,10(19),22-tetraene-1,3,24-triol,
[5Z,7E,22E,25(Z)]-(1S,3R,24R)-25-(1-heptenyl)-26,27-cyclo-9,10-secocholesta-5,7,10(19),22-tetraene-1,3,24-triol,
[5Z,7E,22E,25(Z)]-(1S,3R,24S)-25-(1-octenyl)-26,27-cyclo-9,10-secocholesta-5,7,10(19),22-tetraene-1,3,24-triol,
[5Z,7E,22E,25(Z)]-(1S,3R,24R)-25-(1-octenyl)-26,27-cyclo-9,10-secocholesta-5,7,10(19),22-tetraene-1,3,24-triol,
[5Z,7E,22E,25(Z)]-(1S,3R,24S)-25-(1-nonenyl)-26,27-cyclo-9,10-secocholesta-5,7,10(19),22-tetraene-1,3,24-triol,
[5Z,7E,22E,25(Z)]-(1S,3R,24R)-25-(1-nonenyl)-26,27-cyclo-9,10-secocholesta-5,7,10(19),22-tetraene-1,3,24-triol,
[5Z,7E,22E,25(Z)]-(1S,3R,24S)-25-(1-decenyl)-26,27-cyclo-9,10-secocholesta-5,7,10(19),22-tetraene-1,3,24-triol, and
[5Z,7E,22E,25(Z)]-(1S,3R,24R)-25-(1-decenyl)-26,27-cyclo-9,10-secocholesta-5,7,10(19),22-tetraene-1,3,24-triol.

5. A process for the production of compounds according to claim 1, comprising:
converting a compound of formula II

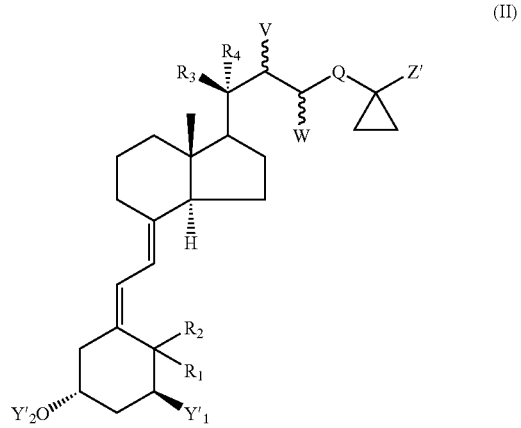

(II)

in which
Y'$_1$ means a hydrogen atom, a halogen atom, or a protected hydroxyl group, Y'₂ means a hydroxy protective group, and Z' means a straight-chain or branched-chain, saturated or unsaturated hydrocarbon radical with up to 12 carbon atoms, which at any positions can have protected keto groups, protected α- or β-hydroxyl groups, which in turn can be etherified or esterified, amino groups, chlorine, or bromine atoms into a compound of formula I by simultaneous or successive cleavage of the hydroxy and keto protective groups and optionally by partial or complete esterification of free hydroxyl groups.

6. A pharmaceutical composition comprising a compound according to claim 1 and a pharmaceutically acceptable carrier.

7. A vitamin D compound wherein said compound is:
(5Z,7E,22E)-(1S,3R,24S)-25-ethyl-26,27-cyclo-9,10-secocholesta-5,7,10(19),22-tetraene-1,3,24-triol,
(5Z,7E,22E)-(1S,3R,24R)-25-ethyl-26,27-cyclo-9,10-secocholesta-5,7,10(19),22-tetraene-1,3,24-triol,
[5Z,7E,22E,25(Z)]-(1S,3R,24S)-25-(1-butenyl)-26,27-cyclo-9,10-secocholesta-5,7,10(19),22-tetraene-1,3,24-triol,
[5Z,7E,22E,25(E)]-(1S,3R,24S)-25-(1-butenyl)-26,27-cyclo-9,10-secocholesta-5,7,10(19),22-tetraene-1,3-24-triol,
[5Z,7E,22E,25(E)]-(1S,3R,24R)-25-(1-butenyl)-26,27-cyclo-9,10-secocholesta-5,7,10(19),22-tetraene-1,3,24-triol,
(5Z,7E,22E)-(1S,3R,24S)-25-butyl-26,27-cyclo-9,10-secocholesta-5,7,10(19),22-tetraene-1,3,24-triol,
(5Z,7E,22E)-(1S, 3R, 24R)-25-butyl-26,27,-cyclo-9,10-secocholesta-5,7,10(19),22-tetraene-1,3,24-triol,
(5Z,7E,22E)-(1S,3R,24S)-25-hexyl-26,27-cyclo-9,10-secocholesta-5,7,10(19),22-tetraene-1,3,24-triol,
(5Z,7E,22E)-(1S,3R,24R)-25-hexyl-26,27-cyclo-9,10-secocholesta-5,7,10(19),22-tetraene-1,3,24-triol,
(5Z,7E,22E)-(1S,3R,24S)-25-heptyl-26,27-cyclo-9,10-secocholesta-5,7,10(19),22-tetraene-1,3,24-triol,
(5Z,7E,22E)-(1S,3R,24R)-25-heptyl-26,27-cyclo-9,10-secocholesta-5,7,10(19),22-tetraene-1,3,24-triol,
(5Z,7E,22E)-(1S,3R,24S)-25-octyl-26,27-cyclo-9,10-secocholesta-5,7,10(19),22-tetraene-1,3,24-triol,
(5Z,7E,22E)-(1S,3R,24S)-25-octyl-26,27-cyclo-9,10-secocholesta-5,7,10(19),22-tetraene-1,3-24-triol,
(5Z,7E,22E)-(1S,3R,24R)-25-octyl-26,27-cyclo-9,10-secocholesta-5,7,10(19),22-tetraene-1,3,24-triol,
[5Z,7E,22E, 25(Z)]-(1S,3R,24S)-25-(1-octenyl)-26,27-cyclo-9,10-secocholesta-5,7,10(19),22-tetraene-1,3,24-triol, or
[5Z,7E,22E,25(Z)]-(1S,3R,24S)-25-(1-octenyl)-26,27-cyclo-9,10-secocholesta-5,7,10(19),22-tetraene-1,3,24-triol.

8. A compound according to claim 1, wherein $R_3$ is H and $R_4$ is methyl, $R_3$ is methyl and $R_4$ is H, or $R_3$ is methyl and $R_4$ is methyl.

9. A compound according to claim 1, wherein $R_8$ and $R_9$ are each independently methyl, ethyl, propyl, i-propyl, butyl or phenyl.

10. A compound according to claim 1, wherein Q is —CH₂—, —(CH₂)₂—, —(CH₂)₃—, —(CH₂)₄—, —(CH₂)₇—, —CH₂—C(CH₃)₂—CH₂—, —CH₂—CH(CH₃)—CH₂—CH(CH₃)—CH₂—, —CH₂—CH(OH)—, —CH₂—CH₂—CH(OH)—, —CH(OH)—CH₂—, —CH(OH)—CH₂—CH₂—, —CH₂—CH(OH)—CH₂—CH(OH)—CH₂—, —CH₂—CH(OH)—CH₂—, —CH₂—CH(OH)—CH₂—CH(OH)—CH₂—, —CH(OCH₃)—, —CH₂—CH(OC₂H₅)—, —CH₂—CH(OCOCH₃)—CH₂—CH(OCOCH₃)—CH₂—CH(OCOC₄H₉)—CH₂—, —CO—CH₂—, —CO—CH₂—CH₂—, —CH₂COCH₂—, —CH(Cl)—, —CH(Cl)—CH₂—, —CH₂—CH(Cl)—, —CH(NH₂)—, —CH(NH₂)—CH₂—, —CH(N(CH₃)₂)—, —CH(N(CH₃)₂)—CH₂—, —CH₂—CH(N(CH₃)₂)—CH₂—CH(N(CH₃)₂)—CH₂—, —CH(F)—, —CH(F)—CH₂—, —CH₂—CH(F)—CH₂—.

11. A compound according to claim 1, wherein Q is an unsubstituted, unbranched alkylene with 1–3 carbon atoms, —CH(OH)—CH₂— or —CH(OH)—CH₂—CH₂—.

12. A compound according to claim 1, wherein Z is —CH₃, —CH₂—CH₃, —(CH₂)₂—CH₃, —(CH₂)₃—CH₃, —(CH₂)₄—CH₃, —(CH₂)₅—CH₃, —(CH₂)₆—CH₃, —(CH₂)₇—CH₃, —CH₂—C(CH₃)₂—CH₂—CH₃, —CH₂—CH(CH₃)—CH₂—CH(CH₃)—CH₂—CH₃, —CH(OH)—CH₃, —CH₂—CH(OH)—CH₃, —CH₂—CH(OH)—CH₂—CH(OH)—CH₂—CH₃, —CH(OCH₃)—CH₃, —CH₂—CH(OC₂H₅)—CH₃, —CH₂—CH(OCOCH₃)—CH₂—CH(OCOCH₃)—CH₂—CH₃, —CH₂—CH(OCOC₄H₉)—CH₂—CH₃, —CH₂COCH₂—CH₃, —CH₂—CH(Cl)—CH₃, —CH₂—CH(N(CH₃)₂)—CH₂—CH(N(CH₃)₂)—CH₂—CH₃, —CH₂—CH(F)—CH₂—CH₃.

13. A compound according to claim 1, wherein Z is 1-oxoalkyl having 1–12 C atoms, alkyl having 1–12 C atoms or alkenyl having 1–12 C atoms.

14. A compound according to claim 13, wherein Z is 1-oxopropyl, 1-oxobutyl, 1-oxopentyl, 1-oxohexyl, 1-oxoheptyl, 1-oxooctyl, 1-oxononyl, 1-oxodecyl, acetyl, methyl, ethyl, propyl, butyl, pentyl, hexyl, heptyl, octyl, nonyl, decyl, 1-propenyl, 1-butenyl, 1-pentenyl, 1-hexeynyl, 1-heptenyl, 1-oxtenyl, 1-nonenyl, or 1-decenyl.

15. A method of preparing a pharmaceutical composition comprising combining a compound according to claim 1 with a pharmaceutically compatible vehicle.

16. A vitamin D compound of formula I,

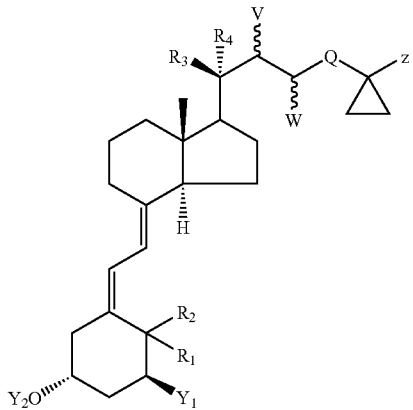

in which $Y_1$ means a hydrogen atom, a hydroxyl group, a fluorine, chlorine or bromine atom or a group —OCOR₈, in which $R_8$ is an aliphatic or aromatic radical with 1 to 12 C atoms, $Y_2$ means a hydrogen atom or a group —(CO)R₉, in which $R_9$ is an aliphatic or aromatic radical with 1 to 12 C atoms, $R_1$ and $R_2$ are together an exocyclic methylene group, $R_3$ and $R_4$, independently of one another, mean a hydrogen atom or an alkyl group with 1 to 4 carbon atoms, V and W together mean an E-double bond, Q means an unsubstituted, unbranched alkylene unit with 1 or 2 carbon atoms, and Z means a straight-chain or branched-chain, saturated or unsaturated hydrocarbon radical with up to 12 carbon atoms, which at any positions can have keto groups, - or hydroxyl groups, which in turn can be etherified or esterified, amino groups, chlorine, or bromine atoms.

17. A compound according to claim 1, wherein Z is —$CH_3$, —$CH_2$—$CH_3$, —$(CH_2)_2$—$CH_3$, —$(CH_2)_3$—$CH_3$, —$(CH_2)_4$—$CH_3$, —$(CH_2)_5$—$CH_3$, —$(CH_2)_6$—$CH_3$, —$(CH_2)_7$—$CH_3$, —$CH_2$—$C(CH_3)_2$—$CH_2$—$CH_3$, or —$CH_2$—$CH(CH_3)$—$CH_2$—$CH(CH_3)$—$CH_2$—$CH_3$.

18. A compound according to claim 1, wherein Z is —$CH(OH)$—$CH_3$, —$CH_2$—$CH(OH)$—$CH_3$, —$CH_2$—$CH(OH)$—$CH_2$—$CH(OH)$—$CH_2$—$CH_3$, —$CH_2$—$CH(OH)$—$CH_2$—$CH_3$, or —$CH_2$—$CH(OH)$—$CH_2$—$CH(OH)$—$CH_2$—$CH_3$.

19. A compound according to claim 1, wherein Z is —$CH(OCH_3)$—$CH_3$, —$CH_2$—$CH(OC_2H_5)$—$CH_3$, —$CH_2$—$CH(OCOCH_3)$—$CH_2$—$CH(OCOCH_3)$—$CH_2$—$CH_3$, or —$CH_2$—$CH(OCOC_4H_9)$—$CH_2$—$CH_3$.

20. A compound according to claim 1, wherein Z is —$CH_2COCH_2$—$CH_3$, —$CH_2$—$CH(Cl)$—$CH_3$, —$CH_2$—$CH(N(CH_3)_2)$—$CH_2$—$CH(N(CH_3)_2)$—$CH_2$—$CH_3$, or —$CH_2$—$CH(F)$—$CH_2$—$CH_3$.

21. A compound according to claim 1, wherein Z is a 1-oxoalkyl group with 1–12 carbon atoms, an alkyl group with 1–12 carbon atoms, or an alkenyl group with 1–12 carbon atoms, in which the double bond can have E- or Z-geometry and can be present at any position.

22. A compound according to claim 4, wherein said compound is (5Z,7E,22E)-(1S,3R)-25-Acetyl-26,27-cyclo-9,10-secocholesta-5,7,10(19),22-tetraene-1,3-diol, (5Z,7E,22E)-(1S,3R)-25-(1-oxopropyl)-26,27-cyclo-9,10-secocholesta-5,7,10(19),22-tetraene-1,3-diol, (5Z,7E,22E)-(1S,3R)-25-(1-oxobutyl)-26,27-cyclo-9,10-secocholesta-5,7,10(19),22-tetraene-1,3-diol, (5Z,7E,22E)-(1S,3R)-25-(1-oxopentyl)-26,27-cyclo-9,10-secocholesta-5,7,10(19),22-tetraene-1,3-diol, (5Z,7E,22E)-(1S,3R)-25-(1-oxohexyl)-26,27-cyclo-9,10-secocholesta-5,7,10(19),22-tetraene-1,3-diol, (5Z,7E,22E)-(1S,3R)-25-(1-oxoheptyl)-26,27-cyclo-9,10-secocholesta-5,7,10(19),22-tetraene-1,3-diol, (5Z,7E,22E)-(1S,3R)-25-(1-oxooctyl)-26,27-cyclo-9,10-secocholesta-5,7,10(19),22-tetraene-1,3-diol, (5Z,7E,22E)-(1S,3R)-25-(1-oxononyl)-26,27-cyclo-9,10-secocholesta-5,7,10(19),22-tetraene-1,3-diol, or (5Z,7E,22E)-(1S,3R)-25-(1-oxodecyl)-26,27-cyclo-9,10-secocholesta-5,7,10(19),22-tetraene-1,3-diol.

23. A compound according to claim 4, wherein said compound is (5Z,7E,22E)-(1S,3R)-25-acetyl-26,27-cyclo-24a-homo-9,10-secocholesta-5,7,10(19),22-tetraene-1,3-diol, (5Z,7E,22E)-(1S,3R)-25-(1-oxopropyl)-26,27-cyclo-24a-homo-9,10-secocholesta-5,7,10(19),22-tetraene-1,3-diol, (5Z,7E,22E)-(1S,3R)-25-(1-oxobutyl)-26,27-cyclo-24a-homo-9,10-secocholesta-5,7,10(19),22-tetraene-1,3-diol, (5Z,7E,22E)-(1S,3R)-25-(1-oxopentyl)-26,27-cyclo-24a-homo-9,10-secocholesta-5,7,10(19),22-tetraene-1,3-diol, (5Z,7E,22E)-(1S,3R)-25-(1-oxohexyl)-26,27-cyclo-24a-homo-9,10-secocholesta-5,7,10(19),22-tetraene-1,3-diol, (5Z,7E,22E)-(1S,3R)-25-(1-oxoheptyl)-26,27-cyclo-24a-homo-9,10-secocholesta-5,7,10(19),22-tetraene-1,3-diol, (5Z,7E,22E)-(1S,3R)-25-(1-oxooctyl)-26,27-cyclo-24a-homo-9,10-secocholesta-5,7,10(19),22-tetraene-1,3-diol, (5Z,7E,22E)-(1S,3R)-25-(1-oxononyl)-26,27-cyclo-24a-homo-9,10-secocholesta-5,7,10(19),22-tetraene-1,3-diol, or (5Z,7E,22E)-(1S,3R)-25-(1-oxodecyl)-26,27-cyclo-24a-homo-9,10-secocholesta-5,7,10(19),22-tetraene-1,3-diol.

24. A compound according to claim 4, wherein said compound is (5Z,7E,22E)-(1S,3R,24R)-25-acetyl-24-methoxy-26,27-cyclo-24a,24b-dihomo-9,10-secocholesta-5,7,10(19),22-tetraene-1,3-diol, (5Z,7E,22E)-(1S,3R,24S)-25-acetyl-24-methoxy-26,27-cyclo-24a,24b-dihomo-9,10-secocholesta-5,7,10(19),22-tetraene-1,3-diol, (5Z,7E,22E)-(1S,3R,24R)-24-methoxy-25-(1-oxopropyl)-26,27-cyclo-24a,24b-dihomo-9,10-secocholesta-5,7,10(19),22-tetraene-1,3-diol, (5Z,7E,22E)-(1S,3R,24S)-24-methoxy-25-(1-oxopropyl)-26,27-cyclo-24a,24b-dihomo-9,10-secocholesta-5,7,10(19),22-tetraene-1,3-diol, (5Z,7E,22E)-(1S,3R,24R)-24-methoxy-25-(1-oxobutyl)-26,27-cyclo-24a,24b-dihomo-9,10-secocholesta-5,7,10(19),22-tetraene-1,3-diol, (5Z,7E,22E)-(1S,3R,24S)-24-methoxy-25-(1-oxobutyl)-26,27-cyclo-24a,24b-dihomo-9,10-secocholesta-5,7,10(19),22-tetraene-1,3-diol, (5Z,7E,22E)-(1S,3R,24R)-24-methoxy-25-(1-oxopentyl)-26,27-cyclo-24a,24b-dihomo-9,10-secocholesta-5,7,10(19),22-tetraene-1,3-diol, (5Z,7E,22E)-(1S,3R,24S)-24-methoxy-25-(1-oxopentyl)-26,27-cyclo-24a,24b-dihomo-9,10-secocholesta-5,7,10(19),22-tetraene-1,3-diol, (5Z,7E,22E)-(1S,3R,24R)-24-methoxy-25-(1-oxohexyl)-26,27-cyclo-24a,24b-dihomo-9,10-secocholesta-5,7,10(19),22-tetraene-1,3-diol, (5Z,7E,22E)-(1S,3R,24S)-24-methoxy-25-(1-oxohexyl)-26,27-cyclo-24a,24b-dihomo-9,10-secocholesta-5,7,10(19),22-tetraene-1,3-diol, (5Z,7E,22E)-(1S,3R,24R)-24-methoxy-25-(1-oxoheptyl)-26,27-cyclo-24a,24b-dihomo-9,10-secocholesta-5,7,10(19),22-tetraene-1,3-diol, (5Z,7E,22E)-(1S,3R,24S)-24-methoxy-25-(1-oxoheptyl)-26,27-cyclo-24a,24b-dihomo-9,10-secocholesta-5,7,10(19),22-tetraene-1,3-diol, (5Z,7E,22E)-(1S,3R,24R)-24-methoxy-25-(1-oxooctyl)-26,27-cyclo-24a,24b-dihomo-9,10-secocholesta-5,7,10(19),22-tetraene-1,3-diol, (5Z,7E,22E)-(1S,3R,24S)-24-methoxy-25-(1-oxooctyl)-26,27-cyclo-24a,24b-dihomo-9,10-secocholesta-5,7,10(19),22-tetraene-1,3-diol, (5Z,7E,22E)-(1S,3R,24R)-24-methoxy-25-(1-oxononyl)-26,27-cyclo-24a,24b-dihomo-9,10-secocholesta-5,7,10(19),22-tetraene-1,3-diol, (5Z,7E,22E)-(1S,3R,24S)-24-methoxy-25-(1-oxononyl)-26,27-cyclo-24a,24b-dihomo-9,10-secocholesta-5,7,10(19),22-tetraene-1,3-diol, (5Z,7E,22E)-(1S,3R,24R)-24-methoxy-25-(1-oxodecyl)-26,27-cyclo-24a,24b-dihomo-9,10-secocholesta-5,7,10(19),22-tetraene-1,3-diol, or (5Z,7E,22E)-(1S,3R,24S)-24-methoxy-25-(1-oxodecyl)-26,27-cyclo-24a,24b-dihomo-9,10-secocholesta-5,7,10(19),22-tetraene-1,3-diol.

25. A compound according to claim 4, wherein said compound is (5Z,7E,22E)-(1S,3R,24S)-25-methyl-26,27-cyclo-9,10-secocholesta-5,7,10(19),22-tetraene-1,3,24-triol, (5Z,7E,22E)-(1S,3R,24R)-25-methyl-26,27-cyclo-9,10-secocholesta-5,7,10(19),22-tetraene-1,3,24-triol, (5Z,7E,22E)-(1S,3R,24S)-25-ethyl-26,27-cyclo-9,10-secocholesta-5,7,10(19),22-tetraene-1,3,24-triol, (5Z,7E,22E)-(1S,3R,24R)-25-ethyl-26,27-cyclo-9,10-secocholesta-5,7,10(19),22-tetraene-1,3,24-triol,
(5Z,7E,22E)-(1S,3R,24S)-25-propyl-26,27-cyclo-9,10-secocholesta-5,7,10(19),22-tetraene-1,3,24-triol,
(5Z,7E,22E)-(1S,3R,24R)-25-propyl-26,27-cyclo-9,10-secocholesta-5,7,10(19),22-tetraene-1,3,24-triol,
(5Z,7E,22E)-(1S,3R,24S)-25-butyl-26,27-cyclo-9,10-secocholesta-5,7,10(19),22-tetraene-1,3,24-triol,
(5Z,7E,22E)-(1S,3R,24R)-25-butyl-26,27-cyclo-9,10-secocholesta-5,7,10(19),22-tetraene-1,3,24-triol,
(5Z,7E,22E)-(1S,3R,24S)-25-pentyl-26,27-cyclo-9,10-secocholesta-5,7,10(19),22-tetraene-1,3,24-triol,
(5Z,7E,22E)-(1S,3R,24R)-25-pentyl-26,27-cyclo-9,10-secocholesta-5,7,10(19),22-tetraene-1,3,24-triol,
(5Z,7E,22E)-(1S,3R,24S)-25-hexyl-26,27-cyclo-9,10-secocholesta-5,7,10(19),22-tetraene-1,3,24-triol,
(5Z,7E,22E)-(1S,3R,24R)-25-hexyl-26,27-cyclo-9,10-secocholesta-5,7,10(19),22-tetraene-1,3,24-triol,
(5Z,7E,22E)-(1S,3R,24S)-25-heptyl-26,27-cyclo-9,10-secocholesta-5,7,10(19),22-tetraene-1,3,24-triol,
(5Z,7E,22E)-(1S,3R,24R)-25-heptyl-26,27-cyclo-9,10-secocholesta-5,7,10(19),22-tetraene-1,3,24-triol,
(5Z,7E,22E)-(1S,3R,24S)-25-octyl-26,27-cyclo-9,10-secocholesta-5,7,10(19),22-tetraene-1,3,24-triol,
(5Z,7E,22E)-(1S,3R,24R)-25-octyl-26,27-cyclo-9,10-secocholesta-5,7,10(19),22-tetraene-1,3,24-triol,
(5Z,7E,22E)-(1S,3R,24S)-25-nonyl-26,27-cyclo-9,10-secocholesta-5,7,10(19),22-tetraene-1,3,24-triol,
(5Z,7E,22E)-(1S,3R,24R)-25-nonyl-26,27-cyclo-9,10-secocholesta-5,7,10(19),22-tetraene-1,3,24-triol,
(5Z,7E,22E)-(1S,3R,24S)-25-decyl-26,27-cyclo-9,10-secocholesta-5,7,10(19),22-tetraene-1,3,24-triol, or
(5Z,7E,22E)-(1S,3R,24R)-25-decyl-26,27-cyclo-9,10-secocholesta-5,7,10(19),22-tetraene-1,3,24-triol.

26. A compound according to claim 4, wherein said compound is
(5Z,7E,22E)-(1S,3R,24S)-25-ethylene-26,27-cyclo-9,10-secocholesta-5,7,10(19),22-tetraene-1,3,24-triol,
(5Z,7E,22E)-(1S,3R,24R)-25-ethylene-26,27-cyclo-9,10-secocholesta-5,7,10(19),22-tetraene-1,3,24-triol,
[5Z,7E,22E,25(E)]-(1S,3R,24S)-25-(1-propenyl)-26,27-cyclo-9,10-secocholesta-5,7,10(19),22-tetraene-1,3,24-triol,
[5Z,7E,22E,25(E)]-(1S,3R,24R)-25-(1-propenyl)-26,27-cyclo-9,10-secocholesta-5,7,10(19),22-tetraene-1,3,24-triol,
[5Z,7E,22E,25(E)]-(1S,3R,24S)-25-(1-butenyl)-26,27-cyclo-9,10-secocholesta-5,7,10(19),22-tetraene-1,3,24-triol,
[5Z,7E,22E,25(E)]-(1S,3R,24R)-25-(1-butenyl)-26,27-cyclo-9,10-secocholesta-5,7,10(19),22-tetraene-1,3,24-triol,
[5Z,7E,22E,25(E)]-(1S,3R,24S)-25-(1-pentenyl)-26,27-cyclo-9,10-secocholesta-5,7,10(19),22-tetraene-1,3,24-triol,
[5Z,7E,22E,25(E)]-(1S,3R,24R)-25-(1-pentenyl)-26,27-cyclo-9,10-secocholesta-5,7,10(19),22-tetraene-1,3,24-triol,
[5Z,7E,22E,25(E)]-(1S,3R,24S)-25-(1-hexenyl)-26,27-cyclo-9,10-secocholesta-5,7,10(19),22-tetraene-1,3,24-triol,
[5Z,7E,22E,25(E)]-(1S,3R,24R)-25-(1-hexenyl)-26,27-cyclo-9,10-secocholesta-5,7,10(19),22-tetraene-1,3,24-triol,
[5Z,7E,22E,25 (E)]-(1S,3R,24S)-25-(1-heptenyl)-26,27-cyclo-9,10-secocholesta-5,7,10(19),22-tetraene-1,3,24-triol,
[5Z,7E,22E,25(E)]-(1S,3R,24R)-25-(1-heptenyl)-26,27-cyclo-9,10-secocholesta-5,7,10(19),22-tetraene-1,3,24-triol,
[5Z,7E,22E,25(E)]-(1S,3R,24S)-25-(1-octenyl)-26,27-cyclo-9,10-secocholesta-5,7,10(19),22-tetraene-1,3,24-triol,
[5Z,7E,22E,25(E)]-(1S,3R,24R)-25-(1-octenyl)-26,27-cyclo-9,10-secocholesta-5,7,10(19),22-tetraene-1,3,24-triol,
[5Z,7E,22E,25(E)]-(1S,3R,24S)-25-(1-nonenyl)-26,27-cyclo-9,10-secocholesta-5,7,10(19),22-tetraene-1,3,24-triol,
[5Z,7E,22E,25(E)]-(1S,3R,24R)-25-(1-nonenyl)-26,27-cyclo-9,10-secocholesta-5,7,10(19),22-tetraene-1,3,24-triol,
[5Z,7E,22E,25(E)]-(1S,3R,24S)-25-(1-decenyl)-26,27-cyclo-9,10-secocholesta-5,7,10(19),22-tetraene-1,3,24-triol,
[5Z,7E,22E,25(E)]-(1S,3R,24R)-25-(1-decenyl)-26,27-cyclo-9,10-secocholesta-5,7,10(19),22-tetraene-1,3,24-triol,
[5Z,7E,22E,25(Z)]-(1S,3R,24S)-25-(1-propenyl)-26,27-cyclo-9,10-secocholesta-5,7,10(19),22-tetraene-1,3,24-triol,
[5Z,7E,22E,25(Z)]-(1S,3R,24R)-25-(1-propenyl)-26,27-cyclo-9,10-secocholesta-5,7,10(19),22-tetraene-1,3,24-triol,
[5Z,7E,22E,25(Z)]-(1S,3R,24S)-25-(1-butenyl)-26,27-cyclo-9,10-secocholesta-5,7,10(19),22-tetraene-1,3,24-triol,
[5Z,7E,22E,25(Z)]-(1S,3R,24R)-25-(1-butenyl)-26,27-cyclo-9,10-secocholesta-5,7,10(19),22-tetraene-1,3,24-triol,
[5Z,7E,22E,25(Z)]-(1S,3R,24S)-25-(1-pentenyl)-26,27-cyclo-9,10-secocholesta-5,7,10(19),22-tetraene-1,3,24-triol,
[5Z,7E,22E,25(Z)]-(1S,3R,24R)-25-(1-pentenyl)-26,27-cyclo-9,10-secocholesta-5,7,10(19),22-tetraene-1,3,24-triol,
[5Z,7E,22E,25(Z)]-(1S,3R,24S)-25-(1-hexenyl)-26,27-cyclo-9,10-secocholesta-5,7,10(19),22-tetraene-1,3,24-triol,
[5Z,7E,22E,25(Z)]-(1S,3R,24R)-25-(1-hexenyl)-26,27-cyclo-9,10-secocholesta-5,7,10(19),22-tetraene-1,3,24-triol,
[5Z,7E,22E,25(Z)]-(1S,3R,24S)-25-(1-heptenyl)-26,27-cyclo-9,10-secocholesta-5,7,10(19),22-tetraene-1,3,24-triol,
[5Z,7E,22E,25(Z)]-(1S,3R,24R)-25-(1-heptenyl)-26,27-cyclo-9,10-secocholesta-5,7,10(19),22-tetraene-1,3,24-triol,
[5Z,7E,22E,25(Z)]-(1S,3R,24S)-25-(1-octenyl)-26,27-cyclo-9,10-secocholesta-5,7,10(19),22-tetraene-1,3,24-triol,
[5Z,7E,22E,25(Z)]-(1S,3R,24R)-25-(1-octenyl)-26,27-cyclo-9,10-secocholesta-5,7,10(19),22-tetraene-1,3,24-triol,
[5Z,7E,22E,25(Z)]-(1S,3R,24S)-25-(1-nonenyl)-26,27-cyclo-9,10-secocholesta-5,7,10(19),22-tetraene-1,3,24-triol,
[5Z,7E,22E,25(Z)]-(1S,3R,24R)-25-(1-nonenyl)-26,27-cyclo-9,10-secocholesta-5,7,10(19),22-tetraene-1,3,24-triol,
[5Z,7E,22E,25(Z)]-(1S,3R,24S)-25-(1-decenyl)-26,27-cyclo-9,10-secocholesta-5,7,10(19),22-tetraene-1,3,24-triol, or
[5Z,7E,22E,25(Z)]-(1S,3R,24R)-25-(1-decenyl)-26,27-cyclo-9,10-secocholesta-5,7,10(19),22-tetraene-1,3,24-triol.

27. A compound according to claim 10, wherein Q is —CH$_2$—, —(CH$_2$)$_2$—, —(CH$_2$)$_3$—, —(CH$_2$)$_4$—, —(CH$_2$)$_7$—, —CH$_2$—C(CH$_3$)$_2$—CH$_2$—, —CH$_2$—CH(CH$_3$)—CH$_2$—CH(CH$_3$)—CH$_2$—, —CH$_2$—CH(OH)—CH$_2$—CH(OH)—CH$_2$—, —CH$_2$—CH(OH)—CH$_2$—, —CH$_2$—CH(OH)—CH$_2$—CH(OH)—CH$_2$—, —CH(OCH$_3$)—, —CH$_2$—CH(OC$_2$H$_5$)—, —CH$_2$—CH(OCOCH$_3$)—CH$_2$—CH(OCOCH$_3$)—CH$_2$—, —CH$_2$—CH(OCOC$_4$H$_9$)—CH$_2$—, —CO—CH$_2$, —CO—CH$_2$—CH$_2$—, —CH$_2$COCH$_2$—, —CH(Cl)—, —CH(Cl)—CH$_2$—, —CH$_2$—CH(Cl)—, —CH(NH$_2$)—, —CH(NH$_2$)—CH$_2$—, —CH(N(CH$_3$)$_2$)—, —CH(N(CH$_3$)$_2$)—CH$_2$—, —CH$_2$—CH(N(CH$_3$)$_2$)—CH$_2$—CH(N(CH$_3$)$_2$)—CH$_2$—, —CH(F)—, —CH(F)—CH$_2$—, —CH$_2$—CH(F)—CH$_2$—.

28. A compound according to claim 13, wherein Z is alkyl having 1–12 C atoms or alkenyl having 1–12 C atoms.

29. A compound according to claim 28, wherein Z is methyl, ethyl, propyl, butyl, pentyl, hexyl, heptyl, octyl, nonyl, decyl, 1-propenyl, 1-butenyl, 1-pentenyl, 1-hexeynyl, 1-heptenyl, 1-oxtenyl, 1-nonenyl, or 1-decenyl.

* * * * *